US008334374B2

(12) United States Patent
Waterhouse et al.

(10) Patent No.: US 8,334,374 B2
(45) Date of Patent: Dec. 18, 2012

(54) METHODS AND MEANS FOR OBTAINING MODIFIED PHENOTYPES

(75) Inventors: Peter Michael Waterhouse, Canberra (AU); Ming-Bo Wang, Canberra (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/474,539

(22) Filed: May 17, 2012

(65) Prior Publication Data
US 2012/0270315 A1    Oct. 25, 2012

Related U.S. Application Data

(62) Division of application No. 11/179,504, filed on Jul. 13, 2005, now Pat. No. 8,183,217, which is a division of application No. 10/152,808, filed on May 23, 2002, now Pat. No. 7,138,565, which is a division of application No. 09/373,720, filed on Aug. 13, 1999, now Pat. No. 6,423,885.

(51) Int. Cl.
C07H 21/04 (2006.01)
C12N 5/00 (2006.01)
C12N 15/11 (2006.01)

(52) U.S. Cl. ............... 536/24.5; 514/44 A; 435/325; 435/375

(58) Field of Classification Search .............. None
See application file for complete search history.

(56) References Cited

U.S. PATENT DOCUMENTS

| 3,931,397 | A |   | 1/1976  | Harnden         |
|-----------|---|---|---------|-----------------|
| 4,130,641 | A |   | 12/1978 | Ts'o et al.     |
| 4,283,393 | A |   | 8/1981  | Field et al.    |
| 4,469,863 | A |   | 9/1984  | Ts'o et al.     |
| 4,605,394 | A |   | 8/1986  | Skurkovich      |
| 4,629,320 | A |   | 12/1986 | Lersmacher et al.|
| 4,689,320 | A |   | 8/1987  | Kaji et al.     |
| 4,766,072 | A |   | 8/1988  | Jendrisak et al.|
| 5,017,488 | A |   | 5/1991  | McAllister et al.|
| 5,024,938 | A |   | 6/1991  | Nozaki et al.   |
| 5,034,323 | A |   | 7/1991  | Jorgensen et al.|
| 5,107,065 | A |   | 4/1992  | Shewmaker et al.|
| 5,173,410 | A |   | 12/1992 | Ahlquist        |
| 5,190,931 | A |   | 3/1993  | Inouye          |
| 5,198,346 | A |   | 3/1993  | Ladner          |
| 5,208,149 | A |   | 5/1993  | Inouye          |
| 5,231,020 | A |   | 7/1993  | Jorgensen et al.|
| 5,270,163 | A |   | 12/1993 | Gold et al.     |
| 5,272,065 | A |   | 12/1993 | Inouye et al.   |
| 5,283,184 | A |   | 2/1994  | Jorgensen et al.|
| 5,349,126 | A |   | 9/1994  | Chappell et al. |
| 5,354,854 | A |   | 10/1994 | Bourque         |
| 5,365,015 | A |   | 11/1994 | Grierson et al. |
| 5,405,775 | A |   | 4/1995  | Inouye et al.   |
| 5,413,906 | A |   | 5/1995  | Eberle et al.   |
| 5,434,070 | A |   | 7/1995  | Inouye et al.   |
| 5,453,566 | A |   | 9/1995  | Shewmaker et al.|
| 5,457,189 | A |   | 10/1995 | Crooke et al.   |
| 5,474,935 | A |   | 12/1995 | Chatterjee et al.|
| 5,496,698 | A |   | 3/1996  | Draper          |
| 5,514,546 | A |   | 5/1996  | Kool            |
| 5,530,192 | A |   | 6/1996  | Murase et al.   |
| 5,578,716 | A |   | 11/1996 | Szyf et al.     |
| 5,580,703 | A |   | 12/1996 | Kotin et al.    |
| 5,580,767 | A |   | 12/1996 | Cowsert et al.  |
| 5,583,021 | A |   | 12/1996 | Dougherty       |
| 5,597,718 | A |   | 1/1997  | John et al.     |
| 5,602,242 | A |   | 2/1997  | Ahlquist et al. |
| 5,624,803 | A |   | 4/1997  | Noonberg et al. |
| 5,631,148 | A |   | 5/1997  | Urdea           |
| 5,643,762 | A |   | 7/1997  | Ohshima et al.  |
| 5,674,730 | A | * | 10/1997 | Baim et al. ............ 435/353 |
| 5,681,944 | A | * | 10/1997 | Crooke et al. ............ 536/24.5 |
| 5,683,985 | A |   | 11/1997 | Chu et al.      |
| 5,686,649 | A |   | 11/1997 | Chua et al.     |
| 5,691,140 | A |   | 11/1997 | Noren et al.    |
| 5,693,773 | A |   | 12/1997 | Kandimalla et al.|
| 5,707,835 | A |   | 1/1998  | Haseloff et al. |
| 5,714,323 | A |   | 2/1998  | Ohshima et al.  |
| 5,719,054 | A |   | 2/1998  | Boursnell et al.|
| 5,739,309 | A |   | 4/1998  | Dattagupta et al.|
| 5,747,308 | A |   | 5/1998  | Bebbington et al.|

(Continued)

FOREIGN PATENT DOCUMENTS
AU    B-34025/93    8/1995
(Continued)

OTHER PUBLICATIONS

Abdurashitov, M.A., et al. (1997) "BstAPI, an ApaBi Isochizomer, Cleaves DNA at 5'-GCANNNNNTGC-3'," Nucleic Acids Res., vol. 25, No. 12, pp. 2301-2302.

(Continued)

Primary Examiner — Dana Shin
(74) Attorney, Agent, or Firm — John P. White; Gary J. Gershik; Cooper & Dunham LLP

(57) ABSTRACT

Methods and means are provided for reducing the phenotypic expression of a nucleic acid of interest in eukaryotic cells, particularly in plant cells, by providing aberrant, preferably unpolyadenylated, target-specific RNA to the nucleus of the host cell. Preferably, the unpolyadenylated target-specific RNA is provided by transcription of a chimeric gene comprising a promoter, a DNA region encoding the target-specific RNA, a self-splicing ribozyme and a DNA region involved in 3' end formation and polyadenylation.

19 Claims, 3 Drawing Sheets

U.S. PATENT DOCUMENTS

| | | | |
|---|---|---|---|
| 5,747,338 A | 5/1998 | Giese et al. |
| 5,780,269 A | 7/1998 | Inouye et al. |
| 5,795,715 A | 8/1998 | Livache et al. |
| 5,798,265 A | 8/1998 | Springer et al. |
| 5,801,154 A | 9/1998 | Baracchini et al. |
| 5,808,036 A | 9/1998 | Kool |
| 5,814,500 A | 9/1998 | Dietz |
| 5,850,026 A | 12/1998 | DeBonte et al. |
| 5,858,981 A | 1/1999 | Schreiber et al. |
| 5,859,347 A | 1/1999 | Brown et al. |
| 5,874,555 A | 2/1999 | Dervan et al. |
| 5,879,906 A | 3/1999 | Jefferson et al. |
| 5,891,855 A | 4/1999 | Florkiewicz |
| 5,908,779 A | 6/1999 | Carmichael et al. |
| 5,939,600 A | 8/1999 | Goldbach et al. |
| 5,952,546 A | 9/1999 | Bedbrook et al. |
| 5,972,704 A | 10/1999 | Draper et al. |
| 5,994,526 A * | 11/1999 | Meulewaeter et al. ...... 536/24.1 |
| 5,998,383 A | 12/1999 | Wright et al. |
| 6,010,908 A | 1/2000 | Gruenert et al. |
| 6,022,863 A | 2/2000 | Peyman |
| 6,054,299 A | 4/2000 | Conrad |
| 6,069,298 A | 5/2000 | Gengenbach et al. |
| 6,133,024 A | 10/2000 | Helene et al. |
| 6,146,886 A | 11/2000 | Thompson |
| 6,150,585 A | 11/2000 | Goldbach et al. |
| 6,225,290 B1 | 5/2001 | German et al. |
| 6,291,504 B1 | 9/2001 | Nugeil et al. |
| 6,344,316 B1 | 2/2002 | Lockhart et al. |
| 6,350,575 B1 | 2/2002 | Lusky et al. |
| 6,369,038 B1 | 4/2002 | Blumenfeld et al. |
| 6,372,965 B1 | 4/2002 | Lightner et al. |
| 6,423,885 B1 | 7/2002 | Waterhouse et al. |
| 6,451,603 B1 | 9/2002 | Atkins et al. |
| 6,506,559 B1 | 1/2003 | Fire et al. |
| 6,531,647 B1 | 3/2003 | Baulcombe et al. |
| 6,573,099 B2 | 6/2003 | Graham et al. |
| 6,610,321 B2 | 8/2003 | Huang et al. |
| 6,635,805 B1 | 10/2003 | Baulcombe et al. |
| 6,849,448 B1 | 2/2005 | D'Apice |
| 6,919,466 B2 | 7/2005 | Lightner et al. |
| 6,995,258 B1 | 2/2006 | Rossi et al. |
| 7,064,185 B2 | 6/2006 | Lau |
| 7,138,565 B2 | 11/2006 | Waterhouse et al. |
| 7,754,697 B2 | 7/2010 | Graham et al. |
| 8,048,670 B2 | 11/2011 | Graham et al. |
| 8,053,419 B2 | 11/2011 | Graham et al. |
| 8,168,774 B2 | 5/2012 | Graham et al. |
| 8,183,217 B2 | 5/2012 | Waterhouse et al. |
| 8,263,573 B2 | 9/2012 | Whyard et al. |
| 2002/0086356 A1 | 7/2002 | Tuschl et al. |
| 2002/0114784 A1 | 8/2002 | Li et al. |
| 2002/0150968 A1 | 10/2002 | Wang et al. |
| 2002/0150986 A1 | 10/2002 | Lau |
| 2002/0166144 A1 | 11/2002 | Green et al. |
| 2002/0168707 A1 | 11/2002 | Graham |
| 2003/0018993 A1 | 1/2003 | Gutterson et al. |
| 2003/0027783 A1 | 2/2003 | Zernicka-Goetz |
| 2003/0036197 A1 | 2/2003 | Glassman et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0061626 A1 | 3/2003 | Plaetinck et al. |
| 2003/0074684 A1 | 4/2003 | Graham et al. |
| 2003/0148519 A1 | 8/2003 | Engelke et al. |
| 2003/0159161 A1 | 8/2003 | Graham et al. |
| 2003/0165894 A1 | 9/2003 | Waterhouse et al. |
| 2004/0022748 A1 | 2/2004 | Ananthapadmanabhan et al. |
| 2004/0064842 A1 | 4/2004 | Graham et al. |
| 2004/0106566 A1 | 6/2004 | Lin et al. |
| 2004/0138168 A1 | 7/2004 | Satishchandran et al. |
| 2004/0180439 A1 | 9/2004 | Graham et al. |
| 2004/0214330 A1 | 10/2004 | Waterhouse et al. |
| 2004/0231016 A1 | 11/2004 | Wang et al. |
| 2004/0234504 A1 | 11/2004 | Verma et al. |
| 2004/0237145 A1 | 11/2004 | Graham et al. |
| 2004/0266005 A1 | 12/2004 | Graham et al. |
| 2005/0095199 A1 | 5/2005 | Whyard et al. |
| 2005/0250208 A1 | 11/2005 | Graham et al. |
| 2005/0251877 A1 | 11/2005 | Waterhouse et al. |
| 2006/0014715 A1 | 1/2006 | Graham et al. |
| 2006/0178335 A1 | 8/2006 | Waterhouse et al. |
| 2007/0056057 A1 | 3/2007 | Waterhouse et al. |
| 2007/0078105 A1 | 4/2007 | Waterhouse et al. |
| 2008/0044906 A1 | 2/2008 | Waterhouse et al. |
| 2008/0050342 A1 | 2/2008 | Fire et al. |
| 2008/0081373 A1 | 4/2008 | Fire et al. |
| 2008/0104732 A1 | 5/2008 | Waterhouse et al. |
| 2008/0248576 A1 | 10/2008 | Fire et al. |
| 2009/0165153 A1 | 6/2009 | Wang et al. |
| 2010/0058490 A1 | 3/2010 | Waterhouse et al. |
| 2011/0076681 A1 | 3/2011 | Waterhouse et al. |
| 2012/0135517 A1 | 5/2012 | Graham et al. |

FOREIGN PATENT DOCUMENTS

| | | |
|---|---|---|
| AU | 20891/91 | 10/1997 |
| AU | 20891/97 | 10/1997 |
| AU | PP2492 | 3/1998 |
| AU | PP2499 | 3/1998 |
| AU | 729454 | 5/1998 |
| AU | 729454 | 2/2001 |
| AU | 2001195225 A1 | 1/2002 |
| CA | 2012312 | 9/1990 |
| CA | 2370628 A1 | 10/2000 |
| EP | 0213921 A2 | 3/1987 |
| EP | 0223399 | 5/1987 |
| EP | 0240208 | 10/1987 |
| EP | 0281380 | 9/1988 |
| EP | 0286224 | 10/1988 |
| EP | 0300680 A2 | 1/1989 |
| EP | 0303516 A2 | 2/1989 |
| EP | 0306347 | 3/1989 |
| EP | 0308066 | 3/1989 |
| EP | 0318281 | 5/1989 |
| EP | 0325018 | 7/1989 |
| EP | 0347501 | 12/1989 |
| EP | 0350151 | 1/1990 |
| EP | 0387775 | 9/1990 |
| EP | 0467349 | 1/1992 |
| EP | 0522880 | 1/1993 |
| EP | 0560156 | 9/1993 |
| EP | 0647715 | 4/1995 |
| EP | 0465572 | 6/1995 |
| EP | 0779364 | 6/1997 |
| EP | 0779365 | 6/1997 |
| EP | 0784094 | 7/1997 |
| EP | 0242016 | 10/1997 |
| EP | 0532380 | 1/1999 |
| EP | 0921195 | 6/1999 |
| EP | 0983370 | 3/2000 |
| EP | 0426195 B1 | 10/2001 |
| EP | 0458367 B1 | 10/2001 |
| EP | 1229134 | 8/2002 |
| GB | 2353282 A | 2/2001 |
| GB | 2377221 A | 9/2001 |
| JP | H09-110894 A | 4/1997 |
| JP | H09-227413 | 9/2007 |
| WO | WO 89/05852 | 6/1989 |
| WO | WO 89/10396 | 11/1989 |
| WO | WO 90/11682 | 10/1990 |
| WO | WO 90/12094 | 10/1990 |
| WO | WO 90/12488 | 11/1990 |
| WO | WO 90/14090 | 11/1990 |
| WO | WO 91/02069 | 2/1991 |
| WO | WO 91/16426 | 10/1991 |
| WO | WO 91/16440 | 10/1991 |
| WO | WO 92/04456 | 3/1992 |
| WO | WO 92/11375 | 7/1992 |
| WO | WO 92/11376 | 7/1992 |
| WO | WO 92/13070 | 8/1992 |
| WO | WO 92/18522 | 10/1992 |
| WO | WO 92/18625 | 10/1992 |
| WO | WO 92/19732 | 11/1992 |
| WO | WO 92/21757 | 12/1992 |
| WO | WO 93/05159 | 3/1993 |
| WO | WO 93/10251 | 5/1993 |
| WO | WO 93/17098 | 9/1993 |

| WO | WO 93/23551 | 11/1993 |
| WO | WO 94/01550 | 1/1994 |
| WO | WO 94/03607 | 2/1994 |
| WO | WO 94/07367 | 4/1994 |
| WO | WO 94/09143 | 4/1994 |
| WO | WO 94/17194 | 8/1994 |
| WO | WO 94/18337 | 8/1994 |
| WO | WO 94/29465 | 12/1994 |
| WO | WO 95/03406 | 2/1995 |
| WO | WO 95/07993 | 3/1995 |
| WO | WO 95/08350 | 3/1995 |
| WO | WO 95/09920 | 4/1995 |
| WO | WO 95/10607 | 4/1995 |
| WO | WO 95/15378 | 6/1995 |
| WO | WO 95/15394 | 6/1995 |
| WO | WO 95/18223 | 7/1995 |
| WO | WO 95/18854 | 7/1995 |
| WO | WO 95/23225 | 8/1995 |
| WO | WO 95/34668 | 12/1995 |
| WO | WO 96/08558 | 3/1996 |
| WO | WO 96/35706 | 11/1996 |
| WO | WO 97/01952 | 1/1997 |
| WO | WO 97/10360 A1 | 3/1997 |
| WO | WO 97/11170 | 3/1997 |
| WO | WO 97/11170 A1 | 3/1997 |
| WO | WO 92/17596 | 10/1997 |
| WO | WO 97/44450 | 11/1997 |
| WO | WO 97/44460 | 11/1997 |
| WO | WO 97/49814 | 12/1997 |
| WO | WO 98/05770 | 2/1998 |
| WO | WO 98/18811 | 5/1998 |
| WO | WO 98/36083 | 8/1998 |
| WO | WO 98/37213 | 8/1998 |
| WO | WO 98/44138 | 10/1998 |
| WO | WO 98/50408 | 11/1998 |
| WO | WO 98/53083 | 11/1998 |
| WO | WO 99/32619 | 1/1999 |
| WO | WO 99/09045 | 2/1999 |
| WO | WO 99/15682 | 4/1999 |
| WO | WO 99/25853 | 5/1999 |
| WO | WO 99/29879 | 6/1999 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 99/61632 | 12/1999 |
| WO | WO 00/01846 | 1/2000 |
| WO | WO 00/44895 | 8/2000 |
| WO | WO 00/44914 | 8/2000 |
| WO | WO 00/63364 | 10/2000 |
| WO | WO 00/63397 | 10/2000 |
| WO | WO 00/76308 | 12/2000 |
| WO | WO 01/04313 | 1/2001 |
| WO | WO 01/12824 | 2/2001 |
| WO | WO 01/19857 | 3/2001 |
| WO | WO 01/29058 | 4/2001 |
| WO | WO 01/36646 | 5/2001 |
| WO | WO 01/37654 | 5/2001 |
| WO | WO 01/38359 | 5/2001 |
| WO | WO 01/48183 | 7/2001 |
| WO | WO 01/70949 | 9/2001 |
| WO | WO 01/88114 | 11/2001 |
| WO | WO 02/44321 | 6/2002 |
| WO | WO 03/006477 | 1/2003 |
| WO | WO 03/022052 | 3/2003 |
| WO | WO 03/027298 | 4/2003 |
| WO | WO 03/056012 | 7/2003 |
| WO | WO 03/076619 | 9/2003 |
| WO | WO 03/095647 | 11/2003 |

OTHER PUBLICATIONS

Appeal Brief filed on Mar. 6, 2009 in U.S. Appl. No. 10/805,804.
Anderson, W.F. (1998) "Human Gene Therapy" Nature 392(6679 Suppl.):25-30.
Barabino, S.M., et al. (1997) "Inactivation of the zebrafish homologue of Chx10 by antisense oligonucleotides causes eye malformations similar to the ocular retardation phenotype," Mech. Dev. 63:133-143.
Buchman, A.R., and Berg, P. (1988) "Comparison of intron-dependent and intron-independent gene expression," Mol. Cell. Biol. 8(10):4395-405.
Cameron, F.H. and Jennings, P.A. (1991) "Inhibition of Gene Expression by a Short Sense Fragment" Nucleic Acids Research 19(3): 469-475.
Caplen et al. (2002) "A New Approach to the Inhibition of Gene Expression" Trends in Biotechnology 20:49-51.
Declaration of David M. Stalker filed in opposition to Australian Patent Application No. 778474 (Nov. 4, 2008).
Dale et al. (2000) "A test of the model to predict unusually stable RNA hairpin loop stability" RNA 6:608-615.
Day, A.G., et al. (1991) "Expression of an antisense viral gene in transgenic tobacco confers resistance to the DNA virus tomato golden mosaic virus," Proc. Natl. Acad. Sci. U.S.A. 88:6721-6725.
Dhalla, A.K., et al. (1998) "chk-YB-1b, a Y-box binding protein activates transcription from rat alpha1(I) procollagen gene promoter," Biochem. J. 336(2) :373-379.
Elbashir, S. M. et al. (2001) "Duplexes of 21-nucleotide RNAs mediate RNA interference in cultured mammalian cells." Nature 411 (6836):494-8.
Fire et al. (1999) "RNA-triggered gene silencing," Trends Genet. 15(9):358-63.
Gilbert, S.F. (1997) "Development Biology" 5th ed., Sinauer Associates Inc., Sunderland, MA, pubs., p. 466.
Good et al., (1997) "Expression of small, therapeutic RNAs in human cell nuclei" Gene Ther. 4(1):45-54.
Harborth et al. (2003) "Sequence, Chemical, and Structural Variation of Small Interfering RNAs and Short Hairpin RNAs and the Effect on Mammalian Gene Silencing" Antisense and Nucleic Acid Drug Development 13:83-105.
Haselbeck, R.C., and Greer, C.L. (1993) "Minimum intron requirements for tRNA splicing and nuclear transport in *Xenopus oocytes*," Biochemistry 32(33):8575-81.
Holen et al. (2002) "Positional effects of short interfering RNAs targeting the human coagulation trigger Tissue Factor" Nucleic Acids Research 30(8):1757-1766.
Kappel, C.A., et al. (1992) "Regulating gene expression in transgenic animals," Curr. Opin. Biotechnol. 3(5):548-53.
McGarry, T.J., and Lindquist, S. (1986) "Inhibition of heat shock protein synthesis by heat-inducible antisense RNA," Proc. Natl. Acad. Sci. U.S.A 83:399-403.
McKenzie, et al. (1999) "Transplantation," pp. 827-874 (Ginns, Leo C., Cosimi, A. Benedict, & Morris, Peter J., eds.), Blackwell Science Inc., Malden, Mass.
McManus, et al. (2002) "Gene Silencing using micro-RNA designed hairpins" RNA 8:842-860.
McManus, et al. (2002) "Small Interfering RNA-Mediated Gene Silencing in T Lymphocytes" Journal of Immunology 169:5754-5760.
Metzlaff, M. et al. (1997) "RNA-Mediated RNA Degradation and Chalcone Synthase A Silencing in *Petunia*" Cell 88:845-854.
Minks MA et al. (1979) "Structural requirements of double-stranded RNA for the activation of 2',5'-oligo(A) polymerase and protein kinase of interferon-treated HeLa cells" J. Biol. Chem. vol. 254, No. 20: 10180-10183.
Nobelprize.org: The Nobel Prize in Physiology or Medicine 2006, Press Release of the Nobel Assembly at Karolinska Institute (Oct. 2, 2006).
Parrish, S. et al. (2000) "Functional Anatomy of a dsRNA Trigger: Differential Requirement for the Two Trigger Strands in RNA Interference" Mol. Cell 6:1077-1087.
Powell-Coffman, J.A., et al. (1996) "Onset of *C. elegans* gastrulation is blocked by inhibition of embryonic transcription with an RNA polymerase antisense RNA," Dev. Biol. 178:472-83.
Randall et al. (2003) "Clearance of replicating hepatitis C virus replicon RNAs in cell culture by small interfering RNAs" PNAS 100(1):235-240.
Reply Brief to Examiner's Answer filed on Aug. 26, 2009, U.S. Appl. No. 10/805,804.
Scherr et al. (2003) "Gene Silencing Mediated by Small Interfering RNA's in Mammalian Cells" Current Medicinal Chemistry 10:245-256.

Schiedner, G., et al. (1998) "Genomic DNA transfer with a high-capacity adenovirus vector results in improved in vivo gene expression and decreased toxicity," Nat. Genet. 18(2):180-3.
Selker (1999) "Gene Silencing:repeats that count" Cell 97(2):157-160.
Shi, Y. (2000) "Mammalian RNAi for the masses" Trends Genet. 19(1):9-1.
Stam et al. (1997) "Post-Transcriptional Silencing of Chalcone Synthase in *Petunia* by Inverted Transgene Repeats," The Plant Journal vol. 12, No. 1, pp. 63-82.
Swamynathan, S.K., et al. (1997) "Chicken YB-2, a Y-box protein, is a potent activator of Rous sarcoma virus long terminal repeat-driven transcription in avian fibroblasts," J. Virol. 71:2873-2880.
Touchette (1996) "Gene Therapy—Not Ready for Prime Time (News)" Nat. Med. 2(1) 7-8.
Verma et al. (1997) "Gene Therapy—Promises, Problems and Prospects" Nature 389:239-242.
Vickers, T.A., et al. (2003) "Efficient Reduction of Target RNAs by Small Interfering RNA and RNase H-dependent Antisense Agents. A comparative analysis" J. Biol. Chem. 278(9):7108-7118.
Viville, S. (1997) "Mouse Genetic Manipulation via Homologous Recombination," pp. 307-321, in "Transgenic Animals Generation and Use," (Houdebine, L.M., ed.), Harwood Academic Publishers, France, pubs.
Wang et al (1997) "A factor IX-deficient mouse model for hemophilia B gene therapy" PNAS 94:11563-11566.
Wall, RJ (1996) "Transgenic Livestock: Progress and Prospects for the Future" Theriogenology 45:57-68.
Wharton et al. (1994) "Role of virion M2 protein in influenza virus uncoating: specific reduction in the rate of membrane fusion between virus and liposomes by amantadine," Journal of General Virology, 75:945-948.
Zhang et al. (2004) "Single Processing Center Models for Human Dicer and Bacterial RNase III," Cell (118): 57-68.
Amendment submitted Sep. 2, 2008 in connection with U.S. Appl. No. 11/179,504, filed Jul. 13, 2005.
Citron et al. (1990) "The c4 Repressors of Bacteriophages P1 and P7 Are Antisense RNAs" Cell 62:591-598.
Decision on Appeal, issued Mar. 30, 2012 in connection with U.S. Appl. No. 09/287,632.
Request for Rehearing, filed May 30, 2012 in connection with U.S. Appl. No. 09/287,632.
Record of Oral Hearing, issued Feb. 10, 2012 in connection with U.S. Appl. No. 09/287,632.
Notice of Opposition to a European Patent, filed by BASF SE on Jun. 26, 2012 in connection with European Patent No. EP1624060 (granted from European Patent Application No. EP05013010.3).
Opposition Brief, filed by BASF SE on Jun. 26, 2012 in connection with European Patent No. EP1624060 (granted from European Patent Application No. EP05013010.3).
Notice of Opposition to a European Patent, filed by BASF SE on Jun. 26, 2012 in connection with European Patent No. EP1555317 (granted from European Patent Application No. EP04015041.9).
Opposition Brief, filed by BASF SE on Jun. 26, 2012 in connection with European Patent No. EP1555317 (granted from European Patent Application No. EP04015041.9).
Opposition Brief, filed by Strawman Limited on Jun. 27, 2012 in connection with European Patent No. EP1555317 (granted from European Patent Application No. EP04015041.9).
Feb. 23, 2012 Office Action, issued by the Canadian Patent Office in connection with Canadian Patent Application No. 2,381,921.
U.S. Appl. No. 09/100,813, filed Jun. 19, 1998, Michael Wayne Graham et al.
U.S. Appl. No. 09/100,813 Including complete file history, filed Jun. 19, 1998, Michael Wayne Graham et al.
U.S. Appl. No. 09/646,807, filed Dec. 5, 2000, Michael Wayne Graham et al.
U.S. Appl. No. 09/646,807 Including complete file history, filed Dec. 5, 2000, Michael Wayne Graham et al.
U.S. Appl. No. 11/218,999, filed Sep. 2, 2005, Michael Wayne Graham et al.
Advisory Action issued Jul. 20, 2007 in connection with U.S. Appl. No. 10/821,710, filed Apr. 8, 2004.
Advisory Action issued Sep. 14, 2005 in connection with U.S. Appl. No. 10/821,710, filed Apr. 8, 2004.
Amendment submitted Apr. 29, 2005 in connection with U.S. Appl. No. 10/821,710, filed Apr. 8, 2004.
Amendment submitted Aug. 29, 2005 in connection with U.S. Appl. No. 10/821,710, filed Apr. 8, 2004.
Amendment submitted Dec. 15, 2004 in connection with U.S. Appl. No. 10/821,710, filed Apr. 8, 2004.
Amendment submitted Feb. 7, 2008 in connection with U.S. Appl. No. 10/821,710, filed Apr. 8, 2004.
Amendment submitted Jul. 12, 2007 in connection with U.S. Appl. No. 10/821,710, filed Apr. 8, 2004.
Amendment submitted Jul. 25, 2007 in connection with U.S. Appl. No. 10/821,710, filed Apr. 8, 2004.
Amendment submitted Nov. 20, 2006 in connection with U.S. Appl. No. 10/821,710, filed Apr. 8, 2004.
Amendment submitted Oct. 31, 2007 in connection with U.S. Appl. No. 10/821,710, filed Apr. 8, 2004.
Decision on Petition to Make Special Under 37 CFR 1.102(d) submitted Jul. 23, 2004 in connection with U.S. Appl. No. 10/821,710, filed Apr. 8, 2004.
Interview Summary issued Nov. 6, 2006 in connection with U.S. Appl. No. 10/821,710, filed Apr. 8, 2004.
Notice of Abandonment issued Dec. 15, 2008 in connection with U.S. Appl. No. 10/821,710, filed Apr. 8, 2004.
Office Action issued Apr. 17, 2008 in connection with U.S. Appl. No. 10/821,710, filed Apr. 8, 2004.
Office Action issued Aug. 7, 2007 in connection with U.S. Appl. No. 10/821,710, filed Apr. 8, 2004.
Office Action issued Feb. 11, 2005 in connection with U.S. Appl. No. 10/821,710, filed Apr. 8, 2004.
Office Action issued Feb. 8, 2005 in connection with U.S. Appl. No. 10/821,710, filed Apr. 8, 2004.
Office Action issued Jan. 12, 2007 in connection with U.S. Appl. No. 10/821,710, filed Apr. 8, 2004.
Office Action issued Jun. 19, 2006 in connection with U.S. Appl. No. 10/821,710, filed Apr. 8, 2004.
Office Action issued Jun. 29, 2005 in connection with U.S. Appl. No. 10/821,710, filed Apr. 8, 2004.
Office Action issued Oct. 15, 2004 in connection with U.S. Appl. No. 10/821,710, filed Apr. 8, 2004.
Petition to Make Special Under 37 CFR 1.102(d) submitted Jul. 23, 2004 in connection with U.S. Appl. No. 10/821,710, filed Apr. 8, 2004.
Preliminary Amendment submitted Dec. 21, 2005 in connection with U.S. Appl. No. 10/821,710, filed Apr. 8, 2004.
Request to Correct Inventorship Under 37 C.F.R. §1.48(a) submitted Dec. 12, 2007 in connection with U.S. Appl. No. 10/821,710, filed Apr. 8, 2004.
Amendment submitted Feb. 19, 2008 in connection with U.S. Appl. No. 11/218,999, filed Sep. 2, 2005.
Amendment submitted Jun. 17, 2008 in connection with U.S. Appl. No. 11/218,999, filed Sep. 2, 2005.
Amendment submitted Oct. 31, 2007 in connection with U.S. Appl. No. 11/218,999, filed Sep. 2, 2005.
Office Action issued May 21, 2008 in connection with U.S. Appl. No. 11/218,999, filed Sep. 2, 2005.
Office Action issued Sep. 17, 2007 in connection with U.S. Appl. No. 11/218,999, filed Sep. 2, 2005.
Office Action issued Sep. 30, 2008 in connection with U.S. Appl. No. 11/218,999, filed Sep. 2, 2005.
Preliminary Amendment to the Accompanying Divisional Application Filed Under 37 C.F.R. §1.53, Submission of Sequence Listing and Information Disclosure Statement submitted Sep. 2, 2005 in connection with U.S. Appl. No. 11/218,999, filed Sep. 2, 2005.
Request to Correct Inventorship Under 37 C.F.R. §1.48(a) submitted Oct. 31, 2007 in connection with U.S. Appl. No. 11/218,999, filed Sep. 2, 2005.
Amendment issued Jan. 24, 2008 in connection with U.S. Appl. No. 10/646,070, filed Aug. 22, 2003.
Amendment submitted Apr. 7, 2005 in connection with U.S. Appl. No. 10/646,070, filed Aug. 22, 2003.

Amendment submitted Aug. 11, 2006 in connection with U.S. Appl. No. 10/646,070, filed Aug. 22, 2003.
Amendment submitted Dec. 15, 2004 in connection with U.S. Appl. No. 10/646,070, filed Aug. 22, 2003.
Amendment submitted Dec. 27, 2005 in connection with U.S. Appl. No. 10/646,070, filed Aug. 22, 2003.
Amendment submitted Feb. 28, 2007 in connection with U.S. Appl. No. 10/646,070, filed Aug. 22, 2003.
Amendment submitted Jul. 24, 2006 in connection with U.S. Appl. No. 10/646,070, filed Aug. 22, 2003.
Amendment submitted Jul. 24, 2008 in connection with U.S. Appl. No. 10/646,070, filed Aug. 22, 2003.
Amendment submitted Jun. 22, 2006 in connection with U.S. Appl. No. 10/646,070, filed Aug. 22, 2003.
Amendment submitted Oct. 10, 2008 in connection with U.S. Appl. No. 10/646,070, filed Aug. 22, 2003.
Amendment submitted Oct. 29, 2007 in connection with U.S. Appl. No. 10/646,070, filed Aug. 22, 2003.
Amendment, including Exhibits A to I submitted Jul. 24, 2008 in connection with U.S. Appl. No. 10/646,070, filed Aug. 22, 2003.
Decision on Petition to Make Special Under 37 CFR 1.102(d) submitted Jul. 27, 2004 in connection with U.S. Appl. No. 10/646,070, filed Aug. 22, 2003.
Interview Summary issued Dec. 11, 2007 in connection with U.S. Appl. No. 10/646,070, filed Aug. 22, 2003.
Notice to Comply with Requirements for Patent Applications Containing Nucleotide Sequence and/or Amino Acid Protein Sequence Disclosures issued Oct. 27, 2005 in connection with U.S. Appl. No. 10/646,070, filed Aug. 22, 2003.
Office Action issued Apr. 27, 2007 in connection with U.S. Appl. No. 10/646,070, filed Aug. 22, 2003.
Office Action issued Aug. 11, 2006 in connection with U.S. Appl. No. 10/646,070, filed Aug. 22, 2003.
Office Action issued Aug. 28, 2006 in connection with U.S. Appl. No. 10/646,070, filed Aug. 22, 2003.
Office Action issued Jul. 24, 2006 in connection with U.S. Appl. No. 10/646,070, filed Aug. 22, 2003.
Office Action issued Nov. 4, 2008 in connection with U.S. Appl. No. 10/646,070, filed Aug. 22, 2003.
Office Action issued Oct. 15, 2004 in connection with U.S. Appl. No. 10/646,070, filed Aug. 22, 2003.
Petition to Make Special Under 37 CFR 1.102(d) submitted Jul. 27, 2004 in connection with U.S. Appl. No. 10/646,070, filed Aug. 22, 2003.
Preliminary Amendment submitted Aug. 22, 2003 in connection with U.S. Appl. No. 10/646,070, filed Aug. 22, 2003.
Amendment submitted Dec. 18, 2002 in connection with U.S. Appl. No. 09/646,807, filed Dec. 5, 2000.
Amendment submitted Dec. 27, 2005 in connection with U.S. Appl. No. 09/646,807, filed Dec. 5, 2000.
Amendment submitted Dec. 28, 2006 in connection with U.S. Appl. No. 09/646,807, filed Dec. 5, 2000.
Amendment submitted Dec. 7, 2004 in connection with U.S. Appl. No. 09/646,807, filed Dec. 5, 2000.
Amendment submitted Mar. 10, 2005 in connection with U.S. Appl. No. 09/646,807, filed Dec. 5, 2000.
Amendment submitted Sep. 8, 2003 in connection with U.S. Appl. No. 09/646,807, filed Dec. 5, 2000.
Communication issued Feb. 17, 2005 in connection with U.S. Appl. No. 09/646,807, filed Dec. 5, 2000.
Communication issued Oct. 27, 2005 in connection with U.S. Appl. No. 09/646,807, filed Dec. 5, 2000.
Office Action issued Dec. 17, 2003 in connection with U.S. Appl. No. 09/646,807, filed Dec. 5, 2000.
Office Action issued Jul. 8, 2008 in connection with U.S. Appl. No. 09/646,807, filed Dec. 5, 2000.
Office Action issued Jun. 28, 2006 in connection with U.S. Appl. No. 09/646,807, filed Dec. 5, 2000.
Office Action issued Mar. 7, 2003 in connection with U.S. Appl. No. 09/646,807, filed Dec. 5, 2000.
Office Action issued Nov. 18, 2002 in connection with U.S. Appl. No. 09/646,807, filed Dec. 5, 2000.

Petition for Unintentionally Delayed Claim of Priority under 37 CFR §1.78(a)(3) submitted Dec. 28, 2006 in connection with U.S. Appl. No. 09/646,807, filed Dec. 5, 2000.
Preliminary Amendment submitted Jul. 30, 2001 in connection with U.S. Appl. No. 09/646,807, filed Dec. 5, 2000.
Preliminary Amendment submitted May 14, 2001 in connection with U.S. Appl. No. 09/646,807, filed Dec. 5, 2000.
Preliminary Amendment submitted Sep. 20, 2000 in connection with U.S. Appl. No. 09/646,807, filed Dec. 5, 2000.
Request to Correct Inventorship Under 37 C.F.R. §1.48(a) submitted Dec. 12, 2007 in connection with U.S. Appl. No. 09/646,807, filed Dec. 5, 2000.
Sep. 9, 2011 Office Action issued in connection with U.S. Appl. No. 11/218,999, filed Sep. 2, 2005.
Dec. 9, 2011 Amendment in Response to Sep. 9, 2011 Office Action filed in connection with U.S. Appl. No. 11/218,999, filed Sep. 2, 2005.
Dec. 30, 2011 Final Office Action issued in connection with U.S. Appl. No. 11/218,999, filed Sep. 2, 2005.
Jan. 19, 2012 Communication in Response to Dec. 30, 2011 Final Office Action issued in connection with U.S. Appl. No. 11/218,999, filed Sep. 2, 2005.
Office Action issued Oct. 9, 2009 in connection with U.S. Appl. No. 11/218,999, filed Sep. 2, 2005.
Amendment submitted Mar. 30, 2009 in connection with U.S. Appl. No. 11/218,999, filed Sep. 2, 2005.
Communication issued May 21, 2009 in connection with U.S. Appl. No. 11/218,999, filed Sep. 2, 2005.
Response to Communication submitted Jun. 22, 2009 in connection with U.S. Appl. No. 11/218,999, filed Sep. 2, 2005.
Supplemental Response to Mar. 30, 2009 Amendment Filed in Response to Sep. 30, 2008 Office Action filed Aug. 4, 2009 in connection with U.S. Appl. No. 11/218,999, filed Sep. 2, 2005.
Amendment in Response to Oct. 9, 2009 Final Office Action as a Submission to Accompanying Request for Continued Examination submitted Mar. 9, 2010 in connection with U.S. Appl. No. 11/218,999, filed Sep. 2, 2005.
Office Action issued Apr. 21, 2010 in connection with U.S. Appl. No. 11/218,999, filed Sep. 2, 2005.
Amendment and Supplemental Information Disclosure Statement as a Submission Accompanying a Request for Continued Examination filed Dec. 15, 2010 in connection with U.S. Appl. No. 11/218,999, filed Sep. 2, 2005.
Office Action, issued Jun. 9, 2009 in connection with U.S. Appl. No. 10/646,070, filed Jul. 13, 2005.
Amendment submitted May 11, 2009 in connection with U.S. Appl. No. 10/646,070, filed Jul. 13, 2005.
Amendment submitted Jul. 15, 2009 in connection with U.S. Appl. No. 10/646,070, filed Jul. 13, 2005.
Terminal Disclaimer submitted Nov. 11, 2009 in connection with U.S. Appl. No. 10/646,070, filed Jul. 13, 2005.
Terminal Disclaimer submitted Dec. 14, 2009 in connection with U.S. Appl. No. 10/646,070, filed Jul. 13, 2005.
Notice of Allowability issued Jan. 27, 2010 in connection with U.S. Appl. No. 10/646,070, filed Aug. 22, 2003.
Supplemental Information Disclosure Statement submitted Apr. 27, 2010 in connection with U.S. Appl. No. 10/646,070, filed Aug. 22, 2003.
Issue Notification issued Jun. 23, 2010 in connection with U.S. Appl. No. 10/646,070, filed Aug. 22, 2003.
Third party observations under article 115 EPC against European Patent Application EP 98964202.0 in the name of Carnegie Institution of Washington, submitted to the European Patent Office on Mar. 24, 2010.
Office Action issued Aug. 28, 2009 in connection with Canadian Patent Application No. 2455490, issued by the Canadian Intellectual Property Office.
May 16, 2011 Request for Revocation Under s72 UK Patent Act 1977 of GB2353282.
Agami et al. (2002) "RNAi and Related Mechanisms and Their Potential Use for Therapy" Current Opinion in Chemical Biology 6:829-834.

Bhargava A., et al. (2002) "Glucocorticoids prolong Ca(2+) transients in hippocampal-derived H19-7 neurons by repressing the plasma membrane Ca(2+)-ATPase-1" Mol Endocrinol. 16(7):1629-37.

Bhargava A., et al. (2004) "Long double-stranded RNA-mediated RNA interference as a tool to achieve site-specific silencing of hypothalamic neuropeptides" Brain Res Brain Res Protoc. (2):115-25.

Definition of "palindrome" (1999) Glossary of biotechnology and genetic engineering, p. 172, Zaid, A., et al., eds., Food and Agriculture Organization of the United Nations, Rome, Italy.

Diallo M., et al. (2003) "Long endogenous dsRNAs can induce complete gene silencing in mammalian cells and primary cultures" Oligonucleotides. 13(5):381-92.

Fedoriw A.M., et al. (2004) "Transgenic RNAi reveals essential function for CTCF in H19 gene imprinting" Science. 303(5655):238-40.

Gan L., et al. (2002) "Specific interference with gene expression and gene function mediated by long dsRNA in neural cells" J Neurosci Methods. 121(2):151-7.

Gitlin, L., et al. (2005) "Poliovirus escape from RNA interference: short interfering RNA-target recognition and implications for therapeutic approaches," J. Virol. 79:1027-1035.

Lazar, S. et al. (2004) "Selective degradation of cyclin B1 mRNA in rat oocytes by RNA interference (RNAi)" J Mol Endocrinol. 33(1):73-85.

Park, W.S., et al. (2001) "Specific inhibition of HIV-1 gene expression by double-stranded RNA," Nucleic Acids Research Suppl. 1:219-220.

Park, W.S., et al. (2002) "Prevention of HIV-1 infection in human peripheral blood mononuclear cells by specific RNA interference," Nucleic Acids Res. 30:4830-4835.

Polyadenylation, Wikipedia, 3 pages, http://en.wikipedia.org/wiki/Polyadenylation (Feb. 20, 2007).

Polyadenylation, Wikipedia, 3 pages, http://en.wikipedia.org/wiki/Polyadenylation (Feb. 20, 2007) (redacted).

Robbins, M.A., and Rossi, J.J. (2005) "Sensing the danger in RNA," Nature Med. 11:250-251.

Stein P., et al. (2003) "Transgenic RNAi in mouse oocytes: a simple and fast approach to study gene function" Dev Biol. 256(1):187-93.

Svoboda P., et al. (2004) "Lack of homologous sequence-specific DNA methylation in response to stable dsRNA expression in mouse oocytes" Nucleic Acids Res. 32(12):3601-6.

Svoboda P., et al. (2004) "RNAi and expression of retrotransposons MuERV-L and IAP in preimplantation mouse embryos" Dev Biol. 269(1):276-85.

Tatsuo, et al. (1997) "Comparison of three non-viral transfection methods for foreign gene expression in early chicken embryos in ovo," Biochemical and Biophysical Research Communications 230, 376-380.

Yamamoto, T., et al. (2002) "Double-stranded nef RNA interferes with human immunodeficiency virus type 1 replication," Microbio. Immunol. 46:809-817.

Yi C.E., et al. (2003) "Specific and potent RNA interference in terminally differentiated myotubes" J Biol Chem. 278(2):934-9.

Yu J., et al. (2004) "Transgenic RNAi-mediated reduction of MSY2 in mouse oocytes results in reduced fertility" Dev Biol. 268(1):195-206.

U.S. Appl. No. 09/287,632, filed Apr. 7, 1999, Waterhouse et al.

Klahre et al., (2002) "High molecular weight RNAs and small interfering RNAs induce systemic posttranscriptional gene silencing in plants," PNAS 99:11981-11986.

Metzlaff, M. et al., (1997) "RNA-Mediated RNA Degradation and Chalcone Synthase A Silencing in *Petunia*" Cell 88:845-854.

Opalinska et al., (2002) "Nucleic-Acid Therapeutics: Basic Principles and Recent Applications" Nature Reviews 1:503-514.

Sijen et al., Post-transcriptional gene-silencing RNAs on the attack or on the defense?, 2000, BioEssays, 22: 520-513.

Thomas, C.L., et al. (2001) "Size constraints for targeting post-transcriptional gene silencing and for RNA-directed methylation in *Nicotiana benthamiana* using a potato virus X vector," Plant J. 25(4):417-25.

Waterhouse, P.M., et al. (1998) "Virus resistance and gene silencing in plants can be induced by simultaneous expression of sense and antisense RNA," Proc. Natl. Acad. Sci. U.S.A. 95(23):13959-64.

Tieman et al. (1992) "An Antisense Pectin Methylesterase Gene Alters Pectin Chemistry and Soluble Solids in Tomato Fruit," Plant Cell 4:667-679.

Steinbrecher, R. (2002), "The CamV 35S Promoter, Government and Corporate Scientific Incompetence: Failure to assess the safety of GM crops," EcoNexus Briefing Dec. 2002.

Murfett et al. (1995), "Antisense suppression of S-Rnase expression in *Nicotiana* using RNA polymerase II- and III-transcribed gene constructs," Plant Molecular Biology 29:21-212.

Mishra et al. (1998), "Post-transcriptional silencing of pectin methylesterase gene in transgenic tomato fruits results from impaired pre-mRNA processing," The Plant Journal 14(5): 583-592.

Gatz, C. (1997), "Chemical Control of Gene Expression," Annu. Rev. Plant Physiol. Plant Mol. Bio. 48:89-108.

Scholthof et al. (1996), "Plant Virus Gene Vectors for Transient Expression of Foreign Proteins in Plants," Annu. Rev. of Phytopathol. 34:299-323.

Bourque et al. (1992), "Suppression of gene expression in plant cells utilizing antisense sequences transcribed by RNA polymerase III," Plant Molecular Biology 19:641-647.

Advisory Action issued Jun. 6, 2008 in connection with U.S. Appl. No. 11/179,504, filed Jul. 13, 2005.

Amendment submitted Feb. 15, 2008 in connection with U.S. Appl. No. 11/179,504, filed Jul. 13, 2005, including Exhibit A.

Amendment submitted Feb. 28, 2007 in connection with U.S. Appl. No. 11/179,504, filed Jul. 13, 2005.

Amendment submitted Oct. 18, 2007 in connection with U.S. Appl. No. 11/179,504, filed Jul. 13, 2005.

Communication submitted Sep. 2, 2008 in connection with U.S. Appl. No. 11/179,504, filed Jul. 13, 2005.

Amendment, including Exhibits A and B submitted May 21, 2008 in connection with U.S. Appl. No. 11/179,504, filed Jul. 13, 2005.

Interview Summary for Feb. 1, 2008 Interview in connection with U.S. Appl. No. 11/179,504, filed Jul. 13, 2005.

Office Action issued Apr. 18, 2007 in connection with U.S. Appl. No. 11/179,504, filed Jul. 13, 2005.

Office Action issued Dec. 20, 2007 in connection with U.S. Appl. No. 11/179,504, filed Jul. 13, 2005.

Office Action issued Jan. 30, 2007 in connection with U.S. Appl. No. 11/179,504, filed Jul. 13, 2005.

Office Action issued Jul. 30, 2008 in connection with U.S. Appl. No. 11/179,504, filed Jul. 13, 2005.

Office Action issued Mar. 21, 2008 in connection with U.S. Appl. No. 11/179,504, filed Jul. 13, 2005.

Office Action issued Nov. 10, 2008 in connection with U.S. Appl. No. 11/179,504, filed Jul. 13, 2005.

Preliminary Amendment submitted Jul. 13, 2005 in connection with U.S. Appl. No. 11/179,504, filed Jul. 13, 2005.

Amendment submitted May 11, 2009 in connection with U.S. Appl. No. 11/179,504, filed Jul. 13, 2005.

Final Office Action issued Aug. 13, 2009 in connection with U.S. Appl. No. 11/179,504, filed Jul. 13, 2005.

Response submitted Feb. 3, 2010 in connection with U.S. Appl. No. 11/179,504, filed Jul. 13, 2005.

Advisory Action issued Feb. 16, 2010 in connection with U.S. Appl. No. 11/179,504, filed Jul. 13, 2005.

Amendment as a Submission to Accompanying Request for Continued Examination submitted Apr. 19, 2010 in connection with U.S. Appl. No. 11/179,504, filed Jul. 13, 2005.

Office Action issued Dec. 16, 2010 in connection with U.S. Appl. No. 11/179,504, filed Jul. 13, 2005.

Amendment in Response to Dec. 16, 2010 Office Action submitted May 16, 2011 in connection with U.S. Appl. No. 11/179,504, filed Jul. 13, 2005.

Jul. 12, 2011 Final Office Action issued in connection with U.S. Appl. No. 11/179,504, filed Jul. 13, 2005.

Aug. 24, 2011 Response to Jul. 12, 2011 Final Office Action submitted in connection with U.S. Appl. No. 11/179,504, filed Jul. 13, 2005.

Sep. 2, 2011 Advisory Action issued in connection with U.S. Appl. No. 11/179,504, filed Jul. 13, 2005.

Sep. 9, 2011 Examiner Interview Summary Record issued in connection with U.S. Appl. No. 11/179,504, filed Jul. 13, 2005.
Sep. 19, 2011 Examiner Interview Summary Record issued in connection with U.S. Appl. No. 11/179,504, filed Jul. 13, 2005.
Nov. 11, 2011 Amendment in Response to Jul. 12, 2011 Final Office Action and Sep. 2, 2011 Advisory Action and Petition for a One-Month Extension of Time issued in connection with U.S. Appl. No. 11/179,504, filed Jul. 13, 2005.
Nov. 25, 2011 Advisory Action issued in connection with U.S. Appl. No. 11/179,504, filed Jul. 13, 2005.
Mar. 19, 2012 Notice of Allowance issued in connection with U.S. Appl. No. 11/179,504, filed Jul. 13, 2005.
Mar. 22, 2012 Summary of Examiner Interview filed in connection with U.S. Appl. No. 11/179,504, filed Jul. 13, 2005.
Notice of Reexamination Request Filing Date, issued Apr. 20, 2010 in connection with Reexamination Control No. 90/009,722, filed Apr. 12, 2010.
Notice of Assignment of Reexamination Request, issued Apr. 20, 2010 in connection with Reexamination Control No. 90/009,722, filed Apr. 12, 2010.
Order Granting Request for Ex Parte Reexamination, issued May 13, 2010 in connection with Reexamination Control No. 90/009,722, filed Apr. 12, 2010.
Office Action issued Sep. 30, 2010 in connection with Reexamination Control No. 90/009,722, filed Apr. 12, 2010.
Nov. 30, 2010 Amendment submitted in connection with Reexamination Control No. 90/009,722, filed Apr. 12, 2010.
Office Communication Issued Mar. 11, 2011 in connection with Reexamination Control No. 90/009,722, filed Apr. 12, 2010.
Supplemental Amendment and Statement of the Substance of Interview submitted Apr. 8, 2011 in connection with Reexamination Control No. 90/009,722, filed Apr. 12, 2010.
Jun. 22, 2011 Office Action issued in connection with Reexamination Control No. 90/009,722, filed Apr. 12, 2010.
Aug. 22, 2011 Reply to Jun. 22, 2011 Office Action submitted in connection with Reexamination Control No. 90/009,722, filed Apr. 12, 2010.
Sep. 14, 2011 Examiner Interview Summary Record issued in connection with Reexamination Control No. 90/009,722, filed Apr. 12, 2010.
Oct. 12, 2011 Statement of the Substance of an Interview and Supplemental Amendment submitted in connection with Reexamination Control No. 90/009,722, filed Apr. 12, 2010.
Oct. 12, 2011 Amended Claims submitted in the Oct. 12, 2011 Statement of the Substance of an Interview and Supplemental Amendment, which were allowed in connection with Reexamination Control No. 90/009,722, filed Apr. 12, 2010.
Dec. 6, 2011 Notice of Intent to Issue Ex Parte Reexamination Certificate issued in connection with Reexamination Control No. 90/009,722, filed Apr. 12, 2012.
Jan. 26, 2012 Notice of Opposition filed in connection with European Patent No. 1068311 by Potter Clarkson on behalf of "Strawman Limited".
Jan. 27, 2012 Notice of opposition filed in connection with European Patent No. 1068311 by Carnegie Institution of Washington and University of Massachusetts.
Jan. 23, 2012 Notice of Opposition filed in connection with European Patent No. 1068311 by BASF SE.
Jan. 26, 2012 Notice of Opposition filed in connection with European Patent No. 1068311 by Syngenta International AG.
Feb. 3, 2012 Third Party Observations under Article 115 EPC filed on behalf of Commonwealth Scientific and Industrial Research Organisation and Bayer CropScience N.V. against European Patent Application No. 98964202.0.
U.S. Appl. No. 13/290,609, filed Nov. 7, 2011, Graham et al.
Pending claims for U.S. Appl. No. 10/282,996, filed Oct. 30, 2002.
Pending claims for U.S. Appl. No. 10/283,190, filed Oct. 30, 2002.
Pending claims for U.S. Appl. No. 10/283,267, filed Oct. 30, 2002.
Pending claims for U.S. Appl. No. 11/826,385, filed Jul. 13, 2007.
Pending claims for U.S. Appl. No. 11/905,368, filed Sep. 28, 2007.
Pending claims for U.S. Appl. No. 11/905,449, filed Oct. 1, 2007.
Amendment submitted Apr. 7, 2006 in connection with U.S. Appl. No. 10/152,808, filed May 23, 2002.

Amendment submitted Jul. 13, 2005, including Terminal Disclaimer in connection with U.S. Appl. No. 10/152,808, filed May 23, 2002.
Amendment submitted Oct. 22, 2004 in connection with U.S. Appl. No. 10/152,808, filed May 23, 2002.
Notice of Allowability, including Examiner's Statement of Reasons for Allowance issued Jul. 11, 2006 in connection with U.S. Appl. No. 10/152,808, filed May 23, 2002.
Office Action issued Jan. 13, 2005 in connection with U.S. Appl. No. 10/152,808, filed May 23, 2002.
Office Action issued Oct. 7, 2005 in connection with U.S. Appl. No. 10/152,808, filed May 23, 2002.
Office Action issued Sep. 22, 2004 in connection with U.S. Appl. No. 10/152,808, filed May 23, 2002.
Preliminary Amendment submitted May 23, 2002 in connection with U.S. Appl. No. 10/152,808, filed May 23, 2002.
Amendment submitted Jun. 12, 2008 in connection with U.S. Appl. No. 11/593,056, filed Nov. 6, 2006.
Communication submitted Sep. 21, 2007 in connection with U.S. Appl. No. 11/593,056, filed Nov. 6, 2006.
Office Action issued Dec. 12, 2007 in connection with U.S. Appl. No. 11/593,056, filed Nov. 6, 2006.
Office Action issued Jul. 24, 2007 in connection with U.S. Appl. No. 11/593,056, filed Nov. 6, 2006.
Office Action issued Sep. 12, 2008 in connection with U.S. Appl. No. 11/593,056, filed Nov. 6, 2006.
Preliminary Amendment submitted Nov. 6, 2006 in connection with U.S. Appl. No. 11/593,056, filed Nov. 6, 2006.
Amendment submitted Dec. 19, 2008 in connection with U.S. Appl. No. 10/571,384, filed Jun. 1, 2006.
Amendment submitted Feb. 8, 2007 in connection with U.S. Appl. No. 10/571,384, filed as a §371 national stage of PCT International Application No. PCT/AU2004/01237.
Office Action issued Jan. 15, 2009 in connection with U.S. Appl. No. 10/571,384, filed Jun. 1, 2006.
Office Action issued Jun. 19, 2008 in connection with U.S. Appl. No. 10/571,384, filed Jun. 1, 2006.
Preliminary Amendment submitted Mar. 10, 2006 in connection with U.S. Appl. No. 10/571,384, filed as a §371 national stage of PCT International Application No. PCT/AU2004/01237.
Abstract in English for European Patent Publication No. 0560156, published Sep. 15, 1993, retrieved from espacenet on Apr. 22, 2008.
International Preliminary Report on Patentability issued by the International Bureau of WIPO on Mar. 13, 2006 in connection with International Application No. PCT/AU2004/001237.
International Search Report issued by the International Searching Authority (ISA/AU) on Oct. 20, 2004 in connection with International Application No. PCT/AU2004/001237.
Partial European Search Report issued Nov. 2, 2007 in connection with European Patent Application No. 07008204.5.
Written Opinion of the International Searching Authority issued by the International Preliminary Examining Authority (IPEA/AU) on Oct. 20, 2004 in connection with International Application No. PCT/AU2004/001237.
Examination Report issued May 10, 2010 in connection with European Patent Application No. 02748428.6.
Communication in Response to Dec. 30, 2009 Office Action, Petition for Three-Month Extension of Time and Supplemental Information Disclosure Statement submitted Jun. 30, 2010 in connection with U.S. Appl. No. 10/482,888, filed Jun. 14, 2004.
Sep. 22, 2010 Final Office Action issued in connection with U.S. Appl. No. 10/482,888, filed Jun. 14, 2004.
Feb. 22, 2011 Amendment submitted in connection with U.S. Appl. No. 10/482,888, filed Jun. 14, 2004.
Apr. 18, 2011 Office Action issued in connection with U.S. Appl. No. 10/482,888, filed Jun. 14, 2004.
Sep. 19, 2011 Response to Apr. 18, 2011 Office Action submitted in connection with U.S. Appl. No. 10/482,888, filed Jun. 14, 2004.
Oct. 27, 2011 Notice of Allowance issued in connection with U.S. Appl. No. 10/482,888, filed Jun. 14, 2004.
Amendment submitted Mar. 12, 2009 in connection with U.S. Appl. No 11/593,056, filed Nov. 6, 2006.
Office Action issued Jun. 24, 2009 in connection with U.S. Appl. No. 11/593,056, filed Nov. 6, 2006.

Amendment submitted Dec. 23, 2009 in connection with U.S. Appl. No. 11/593,056, filed Nov. 5, 2006.
Final Office Action issued Mar. 24, 2010 in connection with U.S. Appl. No. 11/593,056, filed Nov. 6, 2006.
Request for Ex Parte Reexamination of U.S. Patent No. 7,138,565, including Exhibits A-K, submitted Apr. 9, 2010.
Jan. 26, 2012 Non-Final Notice of Reasons for Rejection mailed on Jan. 31, 2012 in connection with Japanese Patent Application No. 2000-543598, including English language translation.
English language claims which are presently pending in Japanese Patent Application No. 2000-543598.
Amendment submitted Jul. 15, 2009 in connection with U.S. Appl. No. 10/571,384, filed Jun. 1, 2006.
Office Action issued Oct. 1, 2009 in connection with U.S. Appl. No. 10/571,384, filed Jun. 1, 2006.
Extended European Search Report issued Mar. 14, 2011 in connection with European Patent Application No. 10184533.7.
Supplementary European Search Report issued Feb. 12, 2010 in connection with European Patent Application No. 04761272.
Allen et al. (2007) "Development of strategies for conditional RNA interference," J. Gene Med. 9: 287-298.
Becker, W.M., and Deemer, D.W. (1991) "The World of the Cell," pp. 474 to 477 (The Benjamin/Cummings Publishing Company, Inc., Redwood City, California, pub.).
Beck, J., et al. (1995), "Efficient hammerhead ribozyme-mediated cleavage of the structured hepatitis B virus encapsidation signal in vitro and in cell extracts, but not in intact cells," Nucleic Acids Research, vol. 23, No. 24: 4954-4962.
Berns, K., et al. (2004) "A large-scale RNAi screen in human cells identifies new components of the p53 pathway," Nature 428:431-437.
Bramlage et al. (1998) "Designing Ribozymes for the Inhibition of Gene Expression," TIBTECH, 16:434-438.
Covey et al. (1997) "Plants Combat Infection by Gene Silencing," Nature 385:781-782.
Davis, BM et al. (1997) "Expansion of a CUG trinucleotide repeat in the 3' untranslated region of myotonic dystrophy protein kinase transcripts results in nuclear retention of transcripts," Proc. Natl. Acad. Sci. USA 94:7388-7393.
De Angelis, F.G., et al. (2002), "Chimeric snRNA molecules carrying antisense sequences against the splice junctions of exon 51 of the dystrophin pre-mRNA induce exon skipping and restoration of a dystrophin synthesis in delta 48-50 DMD cells," PNAS, vol. 99, No. 14: 9456-9461.
Doelling JH and Pikaard CS (1995) "The minimal ribosomal RNA gene promoter of *Arabidopsis thaliana* includes a critical element at the transcription initiation site" Plant J. Nov.;8(5):683-92.
Doelling et al. (1995), The Plant Journal vol. 8:683-692.
Donahue C.P. et al. (1997) "Kinetics of Hairpin Ribozyme Cleavage in Yeast" RNA 3:961-973.
Eckner at al. (1991) "Mature mRNA 3' End Formation Stimulates RNA Export From the Nucleus," EMBO J. 10:3513-3522.
Egli and Braus (1994) "Uncoupling of mRNA 3' Cleavage and Polyadenylation by Expression of a Hammerhead Ribozyme in Yeast," J. Biol. Chem. 269:27378-27383.
Giering J.C., et al. (2008) "Expression of shRNA from a tissue-specific pol II promoter is an effective and safe RNAi therapeutic," Mol Ther. 16(9):1630-6.
Hamilton, A.J., et al. (1998) "A Transgene with Repeated DNA Causes High Frequency, Post-Transcriptional Suppression of ACC-Oxidase Gene Expression in Tomato" The Plant Journal 15(6): 737-746.
Haseloff et al. (1988) "Simple RNA Enzymes With New and Highly Specific Endonuclease Activities," Nature 334:585-591.
Heard, D.J., et al. (1995) "An upstream U-snRNA gene-like promoter is required for transcription of the *Arabidopsis thaliana* 7SL RNA gene," Nucleic Acids Res. 23(11):1970-6.
Image of U6 snoRNA secondary structure retrieved from http://gene.fudan.sh.cn/snoRNASecStruct/Box%20C&D/Homo%20sapiens/U16_ss_p0001.jpg on Sep. 17, 2009.
Itaya A et al., (2001) "*Potato spindle tuber viroid* as Inducer of RNA Silencing in Infected Tomato," Mol. Plant Microbe In. 14(11):1332-1334.

Lee, K.Y., et al., (1997) "Post-transcriptional Gene Silencing of ACC Synthase in Tomato Results from Cytoplasmic RNA Degradation" The Plant Journal 12(5): 1127-1137.
Liu, Z. et al. (1994) "An Efficient New Method to Inhibit Gene Expression" Molecular Biotechnology 2:107, 109-118.
Liu, Z. et al. (1994) "Targeted Nuclear Antisense RNA Mimics Natural Antisense-Induced Degradation of Polyoma Virus Early RNA" PNAS 91:4258-4262.
Marshallsay et al. (1992) "Characterization of the U3 and U6 snRNA genes from wheat: U3 snRNA genes in monocot plants are transcribed by RNA polymerase III," Plant Molecular Biology, vol. 19, pp. 973-998.
Miller et al. (1991) "A Satellite RNA of Barley Yellow Dwarf Virus Contains a Novel Hammerhead Structure in the Self-Cleavage Domain" Virology 183:711-720.
Ngo, V.N., et al. (2006) "A loss-of-function RNA interference screen for molecular targets in cancer," Nature 441:106-110.
Paddison, P.J., et al. (2002) "Stable suppression of gene expression by RNAi in mammalian cells," Proc. Natl. Acad. Sci. U.S.A. 99:1443-1448.
Paddison, P.J., et al. (2004) "A resource for large-scale RNA interference-based screens in mammals" Nature 428:427-431.
Papefthimiou et al. (2001) "Replicating potato spindle tuber viroid RNA is accomplished by short RNA fragments that are characteristic of post-transcriptional gene silencing," Nucleic Acids Res. 29(11):2395-2400.
Ramezani et al (1997) "Inhibition of HIV-1 replication by retroviral vectors expressing monomeric and multimeric hammerhead ribozymes" Gene Therapy 4 861-867.
Rubio et al., (1999) "Broad Spectrum Protection Against Tombusviruses Elicited by Defective Interfering RNAs in Transgenic Plants" J. Virology 73:5070-5078.
Ruiz F, Vayssié L, Klotz C, Sperling L, Madeddu L. (1998) "Homology-dependent gene silencing in Paramecium," Mol Biol Cell. 9(4):931-43.
Sambrook, J., et al. "Molecular Cloning. A Laboratory Model," 2nd ed., pp. 16.1 to 16.81, Cold Spring Harbor Laboratory Press, Cold Spring Harbor, New York, pub., (1989).
Sanchez Alvarado A, Newmark PA. (1999) "Double-stranded RNA specifically disrupts gene expression during planarian regeneration," Proc Natl Acad Sci U S A. 96(9):5049-54.
Silva, J.M., et al. (2005) "Second-generation shRNA libraries covering the mouse and human genomes" Nat Genet. 37:1281-1288.
Song J., et al. (2004) "Poly(U) and polyadenylation termination signals are interchangeable for terminating the expression of shRNA from a pol II promoter," Biochem Biophys Res Commun. 323(2):573-8.
Suter, D., et al. (1999), "Double-target antisense U7 snRNAs promote efficient skipping of an aberrant exon in three human beta-thalassemic mutations," Human Molecular Genetics, vol. 8: 2415-2423.
Vaish et al. (1998) "Recent Developments in the Hammerhead Ribozyme Field" Nucleic Acids Res. 26:5237-5242.
van Eldik et al. (1998) "Silencing of β-1,3-glucanase Genes in Tobacco Correlates With an Increased Abundance of RNA Degradation Intermediates," Nucleic Acids Res 26:5176-5181.
van Houdt et al. (1997) "Post-Transcriptional Silencing of a Neomycin Phosphotransferase II Transgene Correlates With the Accumulation of Unproductive RNAs and With Increased Cytosine Methylation of 3' Flanking Regions," Plant Journal 12:379-392.
Waibel et al. (1990) "RNA polymerase specificity of transcription of *Arabidopsis* U snRNA genes determined by promoter element spacing," Letters to Nature, vol. 346, pp. 199-202).
Waibel et al., (1990) "U6 snRNA genes of *Arabidopsis* are transcribed by RNA polymerase III but contain the same two upstream promoter elements as RNA polymerase II transcribed U-snRNA genes," Nucleic Acids Research, vol. 18, No. 12, pp. 3451-3458.
Welch P.J. et al. (1998) "Expression of Ribozymes in Gene Transfer Systems to Modulate Target RNA Levels" Current Opinion in Biotechnology 9:486-496.
Wesley SV et al. (2001) "Construct design for efficient, effective and high-throughput gene silencing in plants," Plant J. 27(6):581-590.

Wolff et al. (1995) "Mutational analysis of human U6 RNA: stabilizing the intramolecular helix blocks the spliceosomal assembly pathway," Biochim. Biophys. Acta 1263: 39-44.

Zhao, Y. et al. (2001) "Use of a vector based on Potato Virus X in a whole plant assay to demonstrate nuclear targeting of Potato spindle tuber viroid," J. Gen. Virol. 82:1491-1497.

U.S. Appl. No. 13/545,604, filed Jul. 10, 2012 (Whyard et al.).

Sep. 5, 2012 Office Action, issued in connection with U.S. Appl. No. 13/290,609.

Sep. 28, 2012 Office Action, issued in connection with U.S. Appl. No. 12/798,247.

European Search Report issued for EP05016726, completed on Mar. 8, 2006.

Examination Report issued Mar. 4, 2011 in connection with European Application No. 04015041.9.

Examination Report issued Mar. 4, 2011 in connection with European Application No. 05013010.3.

Advisory Action issued Feb. 15, 2002 in connection with U.S. Appl. No. 09/100,812, filed Jun. 19, 1998.

Amendment submitted Apr. 29, 2002 in connection with U.S. Appl. No. 09/100,812, filed Jun. 19, 1998.

Amendment submitted Nov. 10, 2000 in connection with U.S. Appl. No. 09/100,812, filed Jun. 19, 1998.

Amendment submitted Nov. 12, 2001 in connection with U.S. Appl. No. 09/100,812, filed Jun. 19, 1998.

Amendment submitted Oct. 17, 2002 in connection with U.S. Appl. No. 09/100,812, filed Jun. 19, 1998.

Amendment submitted Sep. 26, 2002 in connection with U.S. Appl. No. 09/100,812, filed Jun. 19, 1998.

Communication submitted Apr. 3, 2000 in connection with U.S. Appl. No. 09/100,812, filed Jun. 19, 1998.

Declaration of Kenneth Clifford Reed submitted Sep. 26, 2002 in connection with U.S. Appl. No. 09/100,812, filed Jun. 19, 1998.

Declaration of Michael Wayne Graham submitted Apr. 29, 2002 in connection with U.S. Appl. No. 09/100,812, filed Jun. 19, 1998.

Declaration of Michael Wayne Graham submitted Sep. 26, 2002 in connection with U.S. Appl. No. 09/100,812, filed Jun. 19, 1998.

Interview Summary issued Jan. 11, 2001 in connection with U.S. Appl. No. 09/100,812, filed Jun. 19, 1998.

Interview Summary issued Sep. 18, 2002 in connection with U.S. Appl. No. 09/100,812, filed Jun. 19, 1998.

Notice of Allowability, including Examiner's Amendment and Examiner's Statement of Reasons for Allowance issued Nov. 20, 2002 in connection with U.S. Appl. No. 09/100,812, filed Jun. 19, 1998.

Office Action issued Dec. 2, 1999 in connection with U.S. Appl. No. 09/100,812, filed Jun. 19, 1998.

Office Action issued Feb. 12, 2001 in connection with U.S. Appl. No. 09/100,812, filed Jun. 19, 1998.

Office Action issued May 10, 2000 in connection with U.S. Appl. No. 09/100,812, filed Jun. 19, 1998.

Amendment and Request for Continued Examination submitted Jan. 7, 2009 in connection with U.S. Appl. No. 10/346,853, filed Jan. 17, 2003.

Amendment submitted Apr. 16, 2008 in connection with U.S. Appl. No. 10/346,853, filed Jan. 17, 2003.

Amendment submitted Dec. 27, 2006 in connection with U.S. Appl. No. 10/346,853, filed Jan. 17, 2003.

Amendment submitted Feb. 22, 2007, in connection with U.S. Appl. No. 10/346,853, filed Jan. 17, 2003.

Amendment submitted Jan. 17, 2003 in connection with U.S. Appl. No. 10/346,853, filed Jan. 17, 2003.

Amendment submitted Mar. 25, 2003 in connection with U.S. Appl. No. 10/346,853, filed Jan. 17, 2003.

Amendment submitted Oct. 17, 2007 in connection with U.S. Appl. No. 10/346,853, filed Jan. 17, 2003.

Communication submitted Aug. 2, 2005 in connection with U.S. Appl. No. 10/346,853, filed Jan. 17, 2003.

Decision on Petition to Make Special Under 37 CFR 1.102(d) submitted Jul. 27, 2004 in connection with U.S. Appl. No. 10/346,853, filed Jan. 17, 2003.

Interview Summary issued Dec. 11, 2007 in connection with U.S. Appl. No. 10/346,853, filed Jan. 17, 2003.

Notice of Improper Request for Continued Examination issued Oct. 29, 2008 in connection with U.S. Appl. No. 10/346,853, filed Jan. 17, 2003.

Office Action issued Apr. 17, 2007 in connection with U.S. Appl. No. 10/346,853, filed Jan. 17, 2003.

Office Action issued Jan. 16, 2008 in connection with U.S. Appl. No. 10/346,853, filed Jan. 17, 2003.

Office Action issued Jul. 22, 2005 in connection with U.S. Appl. No. 10/346,853, filed Jan. 17, 2003.

Office Action issued Jul. 7, 2008 in connection with U.S. Appl. No. 10/346,853, filed Jan. 17, 2003.

Office Action issued Jun. 27, 2006 in connection with U.S. Appl. No. 10/346,853, filed Jan. 17, 2003.

Petition for Unintentionally Delayed Claim of Priority under 37 CFR §1.78(a)(3) submitted Dec. 27, 2006 in connection with U.S. Appl. No. 10/346,853, filed Jan. 17, 2003.

Petition to Make Special Under 37 CFR 1.102(d) submitted Jul. 27, 2004 in connection with U.S. Appl. No. 10/346,853, filed Jan. 17, 2003.

Request for Continued Examination submitted Oct. 7, 2008 in connection with U.S. Appl. No. 10/346,853, filed Jan. 17, 2003.

Amendment submitted Apr. 15, 2008 in connection with U.S. Appl. No. 10/759,841, filed Jan. 15, 2004.

Amendment submitted Dec. 29, 2006 in connection with U.S. Appl. No. 10/759,841, filed Jan. 15, 2004.

Amendment submitted Feb. 21, 2007, in connection with U.S. Appl. No. 10/759,841, filed Jan. 15, 2004.

Amendment submitted Oct. 25, 2007 in connection with U.S. Appl. No. 10/759,841, filed Jan. 15, 2004.

Amendment submitted Oct. 31, 2006 in connection with U.S. Appl. No. 10/759,841, filed Jan. 15, 2004.

Amendment submitted Oct. 9, 2008 in connection with U.S. Appl. No. 10/759,841, filed Jan. 15, 2004.

Interview Summary for Dec. 22, 2008 in connection with U.S. Appl. No. 10/759,841, filed Jan. 15, 2004.

Interview Summary for Feb. 12, 2009 Interview in connection with U.S. Appl. No. 10/759,841, filed Jan. 15, 2004.

Interview Summary issued Dec. 11, 2007 in connection with U.S. Appl. No. 10/759,841, filed Jan. 15, 2004.

Office Action issued Apr. 25, 2007 in connection with U.S. Appl. No. 10/759,841, filed Jan. 15, 2004.

Office Action issued Jan. 22, 2009 in connection with U.S. Appl. No. 10/759,841, filed Jan. 15, 2004.

Office Action issued Jan. 6, 2009 in connection with U.S. Appl. No. 10/759,841, filed Jan. 15, 2004.

Office Action issued Jan. 8, 2008 in connection with U.S. Appl. No. 10/759,841, filed Jan. 15, 2004.

Office Action issued Jul. 31, 2006 in connection with U.S. Appl. No. 10/759,941, filed Jan. 15, 2004.

Office Action issued Jul. 9, 2008 in connection with U.S. Appl. No. 10/759,841, filed Jan. 15, 2004.

Office Action issued Nov. 29, 2006 in connection with U.S. Appl. No. 10/759,841, filed Jan. 15, 2004.

Preliminary Amendment submitted Jan. 15, 2004 in connection with U.S. Appl. No. 10/759,841, filed Jan. 15, 2004.

Amendment and Request for Continued Examination Submitted Sep. 5, 2008 in connection with U.S. Appl. No. 10/821,726, filed Apr. 8, 2004.

Amendment submitted Aug. 2, 2007 in connection with U.S. Appl. No. 10/821,726, filed Apr. 8, 2004.

Amendment submitted Dec. 14, 2006 in connection with U.S. Appl. No. 10/821,726, filed Apr. 8, 2004.

Amendment submitted Nov. 14, 2005 in connection with U.S. Appl. No. 10/821,726, filed Apr. 6, 2004.

Amendment submitted Nov. 30, 2006 in connection with U.S. Appl. No. 10/821,726, filed Apr. 8, 2004.

Amendment submitted Oct. 31, 2007 in connection with U.S. Appl. No. 10/921,726, filed Apr. 8, 2004.

Amendment, including Exhibits A to C submitted Sep. 5, 2008 in connection with U.S. Appl. No. 10/821,726, filed Apr. 8, 2004.

Communication issued Apr. 2, 2007 in connection with U.S. Appl. No. 10/821,726, filed Apr. 8, 2004.

Decision on Petition to Make Special Under 37 CFR 1.102(d) issued Sep. 30, 2004 in connection with U.S. Appl. No. 10/821,726, filed Apr. 8, 2004.

Office Action issued May 30, 2006 in connection with U.S. Appl. No. 10/821,726, filed Apr. 8, 2004.

Office Action issued Nov. 3, 2008 in connection with U.S. Appl. No. 10/821,726, filed Apr. 8, 2004.

Office Action issued Nov. 6, 2007 in connection with U.S. Appl. No 10/821,726, filed Apr. 8, 2004.

Office Action issued Oct. 14, 2005 in connection with U.S. Appl. No. 10/821,726, filed Apr. 8, 2004.

Office Action issued Sep. 4, 2009 in connection with U.S. Appl. No. 10/821,726, filed Apr. 8, 2004.

Petition to Make Special Under 37 CFR 1.102(d) submitted Jul. 28, 2004 in connection with U.S. Appl. No. 10/821,726, filed Apr. 8, 2004.

Preliminary Amendment submitted Apr. 8, 2004 in connection with U.S. Appl. No. 10/821,726, filed Apr. 8, 2004.

Request to Correct Inventorship Under 37 C.F.R. §1.48(a) submitted Dec. 12, 2007 in connection with U.S. Appl. No. 10/821,726, filed Apr. 8, 2004.

Amendment submitted Dec. 22, 2006, in connection with U.S. Appl. No. 11/180,928, filed Jul. 13, 2005.

Amendment submitted Jun. 6, 2008 in connection with U.S. Appl. No. 11/180,928, filed Jul. 13, 2005.

Amendment submitted Oct. 17, 2007 in connection with U.S. Appl. No. 11/180,928, filed Jul. 13, 2005.

Communication submitted Mar. 6, 2007 in connection with U.S. Appl. No. 11/180,928, filed Jul. 13, 2005.

Interview Summary issued Dec. 11, 2007 in connection with U.S. Appl. No. 11/180,928, filed Jul. 13, 2005.

Office Action issued Apr. 17, 2007 in connection with U.S. Appl. No. 11/180,928, filed Jul. 13, 2005.

Office Action issued Feb. 6, 2007 in connection with U.S. Appl. No. 11/180,928, filed Jul. 13, 2005.

Office Action issued Jan. 8, 2008 in connection with U.S. Appl. No. 11/180,928, filed Jul. 13, 2005.

Office Action issued Oct. 31, 2006 in connection with U.S. Appl. No. 11/180,928, filed Jul. 13, 2005.

Preliminary Amendment submitted Jul. 13, 2005 in connection with U.S. Appl. No. 11/180,928, filed Jul. 13, 2005.

Request to Correct Inventorship Under 37 C.F.R. §1.48(a) filed Oct. 17, 2007 in connection with U.S. Appl. No. 11/180,928, filed Jul. 13, 2005.

Appeal No. T1491/05-3308, issued Apr. 24, 2007, Technical Board of Appeal of the European Patent Office.

Final Office Action issued May 15, 2009 in connection with U.S. Appl. No. 10/346,853, filed Jan. 17, 2003.

Supplemental Amendment to Oct. 15, 2009 Amendment Filed in Response to May 15, 2009 Final Office Action, Summary of Examiner Interviews, and Supplemental Information Disclosure Statement submitted Dec. 21, 2009 in connection with U.S. Appl. No. 10/346,853, filed Jan. 17, 2003.

Amendment in Response to May 15, 2009 Final Office Action as a Submission to Accompanying Request for Continued Examination submitted Oct. 15, 2009 in connection with U.S. Appl. No. 10/346,853, filed Jan. 17, 2003.

Office Action issued Apr. 15, 2010 in connection with U.S. Appl. No. 10/346,853, filed Jan. 7, 2003.

Jan. 26, 2011 Office Action issued in connection with U.S. Appl. No. 10/346,853, filed Jan. 17, 2003.

Amendment in Response to Jan. 26, 2011 Office Action submitted Feb. 16, 2011 in connection with U.S. Appl. No. 10/346,853, filed Jan. 17, 2003.

Office Action issued Apr. 19, 2011 in connection with U.S. Appl. No. 10/346,853, filed Jan. 7, 2003.

May 13, 2011 Response to Apr. 19, 2011 Office Action submitted in connection with U.S. Appl. No. 10/346,853, filed Jan. 7, 2003.

Aug. 4, 2011 Notice of Allowance issued in connection with U.S. Appl. No. 10/346,853, filed Jan. 7, 2003.

Amendment submitted Sep. 24, 2009 in connection with U.S. Appl. No. 10/759,841, filed Jan. 15, 2004.

Supplemental Amendment to Sep. 24, 2009 Amendment, Summary of Dec. 17, 2009 Examiner Interview, and Supplemental Information Disclosure Statement submitted Dec. 21, 2009 in connection with U.S. Appl. No. 10/759,841, filed Jan. 15, 2004.

Office Action issued Mar. 9, 2010 in connection with U.S. Appl. No. 10/759,841, filed Jan. 15, 2004.

Examiner Interview Summary Record (PTOL-413) issued Apr. 15, 2010 in connection with U.S. Appl. No. 10/759,841, filed Jan. 15, 2004.

Jun. 15, 2010 Amendment in Response to Mar. 9, 2010 Office Action, Summary of Apr. 8, 2010 Examiner Interview, and Supplemental Information Disclosure Statement submitted in connection with U.S. Appl. No. 10/759,841, filed Jan. 15, 2004.

Jun. 15, 2010 Supplemental Information Disclosure Statement submitted in connection with U.S. Appl. No. 10/759,841, filed Jan. 15, 2004.

Sep. 1, 2010 Notice of Allowance issued in connection with U.S. Appl. No. 10/759,841, filed Jan. 15, 2004.

Dec. 9, 2010 Petition to Withdraw from Issue Pursuant to 37 C.F.R. 1.313(c), including a Request for Continued Examination, Amendment, and Supplemental Information Disclosure Statement submitted in connection with U.S. Appl. No. 10/759,841, filed Jan. 15, 2004.

Mar. 30, 2011 Office Action issued in connection with U.S. Appl. No. 10/759,841, filed Jan. 15, 2004.

Notice to the applicant regarding a non-compliant or non-responsive amendment issued Sep. 4, 2009 in connection with U.S. Appl. No. 10/821,726, filed Apr. 8, 2004.

Nov. 2, 2010 Communication from the UK Intellectual Property Office in connection with GB 2353282, including a Request for Revocation Under s72 UK Patent Act 1977 filed Sep. 29, 2010 and amended Request for Revocation Under s72 UK Patent Act 1977 filed Oct. 28, 2010.

Counter-Statement of Commonwealth Scientific and Industrial Research Organisation in connection with Application Under s72 UK Patent Act 1977 to Revoke Patent No. GB 2353282.

Amendment submitted May 4, 2009 in connection with U.S. Appl. No. 10/821,726, filed Apr. 8, 2004.

Communication in response to a non-compliant or non-responsive amendment submitted Oct. 5, 2009 in connection with U.S. Appl. No. 10/821,726, filed Apr. 8, 2004.

Supplemental Amendment to May 4, 2009 Amendment Filed in Response to Nov. 3, 2008 Office Action and Supplemental Information Disclosure Statement submitted Oct. 7, 2009 in connection with U.S. Appl. No. 10/821,726, filed Apr. 8, 2004.

Office Action issued Mar. 9, 2010 in connection with U.S. Appl. No. 10/821,726, filed Apr. 8, 2004.

Amendment and Supplemental Information Disclosure Statement as a Submission Accompanying a Request for Continued Examination filed Dec. 15, 2010 in connection with U.S. Appl. No. 10/821,726, filed Apr. 8, 2004.

Office Action issued Mar. 22, 2011 in connection with U.S. Appl. No. 10/821,726, filed Apr. 8, 2004.

Amendment and Supplemental Information Disclosure Statement filed Jun. 22, 2011 in connection with U.S. Appl. No. 10/821,726, filed Apr. 8, 2004.

Supplemental Information Disclosure Statement filed Jun. 22, 2011 in connection with U.S. Appl. No. 10/821,726, filed Apr. 8, 2004.

Jul. 25, 2011 Notice of Allowance issued in connection with U.S. Appl. No. 10/821,726, filed Apr. 8, 2004.

Amendment in Response to Mar. 30, 2011 Office Action and Supplemental Information Disclosure Statement submitted Jun. 28, 2011 in connection with U.S. Appl. No. 10/759,841, filed Jan. 15, 2004.

Aug. 9, 2011 Final Office Action issued in connection with U.S. Appl. No. 10/759,841, filed Jan. 15, 2004.

Aug. 10, 2011 Response to Aug. 9, 2011 Final Office Action submitted in connection with U.S. Appl. No. 10/759,841, filed Jan. 15, 2004.

Aug. 25, 2011 Notice of Allowance issued in issued in connection with U.S. Appl. No. 10/759,841, filed Jan. 15, 2004.

Assaad, F.E., et al. (1993) "Epigenetic Repeat-Induced Gene Silencing (RIGS) in *Arabidopsis*" Plant Molecular Biology 22(6):1067-1085.

Balandin, T., and Castresana, C. (1997) "Silencing of a β-1-3-glucanase Transgene is Overcome During Seed Formation" Plant Molecular Biology 34(1):125-137.

Baulcombe, D.C. (1996) "RNA as a Target and an Initiator of Post-Transcriptional Gene Silencing in Transgenic Plants," Plant Molecular Biology 32(1-2): 79-88.

Bevec et al. (1994) "Constitutive expression of chimeric Neo-Rev response element transcripts suppresses HIV-1 replication in human CD4+ T lymphocytes" Human Gene Therapy 5: 193-201.

Bingham, P.M. (1997) "Cosuppression Comes to the Animals" Cell 90(3): 385-387.

Brigneti, Gianinna et al. (1998) "Viral pathogenicity determinants are suppressors of transgene silencing in Nicotiana benthamiana" EMBO Journal, 17(22): 6739-6746.

Cameron et al. (1989) "Specific Gene Supression by Engineered Ribozymes in Monkey Cells" Proc. Natl. Acad. Sci. USA 86:9139.

Chuah et al. (1994) "Inhibition of human immunodeficiencyvirus Type-1 by retroviral vectors expressing antisense-TAR" Human Gene Therapy 5: 1467-1475.

Clemens MJ. (1997) "PKR—a protein kinase regulated by double-stranded RNA," Int J Biochem Cell Biol. 29(7):945-9.

Cogoni, C., et al. (1994) "Suppression of Gene Expression by Homologous Transgenes" Antonie Van Leeuwenhoek 65(3): 205.

Cogoni, C., et al. (1996) "Transgene Silencing of the al-1 Gene in Vegetative Cells of Neurospora is Mediated by a Cytoplasmic Effector and Does not Depend on DNA-DNA Interactions or DNA Methylation" The EMBO Journal 15(12): 3153-3163.

Cogoni, C., et al. (1997) "Isolations of Quelling-Defective (qde) Mutants Impaired in Posttranscriptional Transgene-Induced Gene Silencing in Neurospora crassa" PNAS 94 (19): 10233-10238.

Cogoni, Carlo et al. (1999) "Gene silencing in Neurospora crassa requires a protein homologous to RNA-dependent RNA polymerase" Nature, vol. 399: 166-169.

Cogoni, Carlo et al. (1999) "Posttranscriptional Gene Silencing in Neurospora by a RecQ DNA Helicase" Science, 286: 2342-2344.

Courtney-Gutterson, N., et al. (1994) "Modification of flower color in florist's chrysanthemum: production of a white-flowering variety through molecular genetics," Biotechnology (N.Y.) 12(3): 268-271.

Dalmay, Tames, et al. (2000) "An RNA-Dependent RNA Polymerase Gene in Arabidopsis Is Required for Posttranscriptional Gene Silencing Mediated by a Transgene but Not by a Virus" Cell, 101: 543-553.

Davenloo, P. et al. (1984) "Cloning and expression of the gene for bacteriophage T7 RNA polymerase," PNAS vol. 81, pp. 2035-2039.

de Carvalho F., et al. (1992) "Suppression of β-1,3-glucanase Transgene Expression in Homozygous Plants" The EMBO Journal 11(7): 2595-2602.

de Carvalho Niebel, F., et al. (1995) "Post-transscriptional Cosuppression of β-1,3-glucanase Genes Does Not Effect Accumulation of Transgene Nuclear mRNA" The Plant Cell 7(3): 347-358.

De Lange, P., et al. (1995) "Suppression of Flavonoid Flower Pigmentation Genes in Petunia hybrida by the Introduction of Antisense and Sense Genes" Current Topics in Microbiology and Immunology 197: 57-75.

Depicker, A., et al. (1997) "Post-transcriptional Gene Silencing in Plants" Current Opinion in Cell Biology 9(3): 373-382.

Ding, S.W. (2000) "RNA silencing" Current Opinion in Biotechnology, 11: 152-156.

Domeier, Mary Ellen et al. (2000) "A Link Between RNA Interference and Nonsense-Mediated Decay in Caenorhabditis elegans" Science, 289: 1928-1930.

Dorer et al. (1994) "Expansion of transgene repeats cause heterochromatin formation and gene silencing in Drosophilia" Cell 77: 993-1002.

Dorer, D.R. and Henikoff, S. (1997) "Transgene Repear Arrays Interact with Distant Heterochromatin and Cause Silencing in cis and trans" Genetics 147(3):1181-1190.

Ecker, J.R., Davis, R.W., (1986) "Inhibition of gene expression in plant cells by expression of antisense RNA," PNAS 83(15): 5372-5376.

Engdahl, H.M., et al. (1997) "A Two Unit Antisense RNA Cassette Test System for Silencing of Target Genes" Nucleic Acids Research 25(16): 3218-3227.

English, J.J., et al. (1996), "Suppression of Virus Accumulation in Transgenic Plants Exhibiting Silencing of Nuclear Genes", The Plant Cell 8(2): 179-188.

Erratum to Yu, M., et al. (1993) "A hairpin ribozyme inhibits expression of diverse strains of human immunodeficiency virus type 1," Proc. Natl. Acad. Sci. USA 90(17):8303.

Exhibit A from Benitec Australia Ltd. v. Nucleonics, Inc., Civil Litigation Action No. 04-174 (D. Del.) (JJF), filed Mar. 22, 2004 Exhibit A, 380 pages, submitted Jan. 28, 2005.

Exhibit B from Benitec Australia Ltd. v. Nucleonics, Inc., Civil Litigation Action No. 04-174 (D. Del.) (JJF), filed Mar. 22, 2004 Exhibit B, 20 pages, submitted Jan. 28, 2005.

Fire, A., Xu, S.Q., Montgomery, M.K., Kostas, S.A., Driver, S.E. and Mello, C.C. (1998) "Potent and Specific Genetic Interference by Double-Standard RNA in Caenorhabditis elegans" Nature, 391 (6669): 806-811.

Garrick, D., Fiering, S., Martin, D.I. and Whitelaw, E. (1998) "Repeat-Induced Gene Silencing in Mammals", Nature Genetics 18(1): 56-59.

Gervaix et al. (1997) "Multigene antiviral vectors inhibit diverse human immunodeficiency virus type 1 clades" Journal of Virology 71(4): 3048-3053.

Gura, Trisha (2000) "A silence that speaks volumes" Nature, 404: 804-80.

Hamilton, Andrew J. et al. (1999) "A Species of Small Antisense RNA in Posttranscriptional Gene Silencing in Plants" Science, 286: 950-952.

Hammond, Scott M. et al. (2000) "An RNA-directed nuclease mediates post-transcriptional gene silencing in Drosophila cells" Nature, 404: 293-296.

Izant and Weintraub (1984) "Inhibition of Thymidine Kinase Gene Expression by Anti-Sense RNA: A molecular Approach to Genetic Analysis," Cell vol. 36, 1007-1015.

Jacobs BL, Langland JO. "When two strands are better than one: the mediators and modulators of the cellular responses to double-stranded RNA," Virology (1996) 219(2):339-49.

Jorgensen, R. (1990) "Altered Gene Expression in Plants Due to Trans Interactions Between Homologous Genes" Trends in Biotechnology 8(12): 340-344.

Jorgensen, R.A., et al. (1996) "Chalcone Synthase Cosuppression Phenotypes in Petunia Flowers: Comparison of Sense vs. Antisense Constructs and Single-Copy vs. Complex T-DNA Sequences" Plant Molecular Biology 31(5): 957-973.

Jul. 20, 2007 decision of United States Court of Appeals for the Federal Circuit, 06-1122, in Benitec Australia Ltd. v. Nucleonics, Inc., Cert. Denied, Apr. 21, 2008.

Knoester, M., et al. (1997) "Modulation of Stress-Inducible Ethylene Biosynthesis by Sense and Antisense Gene Expression in Tobacco" Plant Science 126(2): 173-183.

Kunz, C., et al. (1996) "Developmentally Regulated Silencing and Reactivaation of Tobacco Chitinase Transgene Expression" The Plant Journal 10(3): 437-450.

Lee et al. (1994) "Inhibition of human immunodeficiency virus type 1 human T cells by a potent Rev response element decoy consisting of 13-nucleotide minimal Rev-binding domain" Journal of Virology 68(12): 8254-8264.

Lee, R.C., et al. (1993) "The C. elegans Heterochronic Gene lin-4 Encodes Small RNAs with Antisense Complementarity to lin-14" Cell 75: 843-854.

Lindbo, John et al. (1993) "Induction of a Highly Specific Antiviral State in Transgenic Plants: Implications for Regulation of Gene Expression and Virus Resistance" The Plant Cell, 5(12): 1749-1759.

Liszieuicz et al. (1993) "Inhibition of human immunodeficiency virus type 1 replication by regulated expression of a polymeric Tat activation response RNA decoy as a strategy for gene therapy in AIDS" PNAS 90: 8000-8004.

Liu, Z. et al. (1994) "Nuclear Antisense RNA: An Efficient New method to Inhibit Gene Expression," Molecular Biotechnology 2: 107-118.

Marx, Jean (2000) "Interfering With Gene Expression" Science, 288: 1370-1372.

Matzke, M.A., et al. (1998) "Epigenetic Silencing of Plant Transgenes as a Consequence of Diverse Cellular Defence Responses" Cellular and Molecular Life Sciences 54(1): 94-103.

Methods in Enzymology, vol. 185: Gene Expression Technology, edited by David V. Goeddel (1992).

Meyer, P. (1996) "Repeat-induced Gene Silencing—Common Mechanisms in Plants and Fungi" Biological Chemistry Hoppe-Seyler 377(2): 87-95.

Mueller, E., et al. (1995) "Homology-dependent Resistance—Transgenic Virus Resistance in Plants Related to Homology-Dependent Gene Silencing" The Plant Journal 7(6): 1001-1013.

Nellen, W. and Lichtenstein C. (1993) "What Makes a Messenger RNA Anti-Sensitive?" Trends in Biochemical Sciences 18(11): 419-423.

Palauqui, J.C., et al. (1997) "Systemic Acquired Silencing: Transgene-specific Post-transacriptional Silencing is Transmitted by Grafting from Silenced Stocks to Non-silenced scions" The EMBO Journal 16: 4738-4745.

Palauqui, Jean-Christophe et al. (1998) "Transgenes are dispensable for the RNA degradation step of cosuppression" Plant Biology, 95: 9675-9680.

Pal-Bhadra, M., Bhadra U. and Bitchier, J.A. (1997) "Cosuppression in *Drosophila*: Gene Silencing of Alcohol Dehydrogenase by White-Adh Tarnsgenes is Polycomb Dependent" Cell 90(3):479-90.

Pang, S.Z., et al. (1997) "Nontarget DNA Sequences Reduce the Transgene Length Necessary for RNA-mediated Tospovirus Resistance in Transgenic Plants" PNAS 94(15): 8261-8266.

Park, Y.D., et al. (1996) "Gene Silencing Mediated by Promoter Homology Occurs at the Level of Transcription and Results in Meiotically Heritable Alterations in Methylation and Gene Activity" The Plant Journal 9(2): 183-194.

Paul CP, Good PD, Winer I, Engelke DR. (2002) "Effective expression of small interfering RNA in human cells," Nat Biotechnol. 20(5):505-8.

Perkel, J.M. (2006) "Off-Target Effects Plague *Drosophila* RNAi" The Scientist, pp. 1-5.

Que, Q., et al. (1998) "Homology-based Control of Gene Expression Patterns in Transgenic *Petunia* Flowers" Developmental Genetics 22(1): 100-109.

Romano, N., et al. (1992) "Quelling: Transient Inactivation of Gene Expression in *Neurospora crassa* by Transformation with Homologous Sequences" Molecular Microbiology 6(22): 3343-3353.

Rosenberg, A. et al. (1987) "Vectors for selective expression of cloned DNAs by T7 RNA polymerase," Gene. 1987;56(1):125-35.

Sadiq, M., et al. (1994) "Developmental Regulation of Antisense-mediated Gene Silencing in *Dictyostelium*" Antisense Research & Development 4(4): 263-267.

Sijen, T., et al. (1996), "RNA-mediated Virus Resistance—Role of Repeated Transgenes and Delineation of Targeted Regions", The Plant Cell 8(12): 2277-2294.

Singer, M.J., et al. (1995) "Genetic and Epigenetic Inactivation of Repetitive Sequences in *Neurospora crassa*: RIP, DNA Methylation, and Quelling" Current Topics in Microbiology and Immunology 197: 165-177.

Smardon, Anne et al. (2000) "EGO-1 is related to RNA-directed RNA polymerase and functions in germ-line development and RNA interference in *C. elegans*" Current Biology, 10(4): 169-178.

Smyth, D.R. (1997) "Gene Silencing: Cosuppression at a Distance" Current Biology 7(12): R793-795.

Stain, M., et al. (1997) "The Silence of Genes in Transgenic Plants" Annals of Botany 79(1): 3-12.

Sullenger et al. (1990) "Overexpression of TAR sequences rendered cells resistant to human immundeficiency virus replication" Cell 63:601-608.

Sun et al. (1995) "Resistance to human immunodeficiency virus type 1 infection conferred by transduction of human peripheral blood lymphocytes with ribozyme, antisense, or polymeric transactivation response element constructs" PNAS 92: 7272-7276.

Tabare, Hiroaki et al. (1999) "The rde-1 Gene, RNA Interference, and Transposon Silencing in *C. elegans*", Cell, 99: 123-132.

Tetsuo, et al. (1997) "Comparison of three non-viral transfection methods for foreign gene expression in early chicken embryos in ovo," Biochemical and Biophysical Research Communications 230, 376-380.

Tanzer, M.M., et al. (1997) "Characterization of Post-Transcriptionally Suppressed Transgene Expression that Confers Resistance to Tobacco Etch Virus Infection in Tobacco" The Plant Cell 9(8): 1411-1423.

Trojan, J., et al. (1992) "Loss of tumorigenicity of rat glioblastoma directed by episome-based antisense cDNA transcription of insulin-like growth factor I," Proc. Natl. Acad. Sci. USA 89:4874-4878.

Trojan, J., et al. (1992) "Loss of tumorigenicity of rat glioblastoma directed by episome-based antisense cDNA transcription of insulin-like growth factor I," Proc. Natl. Acad. Sci. USA 89:4874-4878 (redacted).

Tuschl, Thomas et al. (1999) "Targeted mRNA degradation by double-stranded RNA in vitro" Genes & Development, 13: 3191-3197.

Vacheret, H. Nussaume, et al. (1997) "A Transciptionally Active State is Required for Post-Transcriptional Silencing (Cosuppresion) of Nitrate Reductase Host Genes and Transgenes" The Plant Cell 9(8): 1495-1504.

Van der Krol, et al. (1990) "Inhibition of Flower Pigmentation by Antisense CHS Genes: Promoter and Minimal Sequence Requirements for the Antisense Effect" Plant Molecular Biology 14(4): 457-466.

Voinnet, Olivier et al. (1998) "Systemic Spread of Sequence-Specific Transgene RNA Degradation in Plants Is Initiated by Localized Introduction of Ectopic Promoterless DNA" Cell, 95: 177-187.

Wang, S., and Dolnick, B.J. (1993) "Quantitative evaluation of intracellular sense: antisense RNA hybrid duplexes." Nucleic Acids Res. 21(18):4383-4391.

Yu, M., et al. (1993) "A hairpin ribozyme inhibits expression of diverse strains of human immunodeficiency virus type 1," Proc. Natl. Acad. Sci. USA 90:6340-6344.

Yu, M., et al. (1993) "A hairpin ribozyme inhibits expression of diverse strains of human immunodeficiency virus type 1," Proc. Natl. Acad. Sci. USA 90:6340-6344 (redacted).

Zamore, Phillip D. et al. (2000) "RNAi: Double-Stranded RNA Directs the ATP-Dependent Cleavage of mRNA at 21 to 23 Nucleotide Intervals", Cell 101: 25-33.

U.S. Appl. No. 60/068,562, filed Dec. 23, 1997, Fire et al.

Bissler, J.J. (1998) "DNA inverted repeats and human disease," Front Biosci. 3:408-418.

Chou, S.H., et al. (2003) "Unusual DNA duplex and hairpin motifs," Nucleic Acids Res. 31(10):2461-74.

Bussey, H., et al. (2006) "From worm genetic networks to complex human diseases" Nat. Genet. 38(8):862-863.

Gunsalus, K.C., and Piano, F. (2005) "RNAi as a tool to study cell biology: building the genome-phenome bridge" Curr. Opin. Cell. Biol. 17(1):3-8.

Homann, M., et al. (1996) "Dissociation of long-chain duplex RNA can occur via strand displacement in vitro: biological implications" Nucleic Acids Res. 24(22):4395-4400.

Prasad, B.V., et al. (1996) "Visualization of ordered genomic RNA and localization of transcriptional complexes in rotavirus" Nature. 382(6590):471-473.

Cohli et al. (1994) "Inhibition of HIV-1 multiplication in a human CD4+ lymphocytic cell line expressing antisense and sense RNA molecules containing HIV-1 packaging signal and Rev response element(s)" Antisense Research and Development 4:19-26.

Fire, et al. (1991) "Production of Antisense RNA Leads to Effective and Specific Inhibition of Gene Expression in *C. elegana* Muscle" Development, 113(2):503-514.

James, W. (1991) "Towards gene-inhibition therapy: a review of progress and prospects in the field of antiviral antisense nucleic acids and ribozymes," Antivir. Chem. Chemother. 2(4):191-214.

File of Re-examination Control No. 90/007,247, filed Oct. 4, 2004 including all references cited and disclosed, rejections and arguments therein (reexamination of U.S. Patent No. 6,573,099, issued Jun. 3, 2003 from U.S. Appl. No. 09/100,812).

Amendment submitted Jun. 12, 2006 in connection with U.S. Reexamination No. 90/007,247, filed Oct. 4, 2004.

Amendment submitted Nov. 28, 2005 in connection with U.S. Reexamination No. 90/007,247, filed Oct. 4, 2004.
Declaration [of Michael Graham, Ph.D.] Under 37 C.F.R. § 1.131 included with the Amendment submitted Jun. 12, 2006 in connection with U.S. Reexamination No. 90/007,247, filed Oct. 4, 2004.
Declaration of Michael Graham Under 37 C.F.R. § 1.132 included with the Amendment submitted Nov. 28, 2005 in connection with U.S. Reexamination No. 90/007,247, filed Oct. 4, 2004.
Ex Parte Reexamination Interview Summary issued Oct. 25, 2005 in connection with U.S. Reexamination No. 90/007,247, filed Oct. 4, 2004.
Letter to Examiner submitted Mar. 1, 2006, including a communication from the Australian Patent Office in connection with U.S. Reexamination No. 90/007,247, filed Oct. 4, 2004.
Office Action issued Apr. 12, 2006 in connection with U.S. Reexamination No. 90/007,247, filed Oct. 4, 2004.
Office Action issued Aug. 31, 2005 in connection with U.S. Reexamination No. 90/007,247, filed Oct. 4, 2004.
Order Granting / Denying Request for Ex Parte Rexamination issued Dec. 7, 2004 in connection with U.S. Reexamination No. 90/007,247, filed Oct. 4, 2004.
Request for Reexamination Pursuant to 35 U.S.C. §§ 302-307 and 37 C.F.R. § 1.510, submitted Oct. 4, 2004 in connection with U.S. Reexamination No. 90/007,247, filed Oct. 4, 2004.
Statement of the Content of the Interview Under 37 C.F.R. § 1.560(b) included with the Amendment submitted Nov. 28, 2005 in connection with U.S. Reexamination No. 90/007,247, filed Oct. 4, 2004.
Amendment submitted Apr. 24, 2007 in connection with Merged Reexamination Nos. 90/007,247 and 90/008,096, filed Oct. 4, 2004 and May 18, 2006, respectively.
Amendment submitted Aug. 3, 2007 in connection with Merged Reexamination Nos. 90/007,247 and 90/008,096, filed Oct. 4, 2004 and May 18, 2006, respectively.
Declaration [of Kenneth Reed, Ph.D.] Under 37 C.F.R. § 1.131 included with the Amendment submitted Apr. 24, 2007 in connection with Merged Reexamination Nos. 90/007,247 and 90/008,096, filed Oct. 4, 2004 and May 18, 2006, respectively.
Declaration [of Michael Graham, Ph.D.] Under 37 C.F.R. § 1.131 included with the Amendment submitted Apr. 24, 2007 in connection with Merged Reexamination Nos. 90/007,247 and 90/008,096, filed Oct. 4, 2004 and May 18, 2006, respectively.
Interview Summary issued Jul. 6, 2007 in connection with Merged Reexamination Nos. 90/007,247 and 90/008,096, filed Oct. 4, 2004 and May 18, 2006, respectively.
Interview Summary issued Mar. 2, 2007 in connection with Merged Reexamination Nos. 90/007,247 and 90/009,096, filed Oct. 4, 2004 and May 18, 2006, respectively.
Mar. 7, 2008 Communication to the Examiner, including Mar. 7, 2008 Declaration of Michael Graham Ph.D., in connection with Merged Reexamination Nos. 90/007,247 and 90/008,096, filed Oct. 4, 2004 and May 18, 2006, respectively.
Office Action issued Apr. 11, 2008 in connection with Merged Reexamination Nos. 90/007,247 and 90/008,096, filed Oct. 4, 2004 and May 18, 2006, respectively.
Office Action issued Jan. 24, 2007 in connection with Merged Reexamination Nos. 90/007,247 and 90/008,096, filed Oct. 4, 2004 and May 18, 2006, respectively.
Statement of the Content of the Interview Under 37 C.F.R. § 1.560(b) included with the Amendment submitted Aug. 3, 2007 in connection with Merged Reexamination Nos. 90/007,247 and 90/008,096, filed Oct. 4, 2004 and May 18, 2006, respectively.
Summary of the Substance of the Interview and Comments on Examiner's Notes submitted Mar. 16, 2007 in connection with Merged Reexamination Nos. 90/007,247 and 90/008,096, filed Oct. 4, 2004 and May 18, 2006, respectively.
Declaration of Dr. Arthur Riggs Under Under 37 C.F.R. §1.132, including Exhibits A to I submitted Feb. 26, 2009 in connection with Merged Reexamination Nos. 90/007,247 and 90/008,096, filed Oct. 4, 2004 and May 18, 2006, respectively.
Amendment after Final submitted Feb. 26, 2009 in connection with Merged Reexamination Nos. 90/007,247 and 90/008,096, filed Oct. 4, 2004 and May 18, 2006, respectively.

Amendment submitted Jul. 11, 2008 in connection with Merged Reexamination Nos. 90/007,247 and 90/008,096, filed Oct. 4, 2004 and May 18, 2006, respectively.
Interview Summary issued Feb. 12, 2009 in connection with Merged Reexamination Nos. 90/007,247 and 90/000,096, filed Oct. 4, 2004 and May 18, 2006, respectively.
Interview Summary issued Jun. 12, 2008 in connection with Merged Reexamination Nos. 90/007,247 and 90/008,096, filed Oct. 4, 2004 and May 18, 2006, respectively.
Amendment submitted Nov. 28, 2007 in connection with Merged Reexamination Nos. 90/007,247 and 90/008,096, filed Oct. 4, 2004 and May 18, 2006, respectively.
Office Action, issued Nov. 26, 2008 in connection with Merged Reexamination Nos. 90/007,247 and 90/008,096, filed Oct. 4, 2004 and May 18, 2006, respectively.
Office Action issued Nov. 19, 2008 in connection with Merged Reexamination Nos. 90/007,247 and 90/008,096, filed Oct. 4, 2004 and May 18, 2006, respectively.
File of Re-examination Control No. 90/008,096, filed May 18, 2006 including all references cited and disclosed, rejections and arguments therein (reexamination of U.S. Patent No. 6,573,099, issued Jun. 3, 2003 from U.S. Appl. No. 09/100,812).
Housekeeping Amendment submitted Nov. 27, 2006 in connection with U.S. Reexamination No. 90/008,096, filed May 18, 2006.
Notice of Failure to Comply with Ex Parte Reexamination Request Filing Requirements [37 CFR 1.510(c)] issued May 23, 2006 in connection with U.S. Reexamination No. 90/008,096, filed May 18, 2006.
Order Granting / Denying Request for Ex Parte Rexamination issued Jul. 20, 2006 in connection with U.S. Reexamination No. 90/008,096, filed May 18, 2006.
Reply to Notice of Failure to Comply with Ex Parte Reexamination Request Filing Requirements submitted Jun. 14, 2006 in connection with U.S. Reexamination No. 90/009,096, filed May 18, 2006.
Request for Reexamination Pursuant to 35 U.S.C. §§ 302-307 and 37 C.F.R. §§1.502 and 1.510, submitted May 18, 2006 in connection with U.S. Reexamination No. 90/009,096, filed May 18, 2006.
Amendment submitted Nov. 4, 2005 in connection with U.S. Appl. No. 10/292,996, filed Oct. 30, 2002.
Office Action issued Jan. 25, 2006 in connection with U.S. Appl. No. 10/282,996, filed Oct. 30, 2002.
Decision to refuse a European patent application dated Jul. 11, 2005, filed in EP 99 910 039.9.
"Table of animal viruses inactivated by RNA1, footnotes for individual viruses are provided" as Annex B of Statement setting out the Grounds of Appeal dated Nov. 11, 2005, filed in EP 99 910 039.9.
"References" as Annex C of Statement setting out the Grounds of Appeal dated Nov. 11, 2005, filed in EP 99 910 039.9.
"Summary of the Construction of pAM320" as Annex D of Statement setting out the Grounds of Appeal dated Nov. 11, 2005, filed in EP 99 910 039. 9.
Appeal submitted Nov. 11, 2005 against decision to refuse a European patent application issued Jul. 11, 2005, filed in EP 99 910 039.9.
European Search Report mailed Jun. 3, 2005, for EP 04015041, filed Mar. 19, 1999, 4 pages.
EPO Form 2001 dated Jul. 16, 2007 in connection with European Patent Application No. 05013010.3.
EPO Form 2906 dated Jul. 16, 2007 in connection with European Patent Application No. 05013010.3.
Hungarian Patent Office Search Report mailed Jul. 13, 2004, for Hungary patent application No. P0101225, 1 page.
Jan. 23, 2003 Declaration of Dr. Peter Waterhouse in connection with CSIRO's opposition to Australian Patent Application No. 743316.
Jan. 23, 2003 Declaration of Dr. Robert de Feyter in connection with CSIRO's opposition to Australian Patent Application No. 743316.
Jul. 24, 2002 Statement of Grounds and Particulars of Opposition in connection with CSIRO's opposition to Australian Patent Application No. 743316.
Oct. 9, 2003 Statutory Declaration of Dr. Michael Wayne Graham in connection with CSIRO's opposition to Australian Patent Application No. 743316.

Oct. 9, 2003 Statutory Declaration of Dr. Robert Norman Rice in connection with CSIRO's opposition to Australian Patent Application No. 743316.
Feb. 26, 2003 Statutory Declaration of Geoffrey Alan Ellacott in connection with CSIRO's opposition to Australian Patent Application No. 743316.
Oct. 9, 2003 Statutory Declaration of Kenneth Clifford Reed in connection with CSIRO's opposition to Australian Patent Application No. 743316.
Jan. 23, 2003 Statutory Declaration of Ming-Bo Wang in connection with CSIRO's opposition to Australian Patent Application No. 743316.
Jan. 23, 2003 Statutory Declaration of Neil Andrew Smith in connection with CSIRO's opposition to Australian Patent Application No. 743316.
Oct. 24, 2002 Statutory Declaration of William John Pickering in connection with CSIRO's opposition to Australian Patent Application No. 743316.
International Search Report mailed on May 10, 1999, for PCT patent application No. PCT/AU99/00195 filed Mar. 19, 1999, 3 pages.
International Search Report mailed on Oct. 16, 2000, for PCT application No. PCT/IB00/01133 filed Aug. 14, 2000.
International Search Report mailed on May 10, 2001, for PCT patent application No. PCT/AU01/00297 filed Mar. 16, 2001, 2 pages.
International Search Report mailed on Nov. 14, 2002, for PCT patent application No. PCT/AU02/01326 filed Sep. 27, 2002, 4 pages.
Minutes of Oral Proceeding dated Jul. 12, 2005, filed in EP 99 910 039.9.
Reply to Summons to attend Oral Proceeding filed May 13, 2005 in European Patent Application No. 99 910 039.9-2401.
Request for correction of minutes filed Aug. 2, 2005 in EP 99 910 039.9.
Statement setting out the Grounds of Appeal dated Nov. 11, 2005, filed in EP 99 910 039.9.
"Table describing sequences used to inhibit viral replication" as Annex A of Statement setting out the Grounds of Appeal dated Nov. 11, 2005, filed in EP 99 910 039.9.
Written Opinion mailed on Mar. 19, 2001, for PCT application No. PCT/IB00/01133 filed Aug. 14, 2000.
Written Opinion mailed on Apr. 17, 2004, for PCT application No. PCT/AU03/01177 filed Sep. 9, 2003, 7 pages.
Advisory Action issued Mar. 25, 2009 in connection with Merged Reexamination Nos. 90/007,247 and 90/008,096, filed Oct. 4, 2004 and May 18, 2006, respectively.
Petition Under 37 C.F.R. § 1.181 submitted Apr. 3, 2009 in connection with Merged Reexamination Nos. 90/007,247 and 90/008,096, filed Oct. 4, 2004 and May 18, 2006, respectively.
Petition Under 37 C.F.R. § 1.182 submitted Apr. 3, 2009 in connection with Merged Reexamination Nos. 90/007,247 and 90/008,096, filed Oct. 4, 2004 and May 18, 2006, respectively.
Petition for Extension of Time submitted Apr. 22, 2009 in connection with Merged Reexamination Nos. 90/007,247 and 90/008,096, filed Oct. 4, 2004 and May 18, 2006, respectively.
Advisory Action issued Apr. 24, 2009 in connection with Merged Reexamination Nos. 90/007,247 and 90/008,096, filed Oct. 4, 2004 and May 18, 2006, respectively.
Decision on Petition Under 37 C.F.R. § 1.181 issued Apr. 25, 2009 in connection with Merged Reexamination Nos. 90/007,247 and 90/008,096, filed Oct. 4, 2004 and May 18, 2006, respectively.
Decision on Petition for Extension of Time issued Apr. 27, 2009 in connection with Merged Reexamination Nos. 90/007,247 and 90/008,096, filed Oct. 4, 2004 and May 18, 2006, respectively.
Appeal Brief submitted Jul. 27, 2009 in connection with Merged Reexamination Nos. 90/007,247 and 90/008,096, filed Oct. 4, 2004 and May 18, 2006, respectively.
Notification of Non-compliant Appeal Brief in Ex Parte Reexamination issued Oct. 22, 2009 in connection with Merged Reexamination Nos. 90/007,247 and 90/008,096, filed Oct. 4, 2004 and May 18, 2006, respectively.
Communication in Response to Notification of Non-compliant Appeal Brief submitted Nov. 2, 2009 in connection with Merged Reexamination Nos. 90/007,247 and 90/008,096, filed Oct. 4, 2004 and May 18, 2006, respectively.

Examiner's Answer issued Jan. 7, 2010 in response to applicant's Appeal Brief filed Jul. 27, 2009 in connection with Merged Reexamination Nos. 90/007,247 and 90/008,096, filed Oct. 4, 2004 and May 18, 2006, respectively.
Reply Brief to Examiner's Answer submitted on Mar. 8, 2010, in connection with merged Reexamination Control Nos. 90/007,247 and 90/008,096, filed Oct. 4, 2004 and May 18, 2006, respectively.
Request for Oral Hearing submitted Mar. 8, 2010, in connection with merged Reexamination Control Nos. 90/007,247 and 90/008,096, filed Oct. 4, 2004 and May 18, 2006, respectively.
Sep. 29, 2010 Decision of the BPAI in connection with merged Reexamination Control Nos. 90/007,247 and 90/008,096, filed Oct. 4, 2004 and May 18, 2006, respectively.
Nov. 5, 2010 Notice of Intent to Issue Reexamination Certificate in connection with merged Reexamination Control Nos. 90/007,247 and 90/008,096, filed Oct. 4, 2004 and May 18, 2006, respectively.
Ex parte Reexamination Certificate issued Mar. 8, 2011 in connection merged Reexamination Control Nos. 90/007,247 and 90/008,096, filed Oct. 4, 2004 and May 18, 2006, respectively.
Agrawal et al. (2000) "Antisense therapeutics: is it as simple as complementary base recognition?" Molecular Medicine Today 6:72-81.
Agrawal, N. et al. (2003) "RNA Interference: Biology, Mechanism, and Applications" Microb. Mol. Biol. Rev. 67:657-685.
Agrawal, S. (1996) "Antisense oligonucleotides: towards clinical trials," Trends Biotechnol. 14(10):376-87.
Agrawal, S. et al. (1995) "Self-Stabilized Oligonucleotides as Novel Antisense Agents", pp. 105-122 in "Delivery Strategies for Antisense Oligonucleotide Therapeutics" (Akhtar, S., ed.), CRC Press, pubs.
Akgün, E., et al. (1997) "Palindrome resolution and recombination in the mammalian germ line," Mol. Cell. Biol. 17(9):5559-70.
Akhtar, S., and Rossi, J.J. (1996) "Anti-HIV therapy with antisense oligonucleotides and ribozymes: realistic approaches or expensive myths?" J. Antimicrob. Chemother. 38(2):159-65.
Angell, S.M. et al. (1997) "Consistent Gene Silencing in Transgenic Plants Expressing a Replicating Potato Virus X RNA," The EMBO Journal 16(12): 3675-3684.
Bahner, I. et al. (1996) "Transduction of human CD34+ hematopoietic progenitor cells by a retroviral vector expressing an RRE decoy inhibits human immunodeficiency virus type 1 replication in myelomonocytic cells produced in long-term culture," J. Virol. 70(7):4352-60.
Bahramian, M. B., et al. (1999) "Transcriptional and Post-transcriptional Silencing of Rodent α1(I) Collagen by a Homologous Transcriptionally Self-Silenced Transgene" Molecular and Cellular Biology, vol. 19, No. 1:274-283.
Barbeau, B., et al. (1996) "Characterization of the human and mouse Fli-1 promoter regions," Biochim. Biophys. Acta 1307(2):220-32.
Bass, Brenda L. (2001) "RNA Interference: The Short Answer," Nature, 411: 428-429.
Baum, E.Z., and Ernst, V.G. (1983) "Inhibition of protein synthesis in reticulocyte lysates by a double-stranded RNA component in HeLa mRNA," Biochem. Biophys. Res. Commun. 114(1):41-9.
Bhan, P., et al. (1997) "2',5'-linked oligo-3'-deoxyribonucleoside phosphorothioate chimeras: thermal stability and antisense inhibition of gene expression" Nucleic Acids Res. 25(16):3310-7.
Bigler, J., and Eisenman, R.N. (1995) "Novel location and function of a thyroid hormone response element," EMBO J. 14(22):5710-23.
Billy, E. et al. (2001) "Specific interference with gene induced by long, double-stranded RNA in mouse embryonal teratocarcinoma cell lines" PNAS 98(25):14428-33.
Birchler, J. A. (2000) "Making noise about silence: repression of repeated genes in animals" Current Opinion in Genetics & Development 10:211-216.
Bisat, F., et al. (1988) "Differential and cell type specific expression of murine alpha-interferon genes is regulated on the transcriptional level," Nucl. Acids Res. 16(13):6067-83.
Boldin, M.P. et al. (1996) "Involvement of MACH, a Novel MORT1/FADD-Interacting Protease, in Fas/APO-1-and TNF Receptor-Induced Cell Death" Cell 85:803-815.
Borecky, L. et al. (1981-1982) "Therapeutic Use of Double-Stranded RNAs in Man" Tex Rep Biol Med 14:575-581.

Braich, R.S., and Damha, M.J. (1997) "Regiospecific solid-phase synthesis of branched oligonucleotides. Effect of vicinal 2',5'-(or 2',3'-) and 3',5'-phosphodiester linkages on the formation of hairpin DNA" Bioconjug. Chem. 8(3):370-7.

Branch, A.D. (1998) "A good antisense molecule is hard to find," Trends Biochem. Sci. 23(2):45-50.

Brown, D.T., and Sittman, D.B. (1993) "Identification through overexpression and tagging of the variant type of the mouse H1e and H1c genes," J. Biol. Chem. 268(1):713-8.

Brummel, D. et al. (2003) "Inverted repeat of a heterologous 3'-untranslated region for high-efficiency, high-throughput gene silencing" The Plant Journal 33:793-800.

Brummelkamp, R. et al. (2002) "A System for Stable Expression of Short Interfering RNAs in Mammalian Cells" Science vol. 296:550-553.

Buchan, K.W., et al. (1994) "Characterization of three non-peptide endothelin receptor ligands using human cloned ETA and ETB receptors," Br. J. Pharmacol. 112(4):1251-7.

Cameron et al. (1994) "Multiple Domains in a Ribozyme Construct Confer Increased Suppressive Activity in Monkey Cells" Antisense Research and Development 4:87-94.

Caplen, Natasha J., et al. (2000) "dsRNA-mediated gene silencing in cultured Drosophila cells: a tissue culture model for the analysis of RNA interference" Gene, 252: 95-105.

Carthew, R. W. (2001) "Gene Silencing by Double-Stranded RNA" Curr. Op. Cell. Biol. 13:244-248.

Chernajovsky, Y., et al. (1996) "Human kinesin light (beta) chain gene: DNA sequence and functional characterization of its promoter and first exon," DNA Cell Biol. 15(11):965-74.

Christy, R.J., and Huang, R.C. (1988) "Functional analysis of the long terminal repeats of intracisternal A-particle genes: sequences within the U3 region determine both the efficiency and direction of promoter activity," Mol. Cell. Biol. 8(3):1093-102.

Clusel, C., et al. (1993) "Ex vivo regulation of specific gene expression by nanomolar concentration of double-stranded dumbbell oligonucleotides," Nucleic Acids Res. 21(15):3405-11.

Clusel, C., et al. (1995) "Inhibition of HSV-1 proliferation by decoy phosphodiester oligonucleotides containing ICP4 recognition sequences," Gene Expr. 4(6):301-9.

Cogoni, C., et al. (2000) "Past-transcriptional gene silencing across kingdoms" Current Opinion in Genetics & Development 10:638-643.

Coleman, J., et al. (1984) "The use of RNAs complementary to specific mRNAs to regulate the expression of individual bacterial genes" Cell 37:429-436.

Couzin, Jennifer (2002) "Small RNAs Make Big Splash" Science 298:2296-2297.

Czauderna, F. et al. (2003) "Structural Variations and Stabilising Modifications of Synthetic siRNAs in Mammalian Cells" Nucleic Acids Research vol. 31, No. 11:1-12.

de Feyter R et al. (1996) "A ribozyme gene and an antisense gene are equally effective in conferring resistance to tobacco mosaic virus on transgenic tobacco" Mol Gen Genet. 250: 329D338.

Shaffer. Dec. 17, 2004 edition (2004) Biotechnol. News 24(30):1-12 (Yanicek, C., ed., CTB International Publishing, Inc., Maplewood, N.J., pub.).

DeCoy, D.L., et al. (1995) "Anti sense DNA down-regulates proteins kinase C-epsilon and enhances vasopressin-stimulated Na+ absorption in rabbit cortical collecting duct" J. Clin. Invest. 95(6):2749-56.

Definition of "copy" (1995) Webster' s New World Dictionary, p. 135, Neufeldt, V., and Sparks, A.N., eds., Simon & Schuster Inc., New York, NY.

Dobrikova, E.Y., et al. (1996) "T7 DNA-dependent RNA polymerase can transcribe RNA from tick-borne encephalitis virus (TBEV) cDNA with SP6 promoter," FEBS Lett. 382(3):327-9.

Doench, J.G. et al. (2003) "siRNA Can Function as miRNAs" Genes and Development 17:438-442.

Dolnick, B.J. (1997) "Naturally occurring antisense RNA," Pharmacol. Ther. 75(3):179-84.

Dronkert, M.L. (2000) "Mouse RAD54 affects DNA double-strand break repair and sister chromatid exchange," Mol. Cell. Biol. 20(9):3147-56.

Dykxhoorn, D. et al. (2003) "Killing the Messenger: Short RNAs that Silence Gene Expression." Nature Reviews Molecular Cell Biology vol. 4:457-467.

Elbashir, S. M. et al. (2001) "Functional Anatomy of siRNAs for mediating Efficient RNAi in Drosophila melanogaster Embryo Lysate" The EMBO Journal, vol. 20, No. 23:6877-6888.

Elbashir, S. M. et al. (2002) "Analysis of Gene Function in Somatic Mammalian Cells Using Small Interfering RNAs" Methods 26:199-213.

Elroy-Stein, O., and Moss, B. (1990) "Cytoplasmic expression system based on constitutive synthesis of bacteriophage T7 RNA polymerase in mammalian cells," Proc. Natl. Acad. Sci. U.S.A. 87(17):6743-7.

Escudé, C., et al. (1996) "Stable triple helices formed by oligonucleotide N3'-->P5' phosphoramidates inhibit transcription elongation," Proc. Natl. Acad. Sci. U.S.A. 93(9):4365-9.

Farugi, T.R., and DiCorleto, P.E. (1997) "IFN-gamma inhibits double-stranded RNA-induced E-selectin expression in human endothelial cells," J. Immunol. 159(8):3969-94.

Fiaschi, T., et al. (1997) "The 5'-untranslated region of the human muscle acylphosphatase mRNA has an inhibitory effect on protein expression," FEBS Lett. 417(1):130-4.

Finkler, A., et al. (1992) "Immunity and resistance to the KP6 toxin of Ustilago maydis," Mol. Gen. Genet. 233(3):395-403.

Fire et al. (1998) "Potent and Specific Genetic Interference by Double-Stranded RNA in Caenorhabditis elegans" Nature 391:806-822.

Flavell, R.B. (1994) "Inactivation of Gene Expression in Plants as a Consequence of Specific Sequence Duplication" PNAS 99:3490-3496.

Fraser et al. (1996) "Effects of c-myc first exons and 5' synthetic hairpins on RNA translation in oocytes and early embryos of Xenopus laevis" Oncogene 12(6):1223-30.

Fuerst, T.R., et al. (1986) "Eukaryotic transient-expression system based on recombinant vaccinia virus that synthesizes bacteriophage T7 RNA polymerase," Proc. Natl. Acad. Sci. U.S.A. 83(21):8122-6.

Gao, L., et al. (1997) "Human genes encoding U3 snRNA associate with coiled bodies in interphase cells and are clustered on chromosome 17p11.2 in a complex inverted repeat structure," Nucleic Acids Res. 25(23):4740-7.

Gessani, S., et al. (1989) "Activators of protein kinase C enhance accumulation of interferon-beta mRNA in murine cell lines," J. Interferon Res. 9(5):543-50.

Gimmi, E. R., et al. (1989) "Alterations in the pre-mRNA topology of the bovine growth hormone polyadenylation region decrease poly(A) site efficiency," Nucleic Acids Res. 17(17):6983-98.

Giordano, E. et al. (2000) "RNAi Triggered by Symmetrically Transcribed Transgenes in Drosophila melanogaster" Genetics, 160:637-648.

Giovannangeli, C., et al. (1997) "Accessibility of nuclear DNA to triplex-forming oligonucleotides: the integrated HIV-1 provirus as a target," Proc. Natl. Acad. Sci. U.S.A. 94(1):79-84.

Goff, D.J. (1997) "Analysis of Hoxd-13 and Hoxd-11 Misexpression in Chick Limb Buds Reveals That Hox Genes Affect Both Bone Condensation and Growth" Development 124:627-636.

Graham, G. (1990) "RNA transcripts of the human immunodeficiency virus transactivation response element can inhibit action of the viral transactivator" Proc. Nat'l Acad. Sci. USA 87:5817-5821.

Graham, G.J., and Maio, J.J. (1992) "A rapid and reliable method to create tandem arrays of short DNA sequences," Biotechniques 13(5):780-9.

Grant, Sarah R. (1999) "Dissecting the Mechanisms of Post-transcriptional Gene Silencing: Divide and Conquer" Cell 96:303-306.

Grasby, J. et al. (1995) "Purine Functional Groups in Essential Residues of the Hairpin Ribozyme Required for Catalytic Cleavage of RNA" Biochemistry 34:4068-4076.

Griffey, R. H. et al. (1996) "2'O-Aminopropyl Ribonucleotides: A Zwitterrionic Modification That Enhances the Exonuclease Resistance and Biological Activity of Antisense Oligonucleotides" J. Med. Chem. 39:5100-5109.

Groger, R.K., et al. (1989) "Directional antisense and sense cDNA cloning using Epstein-Barr virus episomal expression vectors," Gene 81(2):285-94.

Gross, H.J., et al. (1982) "Nucleotide Sequence and Secondary Structure of Citrus Exocortis and Chrysanthemum Stunt Viroid," Eur. J. Biochem. 121(2):249-57.

Gryaznov, S.M. et al. (1993) "Template Controlled Coupling and Recombination of Oligonucleotide Blocks Containing Thiophosphoryl Groups" Nucleic Acids Research, vol. 21, No. 6:1403-1408.

Ha, Iiho et al. (1996) "A Bulged lin-14 RNA Duplex is Sufficient for *Caenorhabditis elegans* lin-14 Temporal Gradient Formation" Genes and Development 10:3041-3050.

Hacker, A., et al. (1995) "Expression of Sry, the mouse sex determining gene," Development 121(6):1603-14.

Haines, D.S., et al. (1991) "Cellular response to double-stranded RNA," J. Cell. Biochem. 46(1):9-20.

Hannon, G.J. (2002) "RNA Interference" Nature, vol. 418:244-251.

Harbinder, S., et al. (1997) "Genetically targeted cell disruption in *Caenorhabditis elegans*," Proc. Natl. Acad. Sci. U.S.A. 94(24):13128-33.

Harborth et al. (2001) "Identification of Essential Genes in Cultured Mammalian Cells Using Small Interfering RNAs," J. Cell Sci., 114: 4557-4565.

Harcourt, B.H., et al. (1998) "Ebola virus inhibits induction of genes by double-stranded RNA in endothelial cells," Virology 252(1):179-88.

Harfe, B.D., et al. (1998) "Analysis of a *Caenorhabditis elegans* Twist homolog identifies conserved and divergent aspects of mesodermal patterning," Genes Dev. 12(16):2623-35.

Henderson, S.T., and Petes, T.D. (1993) "Instability of a plasmid-borne inverted repeat in *Saccharomyces cerevisiae*," Genetics 134(1):57-62.

Hirashima, A., et al. (1986) "Engineering of the mRNA-interfering complementary RNA immune system against viral infection," Proc. Natl. Acad. Sci. U.S.A. 83(20):7726-30.

Hirashima, A., et al. (1989) "Artificial immune system against viral infection involving antisense RNA targeted to the 5'-terminal noncoding region of coliphage SP RNA," J. Biochem. 106(1):163-6.

Hoke, Glenn et al. (1991) "Effects of Phosporothioate Capping on Antisense Oligonucleotide Stability, Hybridization and Antiviral Efficacy Versus Herpes Simplex Virus Infection" Nucleic Acids Research vol. 19, No. 20:5743-5748.

Huang Y and Carmichael G (1996) "Role of polyadenylation in nucleocytoplasmic transport of mRNA" Mol. Cell. Biol. 16: 1534-1542.

Imazeki, F., et al. (1988) "Integrated structures of duck hepatitis B virus DNA in hepatocellular carcinoma," J. Virol. 62(3):861-5.

Jen et al. (2000) "Suppression of Gene Expression by Targeted Disruption of Messenger RNA:Available Options and Current Strategies" Stem Cells 18:307-319.

Jin, Z., et al. (1991) "Expression of firefly luciferase gene in *Xenopus laevis* oocyte," Chin. J. Biotechnol. 7(4):279-84.

Jorgensen, R.A. et al. (1999) "Do Unintended Antisense Transcripts Contribute to Sense Cosuppression in Plants" TIG 15:11-12.

Kennerdell, Jason (1998) "Use of dsRNA-Mediated Genetic Interference to Demonstrate that Frizzled and Frizzled 2 Act in the Wingless Pathway" Cell, vol. 95:1017-1026.

Kennerdell, Jason (2000) "Heritable Gene Silencing in *Drosophila* Using Double-Stranded RNA" Nature Biotechnology, 18:896-898.

Kibler et al. (1997) "Double Stranded RNA is a Trigger for Apoptosis in Vaccinia Virus Infected Cells" Journal of Virology, 71(3):1992-2003.

Kim S & Wold BJ (1985) "Stable Reduction of Thymidine Kinase Activity in Cells Expressing High Levels of Anti-Sense RNA" Cell vol. 42, 129-138.

Kitabwalla, M. (2002) "RNA Interference—A New Weapon Against HIV and Beyond" N Engl J. Med, vol. 347, No. 17:1364-1367.

Klaff, P., et al. (1996) "RNA structure and the regulation of gene expression," Plant Mol. Biol. 32(1-2):89-106.

Klink, V.P. et al. (2000) "The Efficacy of RNAi in the Study of the Plant Cytoskeleton" J. Plant Growth Reg. 19:371-384.

Kowolik, C.M. (2001) "Locus Control Region of the Human CD2 Gene in a Lentivirus Vector Confers Position-Independent Transgene Expression" Journal of Virology, vol. 75, No. 10:4641-4648.

Kowolik, C.M. (2002) "Preferential Transduction of Human Hepatocytes with Lentiviral Vectors Pseudotyped by Sendai Virus F Protein" Molecular Therapy, vol. 5, No. 6:762-769.

Kozak (1989) "Circumstances and mechanisms of inhibition of translation by secondary structure in eucaryotic mRNAs" Mol. Cell. Biol. 9:5134-5142.

Kreutzer et al., "Specific inhibition of viral gene expression by double-stranded RNA in vitro," Annual Fall Meeting of the GBH, Abstract for Poster Paper No. 328, p. S169 (1999).

Krystal, G.W., et al. (1990) "N-myc mRNA forms an RNA-RNA duplex with endogenous antisense transcripts," Mol. Cell. Biol. 10(8):4180-91.

Kumar M and Carmichael G (1998) "Antisense RNA: Function and Fate of Duplex RNA in Cells of Higher Eukaryotes" Microbiol. Mol. Biol. Rev. 62(4): 1415-1434.

Kumar Madhur, (1998) "Antisense RNA: Function and Fate of Duplex RNA in Cells of Higher Eukaryotes" Microbiology and Molecular Biology Reviews, vol. 62, No. 4:1415-1434.

Lee, S.W., et al. (1996) "The hemagglutinin genes hagB and hagC of *Porphyromonas gingivalis* are transcribed in vivo as shown by use of a new expression vector," Infect. Immun. 64(11):4802-10.

Levin, J.Z., et al. (2000) "Methods of double-stranded RNA-mediated gene inactivation in *Arabidopsis* and their use to define an essential gene in methionine biosynthesis" Plant Mol. Biol. 44(6):759-775.

Li, Y.X., et al. (2000) "Double-Stranded RNA Injections Produces Null Phenotype in Zebrafish" Dev Biol. 217(2):394-405.

Liebhaber et al. (1992) "Translation inhibition by an mRNA coding region secondary structure is determined by its proximity to the AUG initiation condon" J. Mol. Biol. 226:609-621.

Lin, R. (1999) "Policing Rogue Genes" Nature vol. 402:128-129.

Lingelbach et al. (1988) "An extended RNA/RNA duplex structure within the coding region of mRNA does not block translational elongaton" Nuc. Acids Res. 16:3405-3414.

Lipinski, C. et al. (1997) "Experimental and Computational Approaches to Estimate Solubility and Permeability in Drug Discovery and Development Settings" Advanced Drug Delivery Reviews 23:3-25.

Lisziewicz, J. et al. (1991) "Tat-Regulated Production of Multimerized TAR RNA Inhibits HIV-1 Gene Expression" New Biologist 3:82-89.

Lodish et al. (c1999) "Molecular Cell Biology" Chapter 11, Section 11.2. (New York: W. H. Freeman & Co.).

Loomis et al. (1991) "Antisense RNA inhibition of expression of a pair of tandemly repeated genes results in a delay in cell-cell adhesion in *Dictyostelium*" Antisense Res. Dev. 1:255-260.

Ma, Michael Y.X. et al. (1993) "Design and Synthesis of RNA Miniduplexes via a Synthetic Linker Approach" Biochemistry 32:1751-1758.

Macé, K., and Gazzolo, L. (1991) "Interferon-regulated viral replication in chronically HIV1-infected promonocytic U937 cells" Res Virol. 42(2-3):213-20.

Majumdar, A. et al. (1998) "Targeted Gene Knockout Mediated by Triple Helix Forming Oligonucleotides" Nature Genetics vol. 20:212-214.

Manche, Lisa et al. (1992) "Interactions Between Double-Stranded RNA Regulators and the Protein Kinase DAI," Mol. Cell. Biol., 12(11): 5238-5248.

Marathe, R. et al. (2000) "RNA viruses as inducers, suppressors and targets of post-transcriptional gene silencing" Plant Molecular Biology 43:295-306.

Matthieu, J.M., et al. (1992) "Myelin-deficient mutant mice. An in vivo model for inhibition of gene expression by natural antisense RNA" Ann. N.Y. Acad. Sci. 660:188-92.

Matzke M.A. et al. (1995) "How and Why Do Plants Inactivate Homologous (Trans)genes" Plant Physiol. 107:679-685.

Matzke, M.A. et al. (2003) "RNAi Extends Its Reach" Science 301(5636):1060-1.

Mayne, L.V., et al. (1988) "SV 40-transformed normal and DNA-repair-deficient human fibroblasts can be transfected with high frequency but retain only limited amounts of integrated DNA" Gene 66(1):65-76.

McCormack, S.J., et al. (1992) "Mechanism of interferon action: identification of a RNA binding domain within the N-terminal region of the human RNA-dependent P1/eIF-2 alpha protein kinase," Virol. 188(1):47-56.

McManus, M. T. (2002) "Gene Silencing in Mammals by Small Interfering RNAs" Nature Rev. Genetics, vol. 3:737-747.

McNair, A.N., et al. (1994) "Hepatitis delta virus replication in vitro is not affected by interferon-alpha or -gamma despite intact cellular responses to interferon and dsRNA," J. Gen. Virol. 75(Pt. 6):1371-8.

Mercola, D., and Cohen, J.S. (1995) "Antisense approaches to cancer gene therapy," Cancer Gene Ther. 2(1):47-59.

Mette, M.F., et al. (2000) "Transcriptional silencing and promoter methylation triggered by double-stranded RNA," EMBO J. 19(19):5194-201.

Mikoshiba et al. (1991) "Molecular biology of myelin basic protein: gene rearrangement and expression of anti-sense RNA in myelin-deficient mutants" Comp. Biochem. Physiol. 98:51-61.

Mikoshiba, K., et al. (1990) "Chimeric and molecular genetic analysis of myelin-deficient (shiverer and mld) mutant mice," Ann. N.Y. Acad. Sci. 605:166-82.

Milhaud, P.G. et al. (1991) "Free and Liposome-Encapsulated Double-Stranded RNAs as Inducers of Interferon, Interleukin-6, and Cellular Toxicity" Journal of Interferon Research 11:261-265.

Morishita, R., et al. (1996) "Role of transcriptional cis-elements, angiotensinogen gene-activating elements, of angiotensinogen gene in blood pressure regulation," Hypertension 27(3 Pt. 2):502-7.

Morris, K.V., et al. (2004) "Small interfering RNA-induced transcriptional gene silencing in human cells," Science 305(5688):1289-92.

Moss, E.G. et al. (1997) "The Cold Shock Domain Protein LIN-28 Controls Development Timing in *C. Elegans* and is Regulated by the lin-4 RNA" Cell, vol. 88:637-646.

Nagy, E., Rigby, W.F. (1995) "Glyceraldehyde-3-phosphate dehydrogenase selectively binds Au-rich RNA in the NAD(+)-binding region (Rossmann fold)," J. Biol. Chem. 270(6):2755-63.

Ngo, Huan et al. (1998) "Double-Stranded RNA Induces mRNA Degradation in *Trypanosome brucei*" PNAS vol. 95:14687-14692.

Nielsen, P. et al. (1997) "A Novel Class of Conformationally Restricted Oligonucleotide Analogues: Synthesis of 2', 3'-Bridged Monomers and RNA-Selective Hybridisation" Chem. Commun. (9):825-826.

Nikiforov, T.T. et al. (1992) "Oligodeoxynucleotides Containing 4-thiothymidine and 6-thiodeoxyguanosine as affinity labels for the Eco RV Restriction Endonuclease and Modification Methylase" Nucleic Acids Research, vol. 20, No. 6:1209-1214.

Noguchi, M., et al. (1994) "Characterization of an antisense Inr element in the eIF-2 alpha gene," J. Biol. Chem. 269(46):29161-7.

Noonberg SB et al. (1994) "In vivo generation of highly abundant sequence-specific oligonucleotides for antisense and triplex gene regulation" Nucleic Acids Research vol. 22 No. 14:2830-2836.

Oates, A.C. et al. (2000) "Too Much Interference: Injection of Double-Stranded RNA Has Nonspecific Effects in the Zebrafish Embryo" Development Biology 224:20-28.

Okano et al. (1991) "Myelin basic protein gene and the function of antisense RNA in its repression in myelin-deficient mutant mouse" J. Neurochem. 56:560-567.

Paddison, P. J. et al. (2002) "Short Hairpin RNAs (shRNAs) Induce Sequence-Specific Silencing in Mammalian Cells" Genes and Development 16:946-958.

Paddison, P.J. et al. (2002) "RNA Interference: The New Somatic Cell Genetics?" Cancer Cell, 2:17-23.

Palmiter, R.D., et al. (1984) "Transmission distortion and mosaicism in an unusual transgenic mouse pedigree," Cell 36(4):869-77.

Pe'ery, T., and Mathews, M.B. (1997) "Synthesis and purification of single-stranded RNA for use in experiments with PKR and in cell-free translation systems," Methods 11(4):371.

Pegram, M.D. et al. (1998) "Phase II study of Receptor-Enhanced Chemosensitivity Using Recombinant Humanized Anti-p185HER2/neu Monoclonal Antibody Plus Cisplain in Patients With HER2/Neu-Overexpressing Metastatic Breast Cancer Refratory to Chemotherapy Treatment" Journal of Clinical Oncology, vol. 16, No. 8:2659-2671.

Pelletier et al. (1985) "Insertion mutagenesis to increase secondary structure within the 5' noncoding region of a eukaryotic mRNA reduces translational efficiency" Cell, 40:515-526.

Peng, H. et al. (2001) "Development of an MFG-Based Retroviral Vector System for Secretion of High Levels of Functionally Active Human BMP4" Molecular Therapy, vol. 4, No. 2:95-104.

Peyman (1997) Basic Science of Vascular Disease (Chapter 17, p. 17).

Piccin et al. (2001) "Efficient and Heritable Functional Knock-out of an Adult Phenotype in *Drosophila* using a GAL4-Driven Hairpin RNA Incorporating a Heterologous Spacer" Nucleic Acids Research, 29(12) E55:1-5.

Plasterk, R. et al. (2000) "The Silence of the Genes" Curr. Op. Gen. Div. 10:562-567.

Pratt, G., et al. (1988) "Regulation of in vitro translation by double-stranded RNA in mammalian cell mRNA preparations," Nucleic Acids Res. 16(8):3497-510.

Putlitz, J. (1999) "Specific Inhibition of Hepatitis B Virus Replication by Sense RNA" Antisense & Nucleic Acid Drug Development 9:241-252.

Qua, Q., et al. (1997) "The Frequency and Degree of Cosuppression by Sense Chalcone Synthase Transgenes Are Dependent on Transgene Promoter Strength and Are Reduced by Premature Nonsense Codons in the Transgene Coding Sequence" Plant Cell 9:1357-1368.

Raponi, M., and Arndt, G.M. (2003) "Double-stranded RNA-mediated gene silencing in fission yeast," Nucleic Acids Res. 31(15):4481-9.

Ratcliff, F., et al. (1997) "A Similarity Between Viral Defense and Gene Silencing in Plants," Science 276(5318):1558-1560.

Regalado, A. (Aug. 6, 2002) "Turning Off Genes Sheds New Light on How They Work" The Wall Street Journal, starting at p. A1, 4 pages.

Resnekov, O., et al. (1989) "RNA secondary structure is an integral part of the in vitro mechanism of attenuation in simian virus 40," J. Biol. Chem. 264(17):9953-9.

Reuben, M., et al. (1994) "Cloning and expression of the rabbit gastric CCK-A receptor," Biochim. Biophys. Acta 1219(2):321-7.

Robertson, G., et al. (1996) "Age-dependent silencing of globin transgenes in the mouse," Nucleic Acids Res. 24(8):1465-71.

Rocheleau, C.E., et al. (1997) "Wnt signaling and an APC-related gene specify endoderm in early *C. elegans* embryos," Cell 90(4):707-16.

Rodriguez, D., et al. (1990) "Regulated expression of nuclear genes by T3 RNA polymerase and lac repressor, using recombinant vaccinia virus vectors," J. Virol. 64(10):4851-7.

Roy, P., et al. (1990) "Effect of mRNA secondary structure on the efficiency of translational initiation by eukaryotic ribosomes," Eur. J. Biochem. 191(3):647-52.

Ruskin, B., and Fink, G.R. (1993) "Mutations in POL1 increase the mitotic instability of tandem inverted repeats in *Saccharomyces cerevisiae*," Genetics 134(1):43-56.

Sabi, J.F., and Henikoff, S. (1996) "Copy number and orientation determine the susceptibility of a gene to silencing by nearby heterochromatin in *Drosophila*," Genetics 142(2):447-58.

Sachs A. and Wahle E. (1993) "Poly(A) tail metabolism and function in eucaryotes" J. Biol. Chem. 268: 22955-22958.

Sarver, N. et al., (1990) "Ribozymes as Potential Anti-HIV-1 Therapeutics Agents" Science 247:1222-1225.

Schaller, H. (2003) "The Role of Sterols in Plant Growth and Development" Prog. Lipid Res. 42:163-175.

Schmidt, F.R. (2004) "RNA Interference Detected 20 years ago" Nat. Biotechnol. 22:267-268.

Schmidt, F.R. et al. (1983) "Cycloheximide Induction of Aflatoxin Synthesis in a Nontoxigenic Strain of *Aspergillus flavus*" Bio/Technology 1:794-795.

Schmidt, F.R. et al. (1986) "Viral Influences on a flatoxin Formation by *Aspergillus flavus*" Appl Microbiol. Biotechnol. 24:248-252.

Schmitt, H P., et al. (1986) "Characterization of cloned sequence complementary to F9 cell double-stranded RNA and their expression during differentiation," Differentiation 30(3):205-10.

Schramke, V. (2003) "Hairpin RNAs and Retrotransposon LTRs Effect RNAi and Chromatin-Based Gene Silencing" Science 301:1069-1074.

Schwarz, D.S. et al. (2002) "Evidence that siRNAs Function as Guides, Not Primers in the *Drosophila* and Human RNAi Pathways" Molecular Cell, vol. 10:537-548.

Seife et al. (2003) "Breakthrough of the Year" Science 302:2038-2045.

Sharp, Phillip (1999) "RNAi and Double-Stranded RNA" Genes and Development 13(2):139-141.

Shi, Y. (1998) "A CBP/p300 Homolog Specific Multiple Differentiation Pathways in *Caenorhabditis elegans*" Genes and Development 12(7):943-55.

Silverman, T.A., et al. (1992) "Role of sequences within the first intron in the regulation of expression of eukaryotic initiation factor 2 alpha," J. Biol. Chem. 267(14):9738-42.

Simons, R.W. (1988) "Naturally occurring antisense RNA control—a brief review," Gene 2(1-2):35-44.

Sinha, N.D. (1997) "Large-Scale Synthesis: Approaches to Large-Scale Synthesis of Oligodeoxynecleotides and their Analogs" Antisense From Technology to Therapy Lab Manual and Textbook, vol. 6:30-58.

Skripkin, E. et al. (1996) "Psoralen Crosslinking Between Human Immunodeficiency Virus Type 1 RNA and Primer tRNA3Lys" Nucleic Acids Research, vol. 24, No. 3:509-514.

Smith, Neil et al. (2000) "Total Silencing by introspliced hairpin, RNAs", Nature, 407: 319-320.

Smolinski, P.A. (1995) "Double-stranded RNA induces sickle erythrocyte adherence to endothelium: a potential role for viral infection in vaso-occlusive pain episodes in sickle cell anemia," Blood 85(10):2945-50.

Smythe, J.A., and Symonds, G. (1995) "Gene therapeutic agents: the use of ribozymes, antisense, and RNA decoys for HIV-1 infection," Inflamm. Res. 44(1):11-5.

Sonode, K., et al. (1996) "Asymmetric deletion of the junction between the short unique region and the inverted repeat does not affect viral growth in culture and vaccine-induced immunity against Marek's disease," Vaccine 14(4):277-84.

Steinecke, P. et al. (1992) "Expression of a Chimeric Ribozyme Gene Results in Endocucleolytic Cleavage of a Target mRNA and a Concomitant Reduction of Gene Expression in vivo" Nucleic Acids Res. 23:2259-2268.

Strauss, Evelyn (1999) "Candidate Gene Silencers' Found" Science vol. 286:886.

Sullenger et al. (1990) "Expression of Chimeric tRNA-Driven Antisense Transcripts Renders NIH 3T3 Cells Highly Resistant to Moloney Murine Leukemia Virus Replication" Mol. Cell. Biol. 10:6512-6523.

Sullenger et al. (1993) "Tethering Ribozymes to a Retroviral Packaging Signal for Destruction of Viral RNA" Science 262:1566-1569.

Sun, L.Q., et al. (1994) "Ribozyme-mediated suppression of Moloney murine leukemia virus and human immunodeficiency virus type I replication in permissive cell lines," Proc. Natl. Acad. Sci. U.S.A. 91(21):9715-9.

Svoboda, P. et al. (2000) "Selective reduction of dormant maternal mRNAs in mouse oocytes by RNA interference" Development 127(19):4147-4156.

Svoboda, P. et al. (2001) "RNAi in Mouse Oocytes and Preimplantation Embryos: Effectiveness of Hairpin dsRNA" Biochem. Biophys Res Commun., 287(5):1099-1104.

Sweetser, D.A., et al. (1988) "Transgenic mice containing intestinal fatty acid-binding protein-human growth hormone fusion genes exhibit correct regional and cell-specific expression of the reporter gene in their small intestine," Proc. Natl. Acad. Sci. U.S.A. 85(24):9611-5.

Symington, L.S. (2002) "Role of RAD52 epistasis group genes in homologous recombination and double-strand break repair," Microbiol. Mol. Biol. Rev. 66(4):630-70.

Szyf et al. (1992) "Induction of Myogenic Differentiation by an Expression Vector Encoding the DNA Methyltransferase cDNA Sequence in the Antisense Orientation" J. Biol. Chem., 267:12831-12836.

Tabara (1998) Science 282:369.

Tanaka, H., et al. (1994) "Sequence-specific interaction of alpha-beta-anomeric double-stranded DNA with the p50 subunit of NF kappa B: application to the decoy approach," Nucleic Acids Res. 22(15):3069-74.

Tang, J.Y., et al. (1993) "Self-stabilized antisense oligodeoxynucleotide phosphorothioates: properties and anti-HIV activity" Nucleic Acids Res. 21(11):2729-2735.

Tavernarakis, N. et al. (2000) "Heritable and inducible genetic interference by double-stranded RNA encoded by transgenes" Nature Genetics 24:180-183 362. Tijsterman, M. et al. (2002) "The Genetics of RNA Silencing" Ann. Rev. Genet. 36:489-519.

Tijsterman, M. et al. (2002) "The Genetics of RNA Silencing" Ann. Rev. Genet. 36:489-519.

Timmons, L. (1998) "Specific Interference by Ingested dsRNA" Nature, vol. 395:854.

Tosic, M., et al. (1990) "Post-transcriptional events are responsible for low expression of myelin basic protein in myelin deficient mice: role of natural antisense RNA," EMBO J. 9(2):401-6.

Tuschl T. (2002) "Expanding small RNA interference" Nat Biotechnol. May;20(5):446-8.

Uhlmann, E. (1990) "Antisense Oligonucleotides: A New Therapeutic Principle" Chemical Reviews, vol. 9, No. 4:544-584.

Ui-Tei, K. et al. (2000) "Sensitive assay of RNA interference in *Drosophila* and Chinese hamster cultured cells using firefly luciferase gene as target" Fed. of Euro. Biochem. Socs Letters 479:79-82.

Usdin, T.B., et al. (1993) "SP6 RNA polymerase containing vaccinia virus for rapid expression of cloned genes in tissue culture," Biotechniques 14(2):222-4.

Van Steeg, H., et al. (1991) "The translation in vitro of rat ornithine decarboxylase mRNA is blocked by its 5' untranslated region in a polyamine-independent way," Biochem J. 274 (Pt. 2):521-6.

Volloch, V.Z., et al. (1994) "Evolutionarily conserved elements in the 5' untranslated region of beta globin mRNA mediate site-specific priming of a unique hairpin structure during cDNA synthesis," Nucleic Acids Res. 22(24):5302-9.

Wagner et al. (1998) "Double-stranded RNA poses puzzle" Nature 391:744-745.

Wallace RB et al. (1979) "Hybridization of synthetic oligodeoxyriboncleotides to phi chi 174 DNA: the effect of single base pair mismatch." Nucleic Acids Res.6(11):3543-57.

Wang, Z.Q., et al. (1994) "An unusual nucleoporin-related messenger ribonucleic acid is present in the germ cells of rat testis," Biol. Reprod. 51(5):1022-30.

Wargelius, A. et al. (1999) "Double-Stranded RNA Induces Specific Development Defects in Zebrafish Embryos" Biochem and Biophys Research Comma 263:156-161.

Watson (1988) "A new revision of the sequence of plasmid pBR322" Gene 70:399-403.

Weaver et al. (1981) "Introduction by molecular cloning of artifactual inverted sequences at the 5' terminus of the sense strand of bovine parathroid hormone cDNA" PNAS 78:4073-4077.

Wesa, L. (2003) "Early Days for RNAi" BioCentury, vol. 11, No. 12:A1-23.

Wianny, Florence et al. (2000) "Specific interference with gene function by double-stranded RNA in early mouse development", Nature Cell Biology, 2: 70-75.

Williams, T., and Fried, M. (1986) "A mouse locus at which transcription from both DNA strands produces mRNAs complementary at their 3' ends," Nature 322(6076):275-9.

Wolffe, A.P. (1997) "Transcription control: repressed repeats express themselves," Curr Biol. 7(12):R796-8.

Wu H et al. (1998) "Identification and Partial Purification of Human Double Strand RNase Activity" J Biol Chem, vol. 273, Issue 5, 2532-2542.

Wu, C., et al. (1994) "Interferon-stimulated response element and NF kappa B sites cooperate to regulate double-stranded RNA-induced transcription of the IP-10 gene," J. Interferon Res. 14(6):357-63.

Wu, S., and Kaufman, R.J. (1996) "Double-stranded (ds) RNA binding and not dimerization correlates with the activation of the dsRNA-dependent protein kinase (PKR)," J. Biol. Chem. 271(3):1756-63.

Xiong, Y., et al. (1995) "Signaling properties of mouse and human corticotropin-releasing factor (CRF) receptors: decreased coupling efficiency of human type II CRF receptor," Endocrinology 136(5):1828-34.

Yam, P.Y. et al. (2002) "Design of HIV Vectors for Efficient Gene Delivery into Human Hematopoietic Cells" Molecular Therapy, vol. 5, No. 4:479-484.

Yamamoto, R. et al. (1997) "Inhibition of Transcription by the TAR RNA of HIV-1 in a Nuclear Extract of HeLa Cells" Nucleic Acids Research, vol. 25, No. 17:3445-3450.

Yang, D., et al. (2000) "Evidence that processed small dsRNAs may mediate sequence-specific mRNA degradation during RNAi in *Drosophila* embryos," Curr. Biol. 10(19):1191-1200.

Yang, S. et al. (2001) "Specific double-stranded RNA interference in undifferentiated mouse embryonic stem cells" Molecular and Cellular Biology 21(22):7807-16.

Yarney, T.A., et al. (1993) "Molecular cloning and expression of the ovine testicular follicle stimulating hormone receptor," Mol. Cell. Endocrinol. 93(2):219-26.

Yee, Jiing-Kuan (2001) "Prospects for Gene Therapy Using HIV-Based Vectors" Somatic Cell and Molecular Genetics, vol. 26, Nos. 1/6:159-173.

Yu, J.Y., et al. (2002) "RNA interference by expression of short-interfering RNAs and hairpin RNAs in mammalian cells," Proc. Natl. Acad. Sci. USA 99(9):6047-52.

Yu, M., et al. (1994) "Progress towards gene therapy for HIV infection," Gene Ther. 1(1):13-26.

Zakharian, R.A., et al. (1986) "[Stimulation by double-stranded RNA of the transformation of pro- and eukaryotic cells]," Dokl. Akad. Nauk. SSSR 288(5):1251-3.

Zhao, J.J. et al. (1993) "Generating Loss-of-Function Phenotype of the Fushi Tarazu Gene with a Targeted Ribozyme in *Drosophila*" Nature 365:448-451.

U.S. Appl. No. 09/056,767, filed Apr. 8, 1998 (Peter Michael Waterhouse et al.).

U.S. Appl. No. 09/056,767, filed Apr. 8, 1998 (Peter Michael Waterhouse et al.), including complete file history.

U.S. Appl. No. 09/127,735, filed Aug. 3, 1998 (Peter Michael Waterhouse et al.).

U.S. Appl. No. 09/127,735, filed Aug. 3, 1998 (Peter Michael Waterhouse et al.), including complete file history.

U.S. Appl. No. 09/287,632, filed Apr. 7, 1999 (Peter Michael Waterhouse et al.).

U.S. Appl. No. 09/287,632, filed Apr. 7, 1999 (Peter Michael Waterhouse et al.), including complete file history.

Advisory Action issued Apr. 11, 2002 in connection with U.S. Appl. No. 09/287,632, filed Apr. 7, 1999.

Amendment submitted Apr. 2, 2002 in connection with U.S. Appl. No. 09/287,632, filed Apr. 7, 1999.

Amendment submitted Aug. 21, 2000 in connection with U.S. Appl. No. 09/287,632, filed Apr. 7, 1999.

Amendment submitted Aug. 24, 2001 in connection with U.S. Appl. No. 09/287,632, filed Apr. 7, 1999.

Amendment submitted Aug. 8, 2007 in connection with U.S. Appl. No. 09/287,632, filed Apr. 7, 1999.

Amendment submitted Jan. 16, 2003 in connection with U.S. Appl. No. 09/287,632, filed Apr. 7, 1999.

Amendment submitted Jul. 7, 2003 in connection with U.S. Appl. No. 09/287,632, filed Apr. 7, 1999.

Amendment submitted Jun. 11, 2001 in connection with U.S. Appl. No. 09/287,632, filed Apr. 7, 1999.

Amendment submitted Mar. 5, 2001 in connection with U.S. Appl. No. 09/287,632, filed Apr. 7, 1999.

Amendment submitted May 1, 2008 in connection with U.S. Appl. No. 09/287,632, filed Apr. 7, 1999.

Amendment submitted May 10, 2006 in connection with U.S. Appl. No. 09/287,632, filed Apr. 7, 1999.

Amendment submitted Nov. 22, 2006 in connection with U.S. Appl. No. 09/287,632, filed Apr. 7, 1999.

Amendment submitted Sep. 12, 2005 in connection with U.S. Appl. No. 09/287,632, filed Apr. 7, 1999.

Communication issued Aug. 21, 2001 in connection with U.S. Appl. No. 09/287,632, filed Apr. 7, 1999.

Communication issued Dec. 3, 2004, in connection with U.S. Appl. No. 09/287,632, filed Apr. 7, 1999.

Communication issued Jul. 21, 2000 in connection with U.S. Appl. No. 09/287,632, filed Apr. 7, 1999.

Communication issued Jun. 2, 1999 in connection with U.S. Appl. No. 09/287,632, filed Apr. 7, 1999.

Communication issued Mar. 25, 2004 in connection with U.S. Appl. No. 09/287,632, filed Apr. 7, 1999.

Communication submitted May 18, 2001 in connection with U.S. Appl. No. 09/287,632, filed Apr. 7, 1999.

Declaration of Dr. Elizabeth Salisbury Dennis Under Under 37 C.F.R. §1.132, including Exhibits 1 to 14 submitted Aug. 8, 2007 in connection with U.S. Appl. No. 09/287,632, filed Apr. 7, 1999.

Declaration of Dr. Marc De Block Under 37 C.F.R. §1.132, including Annexes 1 and 2 submitted Aug. 8, 2007, in connection with U.S. Appl. No. 09/287,632, filed Apr. 7, 1999.

Interview Summary issued Jul. 29, 2004 in connection with U.S. Appl. No. 09/287,632, filed Apr. 7, 1999.

Interview Summary issued Jun. 2, 2006, in connection with U.S. Appl. No. 09/287,632, filed Apr. 7, 1999.

Interview Summary issued Nov. 30, 2007 in connection with U.S. Appl. No. 09/287,632, filed Apr. 7, 1999.

Interview Summary of Sep. 5, 2002 Interview in connection with U.S. Appl. No. 09/287,632, filed Apr. 7, 1999.

May 1, 2008 Declaration Under 37 C.F.R. § 1.131, including Exhibits 1 to 5 of Peter Michael Waterhouse, Michael Wayne Graham, Ming-Bo Wang and Neil A. Smith in connection with U.S. Appl. No. 09/287,632, filed Apr. 7, 1999.

May 7, 2008 Declaration Under 37 C.F.R. 1.132 of Peter Robert Schofield Resubmission in connection with U.S. Appl. No. 09/287,632, filed Apr. 7, 1999.

Nov. 1, 2007 Declaration Under 37 C.F.R. § 1.131, including Exhibits 1 to 5 of Dr. Elizabeth Salisbury Dennis in connection with U.S. Appl. No. 09/287,632, filed Apr. 7, 1999.

Office Action issued Apr. 9, 2003 in connection with U.S. Appl. No. 09/287,632, filed Apr. 7, 1999.

Office Action issued Feb. 8, 2007, in connection with U.S. Appl. No. 09/287,632, filed Apr. 7, 1999.

Office Action issued Jul. 16, 2002 in connection with U.S. Appl. No. 09/287,632, filed Apr. 7, 1999.

Office Action issued Jun. 22, 2006 in connection with U.S. Appl. No. 09/287,632, filed Apr. 7, 1999.

Office Action issued Mar. 11, 2005 in connection with U.S. Appl. No. 09/287,632, filed Apr. 7, 1999.

Office Action issued Nov. 1, 2007, in connection with U.S. Appl. No. 09/287,632, filed Apr. 7, 1999.

Office Action issued Nov. 10, 2005 in connection with U.S. Appl. No. 09/287,632, filed Apr. 7, 1999.

Office Action issued Nov. 2, 2001 in connection with U.S. Appl. No. 09/287,632, filed Apr. 7, 1999.

Office Action issued Nov. 3, 2004 in connection with U.S. Appl. No. 09/287,632, filed Apr. 7, 1999.

Office Action issued Oct. 3, 2000 in connection with U.S. Appl. No. 09/287,632, filed Apr. 7, 1999.

Office Action issued Sep. 19, 2008 in connection with U.S. Appl. No. 09/287,632, filed Apr. 7, 1999.

Petition to Correct Inventorship Pursuant to 37 C.F.R. 1.48(a) submitted Sep. 13, 2006 in connection with U.S. Appl. No. 09/287,632, filed Apr. 7, 1999.

Preliminary Amendment submitted Jun. 28, 1999 in connection with U.S. Appl. No. 09/287,632, filed Apr. 7, 1999.

Summary of Interview submitted Aug. 6, 2004 in connection with U.S. Appl. No. 09/287,632, filed Apr. 7, 1999.

Office Action issued Sep. 1, 2005 in connection with U.S. Appl. No. 10/755,328, filed Jan. 13, 2004.

Preliminary Amendment submitted Jan. 13, 2004 in connection with U.S. Appl. No. 10/755,328, filed Jan. 13, 2004.

Amendment submitted Jan. 10, 2008 in connection with U.S. Appl. No. 11/364,183, filed Mar. 1, 2006.

Amendment submitted Jul. 2, 2008 in connection with U.S. Appl. No. 11/364,183, filed Mar. 1, 2006.

Interview Summary for Feb. 1, 2008 Interview in connection with U.S. Appl. No. 11/364,183, filed Mar. 1, 2006.

Interview Summary from Feb. 11, 2009 Interview in connection with U.S. Appl. No. 11/364,183, filed Mar. 1, 2006.
Jul. 2, 2008 Declaration Under 37 C.F.R. § 1.131, including Exhibits 1 to 3 of Peter Michael Waterhouse, Michael Wayne Graham, and Ming-Bo Wang in connection with U.S. Appl. No. 11/364,183, filed Mar. 1, 2006.
Office Action issued Apr. 17, 2008 in connection with U.S. Appl. No. 11/364,183, filed Mar. 1, 2006.
Office Action issued Jul. 10, 2007 in connection with U.S. Appl. No. 11/364,183, filed Mar. 1, 2006.
Preliminary Amendment submitted Mar. 1, 2006 in connection with U.S. Appl. No. 11/364,183, filed Mar. 1, 2006.
Amendment submitted Jan. 30, 2009 in connection with U.S. Appl. No. 11/607,062, filed Dec. 1, 2006.
Office Action issued Jul. 31, 2008 in connection with U.S. Appl. No. 11/607,062, filed Dec. 1, 2006.
Preliminary Amendment submitted Dec. 1, 2006 in connection with U.S. Appl. No. 11/607,062, filed Dec. 1, 2006.
Amendment submitted Jan. 16, 2008 in connection with U.S. Appl. No. 11/841,737, filed Aug. 20, 2007.
Notice of Publication issued May 1, 2008 in connection with U.S. Appl. No. 11/841,737, filed Aug. 20, 2007.
Alberts, B., et al. (1989) "Molecular Biology of the Cell" 2nd ed., pp. 102, 486487 and 532-535 (Garland Publishing, Inc., New York, NY, pubs.).
Australian Written Opinion for SG200205122-5 dated Oct. 24, 2005.
Amendment submitted Mar. 19, 2009 in connection with U.S. Appl. No. 09/287,632, filed Apr. 7, 1999.
Mar. 18, 2009 Declaration Under 37 C.F.R. 1.131 including Annexes I to III, of Dr. Michael Metzlaff in connection with U.S. Appl. No. 09/287,632, filed Apr. 7, 1999.
Office Action issued May 11, 2009 in connection with U.S. Appl. No. 09/287,632, filed Apr. 7, 1999.
Amendment submitted Nov. 5, 2009 in connection with U.S. Appl. No. 09/287,632, filed Apr. 7, 1999.
Office Action issued Dec. 8, 2009 in connection with U.S. Appl. No. 09/287,632, filed Apr. 7, 1999.
Appeal Brief submitted Apr. 8, 2010 in connection with U.S. Appl. No. 09/287,632, filed Apr. 7, 1999.
Examiner's Answer issued Jul. 7, 2010 in connection with U.S. Appl. No. 09/287,632, filed Apr. 7, 1999.
Reply Brief submitted Sep. 7, 2010 in connection with U.S. Appl. No. 09/287,632, filed Apr. 7, 1999.
Suggestion of Interference Pursuant to 37 C.F.R. § 41.202, submitted Apr. 15, 2009, in connection with U.S. Appl. No. 11/364,183, filed Mar. 1, 2006.
Amendment submitted Apr. 15, 2009, in connection with U.S. Appl. No. 11/364,183, filed Mar. 1, 2006.
Declaration of Geoffrey Ellacott submitted Apr. 15, 2009, in connection with U.S. Appl. No. 11/364,183, filed Mar. 1, 2006.
Declaration of Neil Smith submitted Apr. 15, 2009, in connection with U.S. Appl. No. 11/364,183, filed Mar. 1, 2006.
Declaration of Peter Michael Waterhouse submitted Apr. 15, 2009, in connection with U.S. Appl. No. 11/364,103, filed Mar. 1, 2006.
Declaration by Dr. Michael Metzlaff Under 37 C.F.R. § 1.132 submitted Apr. 15, 2009, in connection with U.S. Appl. No. 11/364,183, filed Mar. 1, 2006.
Examiner Interview Summary Record (PTOL-413) issued Aug. 12, 2009 in connection with U.S. Appl. No. 11/364,183, filed Mar. 1, 2006.
Supplemental Response or Supplemental Amendment submitted Aug. 10, 2009 in connection with U.S. Appl. No. 11/364,183, filed Mar. 1, 2006.
Notice to the applicant regarding a non-compliant or non-responsive amendment issued Jul. 9, 2009 in connection with U.S. Appl. No. 11/364,183, filed Mar. 1, 2006.
Office Action issued Nov. 4, 2009 in connection with U.S. Appl. No. 11/364,183, filed Mar. 1, 2006.
Revised Amendment and Reply submitted Aug. 10, 2009 in connection with U.S. Appl. No. 11/364,183, filed Mar. 1, 2006.
Reply to the Nov. 4, 2009 Office Action submitted May 4, 2010 in connection with U.S. Appl. No. 11/364,183, filed Mar. 1, 2006.
Office Communication issued Jun. 8, 2010 in connection with U.S. Appl. No. 11/364,183, filed Mar. 1, 2006.
Office Communication issued Jun. 11, 2010 in connection with U.S. Appl. No. 11/364,183, filed Mar. 1, 2006.
Jun. 17, 2010 Declaration of Interference issued in connection with U.S. Appl. No. 11/364,183, filed Mar. 1, 2006.
Redeclaration of Interference issued Jul. 6, 2010 in connection with U.S. Appl. No. 11/364,183, filed Mar. 1, 2006.
Redeclaration of Interference issued Sep. 10, 2010 in connection with U.S. Appl. No. 11/364,183, filed Mar. 1, 2006.
Redeclaration of Interference issued Nov. 17, 2010 in connection With U.S. Appl. No. 11/364,103, filed Mar. 1, 2006.
Office Action issued May 12, 2009 in connection with U.S. Appl. No. 11/607,062, filed Dec. 1, 2006.
Restriction Requirement issued May 4, 2009 in connection with U.S. Appl. No. 11/841,737, filed Aug. 20, 2007.
Non-Final Rejection issued Aug. 12, 2009 in connection with U.S. Appl. No. 11/841,737, filed Aug. 20, 2007.
Amendment submitted Jul. 6, 2009 in connection with U.S. Appl. No. 11/841,737, filed Aug. 20, 2007.
Amendment submitted Feb. 12, 2010 in connection with U.S. Appl. No. 11/841,737, filed Aug. 20, 2007.
Final Rejection issued Apr. 23, 2010 in connection with U.S. Appl. No. 11/841,737, filed Aug. 20, 2007.
Barry et al. (1993) "Methylation induced premeiotically in ascobolus: coextension with DNA repeat legths and effect on transcript elongation" Proc. Natl. Acad. Sci. 90:4557-4561.
Baulcombe (1996), "Mechanisms of Pathogen-Derived Resistance to Viruses in Transgenic Plants," Plant Cell, vol. 8:1833-1844.
Blomberg et al. (1990) "Control of Replication of Plasmid R1: the Duplex Between the Antisense RNA, CopA and its Target, CopT, is Processed Specifically in vivo and in vitro by Rnase III" The EMBO Journal 9:2331-2340.
Brantl et al. (1991) "Copy Number Control of the Streptococcal Plasmid pIP501 Occurs at Three Levels" Nucleic Acids Research 20:395-400.
Braun and Hemenway (1992) "Expression of Amino-Terminal Portions or Full-Length Viral Replicase Genes in Transgenic Plants Confers Resistance to Potato Virus X Infection" Plant Cell 4:735-744.
Brederode et al. (1995) "Replicase-Mediated Resistance to Alfalfa Mosaic Virus" Virology 207:467-474.
Brussian, J.A. et al., (1993) "An Arabidopsis Mutant with a Reduced Level of cab140 RNA is a Result of Cosuppression" The Plant Cell, American Society of Plant Physiologists, Rockville, MD, USA, 5:667-677.
Byzova et al. (2004) "Transforming Petals Into Sepaloid Organs in Araidopsis and Oilseed Rape: Implementation of the Hairpin RNA Mediated Gene Silencing Technology in an Organ-Specific Manner" Planta 218:379-87.
Cameron et al. (1989) "Specific Gene Supression by Engineered Ribozymes in Monkey Cells" Proc. Natl. Acad. Sci. USA 86:9139-9143.
Carr et al. (1992) "Resistance to Tobacco Mosaic Virus Induced by the 54-k Da Gene Sequence Requires Expression of the 54-k Da Protein" Mol. Plant Microbe Interact. 5:397-404.
Chen et al. (2003) "Temporal and Spatial Control of Gene Silencing in Transgenic Plants by Inducible Expression of Double Stranded RNA" The Plant Journal 36:731-40.
Dale et al. (1990) "Intra-and Intermolecular Site-Specific Recombination in Plant Cells Mediated by Bacteriophage P1 Recombinase" Gene 91:79-85.
Denoya et al. (1986) "Translational Autoregulation of ermC 23S rRNA Methyltransferase Expression in Bacillus subtilis" Journal of Bacteriology 113-1141.
Dougherty, W.G., et al. (1997) "Transgene and Gene Suppression: telling us something new?" Current Opinion in Cell Biology, Current Biology, UK, 7:399-405.
Faske, M. et al. (1997) "Transgenic Tobacco Plants Expressing Pea Chloroplast Nmdh cDNA in Sense and AntiSense Orientation," Plant Physiol., Am. Soc. of Plant Physiologists, Lancaster, PA, 115:705-715.

Garcia et al. (2004) "A Classical Arabinogalactan Protein in Essential for the Initiation of Female Gametogenesis in *Arabidopsis*" The Plant Cell 16:2614-28.
Genbank Accession No. L26296, Jun. 28, 1994.
Genbank Accession No. AF 124360, Jul. 21, 2000.
Genbank Accession No. A65102, Nov. 14, 2006.
Genbank Accession No. AF043841, Jun. 5, 1999.
Goodwin et al. (1996) "Genetic and Biochemical Dissection of Transgenic RNA-Mediated Virus Resistance" Plant Cell 8:95-105.
Graham, M.W. et al. (1996) "Co-suppression, Anti-Sense and Synthetic Viral Resistance: a Common Mechanism!" Symposium 4-3, Abstract for talk given by Michael Graham at the Lorne Genome Conference, Victoria, Australia, Feb. 1996.
Guo et al. (2003) "A Chemical Regulated Inducible RNAi System in Plants" The Plant Journal 34:383-92.
Hama et al. (1990) "Organization of the Replication Control Region of Plasmid Collb-P9" Journal of Bacteriology 1983-1991.
Hamilton et al. (1990) "Antisense Gene That Inhibits Synthesis of the Hormone Ethylene in Transgenic Plants" Nature 346:284-287.
Hergersberg, M. (1998) Inaugural Dissertation, Universität Koln.
Hobbs et al. (1990) "The Effect of T-DNA Copy Number, Position and Methylation on Reporter Gene Expression in Tobacco Transformants" Plant Mol. Biol. 15:851-864.
Ingelbrecht et al. (1994) "Postranscriptional Silencing of Reporter Transgenes in Tobacco Corrects with DNA Methylation" 91:10502-10506.
Jorgensen et al. (1997) "T-DNA is Organized Predominantly in Inverted Repeat Structures in Plants Transformed with *Agrobacterium tumefaciens* C58 Derivatives" Mol. Gen. Genet. 207:471-477.
Katsuki, Motoya et al. (1988) "Conversion of Normal Behavior to Shiverer by Myelin Basic Protein Antisense cDNA in Transgenic Mice" Science, 241: 593-595.
Kawcheck et al. (1991) "Sense and Antisense RNA-Mediated Resistance to Potato Leafroll Virus in Russet Burbank Potato Plants" 4:247-253.
Kelton, C.A., et al. (1992) "The cloning of the human follicle stimulating hormone receptor and its expression in COS-7, CHO, and Y-1 cells," Mol. Cell. Endocrinol. 89(1-2):141-51.
Kook, Yoon Hoh et al. (1994) "The effect of antisense inhibition of urokinase receptor in human squamous cell carcinoma on malignancy" The EMBO Journal, 13(17): 3983-3991.
Kubo et al. (1989) "mRNA Secondary Structure in an Open Reading Frame Reduces Translation Efficiency in *Bacillus subtilis*" Journal of Bacteriology 171:4080-4082.
Kuipers et al. (1995) "Factors Affecting the Inhibition by Antisense RNA of Granule-Bound Starch Synthase Gene Expression in Potato" Mol. Gen. Genet. 246:745-755.
Kumagai et al. (1995) "Cytoplasmic Inhibition of Carotenoid Biosynthesis With Virus-Derived RNA" Genetics 92:1679-1683.
Lee et al. (2003) "Making a Better RNAi Vector for *Drosophila*: Use of Intron Spacers" Methods 30:322-9.
Leech at al. (1993) "Expression of myb-related Genes in the Moss, *Physcomitrella patens*" The Plant Journal 3:51-61.
Li et al. (2005) "The Cotton ACTIN1 Gene is Functionally Expressed in Fibers and Participates in Fiber Elongation" The Plant Cell 17:859-75.
Lindbo & Dougherty (1992) "Pathogen-Derived Resistance to a Potyvirus: Immune and Resistant Phenotypes in Transgenic Tobacco Expressing Altered Forms of a Potyvirus Coat Protein Nucleotide Sequence" Mol. Plant Micr. Int. 5:144-153.
Lindbo & Dougherty (1992) "Untranslatable Transcripts of the Tobacco Etch Virus Coat Protein Gene Sequence Can Interfere With Tobacco Etch Virus Replication in Transgenic Plants and Protoplasts" Virology 189:725-733.
Lindbo, John et al. (2001) "Virus-Mediated Reprogramming of Gene Expression in Plants" Current Opinion in Plant Biology, 4:181-185.
Liziewicz et al. (1991) "Tat-Regulated Production of Multimerized TAR RNA Inhibits HIV-I Gene Expression" The New Biologist 3:82-89.
Lo et al. (1992) "Inhibition of Replication of HIB-1by Retroviral Vectors Expressing tat-Antisense an Anti-tat Ribozyme RNA" Virology 190:176-183.

Longstaff et al. (1993) "Extreme Resistance to Potato Virus X Infection in Plants Expressing a Modified Component of the Putative Viral Replicase" EMBO J. 12:379-386.
Lovett et al. (1990) "Translational Attenuation as the Regulator of Inducible cat Genes" Journal of Bacteriology 172:1-6.
Marathe, R.P (1997) "CIS-Repeat Induced Gene Silencing in Tobacco," Ph.D. Thesis, University of South Carolina.
Marathe, R.P. et al. (1997) "Cis Repeat Induced Gene Silencing in Tobacco," Abstract P10141.
Memelink et al. (1992) "Structure and Regulation of Tobacco Extensin" The Plant Journal 4:1011-1012.
Mette, et al. (1999) "Production of Aberrant Promoter Transcripts Contributes to Methylation and Silencing of Unlinked Homologous Promoters in trans," The EMBO Journal 18:241-248.
Meyer, P. (1995) "Understanding and Controlling Transgene Expression" TIBTECH 13:332-337.
Meyer, P. (1996) "Homology-Dependent Gene Silencing in Plants" Ann. Rev. Plant Physiol. Plant Mol. Biol. 47:23-48.
Montgomery, M.K. (1998) "Double-Stranded RNA as a Mediator in Sequence-Specific Genetic Silencing and Co-Suppression" TIG, vol. 14, No. 7:255-258.
Montgomery, M.K. et al. (1998) "RNA as a Target of Double-Stranded RNA-mediated Genetic Interference in *Caenorhabditis elegans*" PNAS vol. 95:15502-15507.
Moroni, Maria Cristina et al. (1992) "EGF-R Antisense RNA Blocks Expression of the Epidermal Growth Factor Receptor and Suppresses the Transforming Phenotype of a Human Carcinoma Cell Line" J. Bio. Chem., 267(4): 2714-2722.
Napoli, C., et al. (1990) "Introduction of a Chimeric Chalcone Synthase Gene into *Petunia* Results in Reversible Co-Suppression of Homologous Genes in trans" The Plant Cell 2(4): 279-289.
O'Brien et al. (2002) "Molecular Analysis of the Stylar-Expressed Solanum Chacoense Small Asparagine-rich Protein Family Related to the HT Modifier of Gametophytic Self-Incompatibility in *Nicotiana*" The Plant Journal 22:985-96.
Pang et al. (1996) "Post-transcriptional Transgene Silencing and Consequent Tospovirus Resistance in Trangenic Lettuce are Affected by Transgene Dosage and Plant Development" Plant J. 9:899-909.
Powell et al. (1990) "Protection Against Tobacco Mosaic Virus Infection in Transgenic Plants Requires Accumulation of Coat Protein Rather than Coat Protein RNA Sequences" Virology 175:124-130.
Powell-Abel et al. (1986) "Delay of Disease Development in Trangenic Plants that Express the Tobacco Mosaic Virus Coat Protein Gene" Science 232:738-743.
Proud et al. (1995) "PKR: a New Name and New Roles" TIBS 241-246.
Que, Q., et al., (1998) "Distinct Patterns of Pigment Suppression Are Produced by Allelic Sense and Antisense Chalcone Synthase Transgenes in *Petunia* Flowers" The Plant Journal 13:401-409.
Redenbaugh et al. (1992) "Safety Assessment of Genetically Engineered Fruits and Vegetables—A Case Study of the FlavrSavrTM Tomato," CRC Press, Boca Raton, FL.
Samuel et al. (2002) "Double-Jeopardy: Both Overexpression and Suppression of a Redox-Activated Plant Mitogen-Activated Protein Kinase Render Tobacco Plants Ozone Sensitive" The Plant Cell 14:2059-69.
Sanford, J.C., et al. (1985) "The Concept of Parasite-Derived Resistance-Deriving Resistance Genes from the Parasite's own Genome," J. Theor. Biol. 13:395-405.
Savin, K.W., et al. (1995) "Antisense ACC Oxidase RNA Delays Carnation Petal Senescence," Hortscience 30(5):970-972.
Schiebel, W. et al. (1993a) "RNA-directed RNA Polymerase from Tomato Leaves" The Journal of Biological Chemistry 268(16):11858-11867.
Schiebel, W. et al. (1993b) "RNA-directed RNA Polymerase from Tomato Leaves" The Journal of Biological Chemistry 268(16):11858-11867.
Sheehy, R.E. et al. (1998), "Reduction of Polygalacturonase Activity in Tomato Fruit by Antisense RNA" Proc. Natl. Acad. Sci, USA 85:8805-8809.
Smith, Neil et al. (1994) "Transgenic Plant Virus Resistance Mediated by Untranslatable Sense RNAs: Expression, Regulation, and Fate of Nonessential RNAs" Plant Cell 6:1441-1453.

Sullenger, B.A. et al. (1991) "Analysis of trans-Acting Response Decoy RNA-Mediated Inhibition of Human Immunodeficiency Virus Type 1 Transactivation" Journal of Virology 65(12): 6811-6816.

Sun et al., (1995) "Target Sequence-Specific Inhibition of HIV-1 Replication by Ribozymes Directed to tat RNA" Nucleic Acides Research 23:2909-2913.

Swaney, S. et al. (1995) "RNA-Mediated Resistance with Nonstructural Genes from the Tobacco Etch Virus Genome," MPMI 8(6):1005-1011.

Tabara, H., et al. (1998) "RNAi in *C. elegans*: Soaking in the Genome Sequence," Science 282(5388):430-431.

Takahashi et al. (1997) "Development of Necrosis and Activation of Disease Resistance in Transgenic Plants with Severely Reduced Catalase Levels" The Plant Journal 11:993-1005.

Thompson et al. (1995) "Improved Accumulation and Activity of Ribozyme Expressed From a tRNA-based RNA Polymerase III Promoter" Nucleic Acids Research 23:2259-2268.

Van Blokland et al. (1996) "Post-Transcriptional Suppression of Chalcone Synthase Genes in *Petunia hybrida* and the Accumulation of Unspliced pre-mRNA, Mechanisms and Applications of Gene Silencing".

Van Blokland, R. et al. (1994) "Transgene-mediated Suppression of Chalcone Synthase Expression in *Petunia hybrida* Results from an increase in RNA Turnover" The Plant Journal 6(6)861-877.

Van der Krol, A.R., et al. (1990) "Flavonoid Genes in *Petunia*: Addition of a Limited Number of Gene Copies May Lead to a Suppression of Gene Expression" The Plant Cell 2(4): 291-299.

Vaucheret et al. (1992) "Inhibition of Tobacco Nitrite Reductase, Activity by Expression of Antisense RNA" The Plant Journal 2:559-569.

Wassenegger and Pelissier (1998) "A Model for RNA-Mediated Gene Silencing in Higher Plants," Plant Mol. Biol. 37:349-362.

Wassenegger, Michael et al. (1999) "Signalling in gene silencing", Elsevier Science, 4(6): 207-209.

Weerasinghe et al. (1991) "Resistance to Human Immunodeficiency Virus Type 1 (HIV-1) Infection in Human CD4 Lymphocyte-Derived Cell Lines Conferred by Using Retroviral Vectors Expressing an HIV-1 RNA-Specific Ribozyme" Journal of Virology 65:5531-5534.

Xu, M., et al. (1989) "Immunoglobulin kappa gene expression after stable integration. II. Role of the intronic MAR and enhancer in transgenic mice," J Biol Chem.264(35):21190-5.

Yu et al. (1995) "In Vitro and in Vivo Characterization of a Second Functional Hairpin Ribozyme Against HIV-1" Virology 26:381-386.

Zhou et al. (1994) "Inhibition of HIV-1 in Human T-Lymphocytes by Retrovirally Transduced anti-tat and rev Hammerhead Ribozymes" Gene 149:33-39.

Zrenner et al. (1995) "Evidence of the Crucial Role of Sucrose Synthase for Sink Strength Using Transgenic Potato Plants" The Plant Journal 7:97-107.

* cited by examiner

SEQUENCE LISTING

```
<160> NUMBER OF SEQ ID NOS: 6

<210> SEQ ID NO 1
<211> LENGTH: 322
<212> TYPE: DNA
<213> ORGANISM: Artificial Sequence
<220> FEATURE:
<223> OTHER INFORMATION: Description of Artificial Sequence: Barley
      yellow dwarf virus  satellite RNA (minus strand)

<400> SEQUENCE: 1
tatccacgaa ataggaagtc gatcttttgc aagagtagcg aactcgttgc tctgtgaaag     60
attgatcgat tgtttcccgg tgtctcaagg tgcgtacctt gactgatgag tccgaaagga    120
cgaaacacca gtgttccagt gcgagcgaaa gctcgggctg aacaaacacg taaagcaagt    180
ctcctcattc gaaagagtgg tggccacctg gtggtgccac aattggagat ctttacttcg    240
gtggatttct gtatctattt gttggacgag gcaccagcct tctagtccgc gcggatacgt    300
```
cgtcagacag tacgcgctct gt                                              322

<210> SEQ ID NO 2
<211> LENGTH: 322
<212> TYPE: DNA
<213> ORGANISM: Artificial Sequence
<220> FEATURE:
<223> OTHER INFORMATION: Description of Artificial Sequence: Barley
      Yellow Dwarf virus sattelite RNA (positive strand)

<400> SEQUENCE: 2
acagagcgcg tactgtctga cgacgtatcc gcgcggacta gaaggctggt gcctcgtcca     60
acaaatagat acagaaatcc accgaagtaa agatctccaa ttgtggcacc accaggtggc    120
caccactctt tgaagtgagg agacttgctt tacgtgtttg ttcagcccga gctttcgctc    180
gcactggaac actggtgttt cgtcctttcg gactcatcag tcaaggtacg caccttgaga    240
caccgggaaa caatcgatca atctttcaca gagcaacgag ttcgctactc ttgcaaaaga    300
tcgacttcct atttcgtgga ta                                              322

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      oligonucleotide ; PCR primer SATPR1

<400> SEQUENCE: 3
cgcggatccg ttaacagagc gcgtactgtc tg                                    32

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:
      oligonucleotide PCR primer SATPR2

<400> SEQUENCE: 4
gccgagctca agtctcctca cttcaaag                                         28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      oligonucleoitde PCR primer SATPR2

<400> SEQUENCE: 5
gcgctgcagc tttacgtgtt tgttcagc                                         28

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      oligonucleotide PCR primer SATPR4

<400> SEQUENCE: 6
gcgggatccg atatccacga aataggaagt cg                                    32

METHODS AND MEANS FOR OBTAINING MODIFIED PHENOTYPES

This application is a divisional of U.S. Ser. No. 11/179,504, filed Jul. 13, 2005, now U.S. Pat. No. 8,183,217, issued May 22, 2012, a divisional of U.S. Ser. No. 10/152,808, filed May 23, 2002, now U.S. Pat. No. 7,138,565 B2, issued Nov. 21, 2006, which is a divisional of U.S. Ser. No. 09/373,720, filed Aug. 13, 1999, now U.S. Pat. No. 6,423,885 B2, issued Jul. 23, 2002, the contents of each of which are hereby incorporated by reference.

FIELD OF THE INVENTION

The invention relates to methods for reducing the phenotypic expression of a nucleic acid of interest in plant cells by providing aberrant RNA molecules, preferably unpolyadenylated RNA molecules comprising at least one target specific nucleotide sequence homologous to the nucleic acid of interest, preferably a sense strand, into the nucleus of plant cells. The target-specific unpolyadenylated RNA molecules may be provided by introduction of chimeric DNAs which when transcribed under control of conventional promoter and 3' end formation and polyadenylation regions yield RNA molecules wherein at least the polyadenylation signal may be removed by the autocatalytic activity of a self-splicing ribozyme comprised within the transcribed RNA molecules. Also provided are plant cells comprising such RNA molecules or chimeric DNA encoding such RNA molecules, as well as plants. Similar methods and means for reducing the phenotypic expression of a nucleic acid by co-suppression in eukaryotic cells are provided.

BACKGROUND OF THE INVENTION

Post-transcriptional gene silencing (PTGS) or co-suppression, is a common phenomenon associated with transgenes in transgenic plants. PTGS results in sequence-specific removal of the silenced transgene RNA as well as homologous endogenous gene RNA or viral RNA. It is characterized by low steady-state mRNA levels with normal (usually high) rates of nuclear transcription of transgenes being maintained. There are a number of common features or characteristics for PTGS. PTGS is sequence-specific;
systemically transmissible;
often associated with the presence of multiple copies of transgenes or with the use of strong promoters;
frequently correlated with the presence of repetitive DNA structures, including inverted repeat T-DNA insertion patterns;
often accompanied by de novo DNA methylation in the transcribed
region, and
may be meiotically reset.

A number of hypothetical models have been proposed to explain PTGS (see e.g. Wassenegger and Pélissier, 1998). Typically, these models suggest the involvement of a host encoded enzyme (RNA-directed RNA polymerase (RdRP)) which is proposed to use aberrant RNA as templates to synthesize small copy RNA molecules (CRNA). These cRNAs would then hybridize with the target mRNA to form duplex structures, thereby rendering the mRNA susceptible to degradation by endoribonucleases. So far, there has been no direct evidence that RdRP is involved in PTGS in plants.

An important question arising from the existing models is what type of RNA is the aberrant RNA that would be used as a template by RdRP, and in which cellular compartment RdRP would function.

Several reports have described the accumulation of unproductive or unpolyadenylated transgene RNA in plants which are post-transcriptionally silenced (Lee et al. 1997; van Eldik et al. 1998; Covey et al., 1997; van Houdt et al., 1997; Metzlaff et al.; 1997).

The following documents relate to methods and means for regulating or inhibiting gene expression in a cell.

U.S. Pat. No. 5,190,131 and EP 0 467 349 A1 describe methods and means to regulate or inhibit gene expression in a cell by incorporating into or associating with the genetic material of the cell a non-native nucleic acid sequence which is transcribed to produce an mRNA which is complementary to and capable of binding to the mRNA produced by the genetic material of that cell.

EP 0 223 399 A1 describes methods to effect useful somatic changes in plants by causing the transcription in the plant cells of negative RNA strands which are substantially complementary to a target RNA strand. The target RNA strand can be a mRNA transcript created in gene expression, a viral RNA, or other RNA present in the plant cells. The negative RNA strand is complementary to at least a portion of the target RNA strand to inhibit its activity in vivo.

EP 0 240 208 describes a method to regulate expression of genes encoded for in plant cell genomes, achieved by integration of a gene under the transcriptional control of a promoter which is functional in the host and in which the transcribed strand of DNA is complementary to the strand of DNA that is transcribed from the endogenous gene(s) one wishes to regulate.

EP 0 647 715 A1 and U.S. Pat. Nos. 5,034,323, 5,231,020 and 5,283,184 describe methods and means for producing plants exhibiting desired phenotypic traits, by selecting transgenotes that comprise a DNA segment operably linked to a promoter, wherein transcription products of the segment are substantially homologous to corresponding transcripts of endogenous genes, particularly endogenous flavonoid biosynthetic pathway genes.

Waterhouse et al. 1998 describe that virus resistance and gene silencing in plants can be induced by simultaneous expression of sense and anti-sense-RNA. The sense and anti-sense RNA may be located in one transcript that has self-complementarity.

Hamilton et al. 1998 describes that a transgene with repeated DNA, i.e. inverted copies of its 5' untranslated region, causes high frequency, posttranscriptional suppression of ACC-oxidase expression in tomato.

WO 98/53083 describes constructs and methods for enhancing the inhibition of a target gene within an organism which involve inserting into the gene silencing vector an inverted repeat sequence of all or part of a polynucleotide region within the vector.

WO 95/34688 describes methods for cytoplasmic inhibition of gene expression and provides genetic constructs for the expression of inhibitory RNA in the cytoplasm of eukaryotic cells. The inhibitory RNA may be an anti-sense or a co-suppressor RNA. The genetic constructs are capable of replicating in the cytoplasm of a eukaryotic cell and comprise a promoter region, which may be a plant virus subgenomic promoter in functional combination with the RNA encoding region.

WO95/15394 and U.S. Pat. No. 5,908,779 describe a method and construct for regulating gene expression through inhibition by nuclear antisense RNA in (mouse) cells. The construct comprises a promoter, antisense sequences, and a cis- or trans-ribozyme which generates 3'-ends independently of the polyadenylation machinery and thereby inhibits the transport of the RNA molecule to the cytoplasm.

SUMMARY OF THE INVENTION

The present invention provides a method for reducing the phenotypic expression of a nucleic acid of interest, which is normally capable of being expressed in a plant cell, the method comprising the step of providing to the nucleus of that plant cell aberrant RNA comprising a target-specific nucleotide sequence, preferably unpolyadenylated RNA comprising a target specific nucleotide sequence, particularly by producing aberrant RNA such as unpolyadenylated RNA by transcription of a chimeric DNA comprised within the plant cell, the chimeric DNA comprising a plant-expressible promoter operably linked to a target specific DNA region encoding that RNA and optionally further comprising a DNA region involved in 3' end formation and polyadenylation, preceded by a self-splicing ribozyme encoding DNA region.

The invention also provides a method for reducing the phenotypic expression of a nucleic acid of interest, which is normally capable of being expressed in a plant cell, the method comprising the step of introducing into the nuclear genome of the plant cell a chimeric DNA to generate a transgenic plant cell, the chimeric DNA comprising the following operably linked parts:

a plant-expressible promoter region, preferably a constitutive promoter or an inducible promoter or a tissue-specific promoter;
a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;
a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, Neurospora VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and
a) a DNA region involved in 3' end formation and polyadenylation;
wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed. Optionally, a transgenic plant may be regenerated from the transgenic plant cell. Preferably, the DNA region encoding a self-splicing ribozyme is located immediately upstream of the DNA region involved in 3' end formation and polyadenylation.

It is another objective of the invention to provide a chimeric DNA molecule for reducing the phenotypic expression of a nucleic acid of interest, which is normally capable of being expressed in a plant cell, comprising a plant-expressible promoter region, preferably a constitutive promoter or an inducible promoter or a tissue-specific promoter;
a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;
a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, Neurospora VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and
a DNA region involved in 3' end formation and polyadenylation; wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed. Preferably, the DNA region encoding a self-splicing ribozyme is located immediately upstream of the DNA region involved in 3' end formation and polyadenylation.

It is yet another objective of the invention to provide plant cells and plants comprising a nucleic acid of interest which is normally capable of being phenotypically expressed, further comprising a chimeric DNA, preferably stably-integrated into the nuclear genome, comprising a plant-expressible promoter region, preferably a constitutive promoter or an inducible promoter or a tissue-specific promoter;
a target-specific DNA region encoding a target-specific nucleotide sequence, preferably a target-specific DNA region comprising a nucleotide sequence of at least 10 consecutive nucleotides having at least about 70% sequence identity to about 100% sequence identity to the nucleic acid of interest or comprising a nucleotide sequence of at least 10 consecutive nucleotides having at least about 70% sequence identity to about 100% sequence identity to the complement of said nucleic acid of interest;
a DNA region encoding a self-splicing ribozyme, preferably a self-splicing ribozyme comprising a cDNA copy of a self-splicing ribozyme from avocado sunblotch viroid, peach latent mosaic viroid, Chrysanthemum chlorotic mottle viroid, carnation stunt associated viroid, Newt satellite 2 transcript, Neurospora VS RNA, barley yellow dwarf virus satellite RNA, arabis mosaic virus satellite RNA, chicory yellow mottle virus satellite RNA S1, lucerne transient streak virus satellite tobacco ringspot virus satellite RNA, subterranean clover mottle virus satellite RNA, solanum nodiflorum mottle virus satellite RNA, velvet tobacco mottle virus satellite RNA, Cherry small circular viroid-like RNA or hepatitis delta virus RNA, particularly a DNA region comprising the nucleotide sequence of SEQ ID No 1 or SEQ ID No 2 or a ribozyme-effective part thereof; and a DNA region involved in 3' end formation and polyadenylation;

wherein said chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

The invention also provides a method for identifying a phenotype associated with the expression of a nucleic acid of interest in a plant cell, the method comprising:
1) selecting within the nucleic acid of interest a target sequence of at least 5 consecutive nucleotides;
2) introducing a chimeric DNA into the nucleus of a suitable plant host cell comprising the nucleic acid of interest, the chimeric DNA comprising the following operably linked DNA fragments:
   a) a plant-expressible promoter region;
   b) a target-specific DNA region comprising a nucleotide sequence of at least about 70% to about 100% sequence identity to said target sequence or to the complement of said target sequence; followed by
   c) a DNA region encoding a self-splicing ribozyme located immediately upstream of
   d) a DNA region involved in 3' end formation and polyadenylation;
3) observing the phenotype by a suitable method.

Yet another objective of the invention is to provide a method for reducing the phenotypic expression of a nucleic acid of interest, which is normally capable of being expressed in a eukaryotic cell, the method comprising the step of providing to the nucleus of said eukaryotic cell aberrant RNA, preferably unpolyadenylated RNA, comprising a target specific nucleotide sequence of at least 10 consecutive nucleotides with at least about 70% sequence identity to about 100% sequence identity to the nucleotide sequence of the nucleic acid of interest, pariticularly by producing aberrant RNA such as unpolyadenylated RNA by transcription of a chimeric DNA comprised within the eukaryotic cell, the chimeric DNA comprising a plant-expressible promoter operably linked to a target specific DNA region encoding that RNA and optionally further comprising a DNA region involved in 3' end formation and polyadenylation, preceded by a self-splicing ribozyme encoding DNA region.

Still another objective of the invention is to provide a method for reducing the phenotypic expression of a nucleic acid of interest, which is normally capable of being expressed in a eukaryotic cell, comprising the step of introducing into the nuclear genome of the eukaryotic cell a chimeric DNA to generate a transgenic plant cell, comprising the following operably linked parts:
   a) a promoter region functional in the eukaryotic cell;
   b) a target-specific DNA region comprising nucleotide sequence of at least 10 consecutive nucleotides with at least about 70% sequence identity to about 100% sequence identity to the nucleotide sequence of the nucleic acid of interest;
   c) a DNA region encoding a self-splicing ribozyme; and
   d) a DNA region involved in 3' end formation and polyadenylation wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

The invention also provides a eukaryotic cell comprising a nucleic acid of interest, normally capable of being phenotypically expressed, further comprising a chimeric DNA comprising the following operably linked parts:
a promoter region functional in the eukaryotic cell;
a target-specific DNA region comprising nucleotide sequence of at least 10 consecutive nucleotides with at least about 70% sequence identity to about 100% sequence identity to the nucleotide sequence of the nucleic acid of interest;
a DNA region encoding a self-splicing ribozyme; and
a DNA region involved in 3' end formation and polyadenylation wherein said chimeric DNA when transcribed in the eukaryotic cell produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed, as well as non-human eukaryotic organisms comprising or consisting essentially of such eukaryotic cells.

DETAILED DESCRIPTION OF THE PREFERRED EMBODIMENTS OF THE INVENTION

Figure 1:
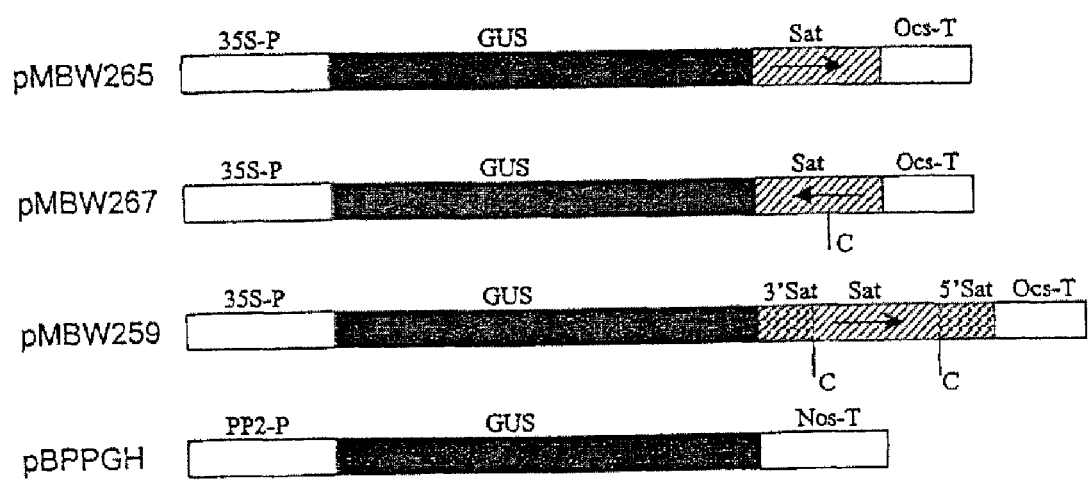
FIG. 1. Schematic representation of the ribozyme-containing GUS chimeric gene (pMBW267 and pMBW259) the control construct (pMBW 265) and the GUS chimeric gene used for supertransformation (pBPPGH). 35s-P: CaMV 35S promoter; GUS: region encoding β-glucuronidase; SAT: cDNA copy of the satellite RNA of Barley Yellow Dwarf Virus (BYDV) in positive strand orientation (–) or in minus strand orientation (–); Ocs-T: region from the octopine synthase gene from Agrobacterium involved in 3' end formation and polyadenylation; 3' Sat: cDNA copy of the 3' end of the satellite RNA of BYDV; 5' SAT: cDNA copy of the 5' end of the satellite RNA of BYDV; PP2-P: 1.3 kb promoter region of a gene encoding the cucurbit phloem protein PP2; Nos-T: region from the nopaline synthase gene from Agrobacterium involved in 3' end formation and polyadenylation; C: autocatalytic cleavage site in the RNA molecule transcribed from the chimeric gene.

Although gene-silencing, either by anti-sense RNA or through co-suppression using sense RNA, is a commonly observed phenomenon in transgenic-research, the intentional generation of gene-silenced transgenic eukaryotic cells and transgenic organisms, particularly plant cells and plants, still faces a number of problems. In particular the efficiency of gene-silencing is still amenable to improvement, both in number of transgenic lines exhibiting the phenomenon as well as in the level of reduction of transcription and ultimately the phenotypic expression of particular nucleic acid of interest in a particular transgenic line.

A number of improved methods for gene-silencing have already been described, e.g. the simultaneous use in one cell of anti-sense and sense RNA targeted to the nucleic acid of interest, preferably co-located on one transcript exhibiting self-complementarity. Novel methods for increasing the efficiency of gene-silencing, preferably gene-silencing through co-suppression in a eukaryotic cell or organism, preferably plant cell or plant, and means therefore, are described in the different embodiments provided by the specification and claims.

The current invention is based on the unexpected observation by the inventors, that the provision or the introduction of aberrant target-specific RNA, preferably unpolyadenylated target-specific RNA, particularly an aberrant target-specific RNA comprising a nucleotide sequence essentially identical to the nucleic acid of interest in sense orientation, into the nucleus of a cell of a eukaryotic organism, particularly a cell of plant, resulted in an efficient reduction of the expression of the nucleic acid of interest, both in the level of reduction as well as in the number of transgenic lines exhibiting gene-silencing. The understanding of hypothetical mechanisms through which gene-silencing, particularly PTGS, is supposed to proceed did not allow to predict that among all variables potentially involved in initiation and maintenance of gene-silencing, the selection of this one parameter—i.e. providing aberrant, preferably unpolyadenylated RNA—would have been sufficient to significantly increase the efficiency of gene-silencing, particularly gene-silencing through co-suppression.

In one embodiment of the invention, a method is provided for reducing the phenotypic expression of a nucleic acid of interest, which is normally capable of being expressed in a plant cell, comprising the step of providing aberrant RNA such as unpolyadenylated RNA which includes a target-specific nucleotide sequence to the nucleus of that plant cell. Conveniently, the aberrant RNA such as unpolyadenylated RNA including the target-specific nucleotide sequence may be produced by transcription of a chimeric DNA or chimeric gene comprised within the plant cell, preferably incorporated, particularly stably integrated into the nuclear genome of the plant cell. In a particularly preferred embodiment, the aberrant RNA is unpolyadenylated RNA which, still exhibits other modifications characteristic of mRNA, such as, but not limited to, the presence of a cap-structure at the 5' end.

As used herein, the term "expression of a gene" refers to the process wherein a DNA region which is operably linked to appropriate regulatory regions, particularly to a promoter region, is transcribed into an RNA which is biologically active i.e., which is either capable of interaction with another nucleic acid or which is capable of being translated into a polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a protein or polypeptide.

A nucleic acid of interest is "capable of being expressed", when said nucleic acid, when introduced in a suitable host cell, particularly in a plant cell, can be transcribed (or replicated) to yield an RNA, and/or translated to yield a polypeptide or protein in that host cell.

The term "gene" means any DNA fragment comprising a DNA region (the "transcribed DNA region") that is transcribed into a RNA molecule (e.g., a mRNA) in a cell operably linked to suitable regulatory regions, e.g., a plant-expressible promoter. A gene may thus comprise several operably linked DNA fragments such as a promoter, a 5' leader sequence, a coding region, and a 3' region comprising a polyadenylation site. A plant gene endogenous to a particular plant species (endogenous plant gene) is a gene which is naturally found in that plant species or which can be introduced in that plant species by conventional breeding. A chimeric gene is any gene which is not normally found in a plant species or, alternatively, any gene in which the promoter is not associated in nature with part or all of the transcribed DNA region or with at least one other regulatory region of the gene.

As used herein, "phenotypic expression of a nucleic acid of interest" refers to any quantitative trait associated with the molecular expression of a nucleic acid in a host cell and may thus include the quantity of RNA molecules transcribed or replicated, the quantity of post-transcriptionally modified RNA molecules, the quantity of translated peptides or proteins, the activity of such peptides or proteins.

A "phenotypic trait" associated with the phenotypic expression of a nucleic acid of interest refers to any quantitative or qualitative trait, including the trait mentioned, as well as the direct or indirect effect mediated upon the cell, or the organism containing that cell, by the presence of the RNA molecules, peptide or protein, or posttranslationally modified peptide or protein. The mere presence of a nucleic acid in a host cell, is not considered a phenotypic expression or a phenotypic trait of that nucleic acid, even though it can be quantitatively or qualitatively traced. Examples of direct or indirect effects mediated on cells or organisms are, e.g., agronomically or industrial useful traits, such as resistance to a pest or disease; higher or modified oil content etc.

As used herein, "reduction of phenotypic expression" refers to the comparison of the phenotypic expression of the nucleic acid of interest to the eukaryotic cell in the presence of the RNA or chimeric genes of the invention, to the phenotypic expression of the nucleic acid of interest in the absence of the RNA 10 or chimeric genes of the invention. The phenotypic expression in the presence of the chimeric RNA of the invention should thus be lower than the phenotypic expression in absence thereof, preferably be only about 25%, particularly only about 10%, more particularly only about 5% of the phenotypic expression in absence of the chimeric RNA, especially the phenotypic expression should be completely inhibited for all practical purposes by the presence of the chimeric RNA or the chimeric gene encoding such an RNA.

A reduction of phenotypic expression of a nucleic acid where the phenotype is a qualitative trait means that in the presence of the chimeric RNA or gene of the invention, the phenotypic trait switches to a different discrete state when compared to a situation in which such RNA or gene is absent. A reduction of phenotypic expression of a nucleic acid may thus, a.o., be measured as a reduction in transcription of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a nucleic acid of interest, may be accompanied by or correlated to an increase in a phenotypic trait.

As used herein "a nucleic acid of interest" or a "target nucleic acid" refers to any particular RNA molecule or DNA sequence which may be present in a eukaryotic cell, particularly a plant cell.

As used herein "aberrant RNA" refers to polyribonucleotide molecules which have characteristic differing from mRNA molecules normally found in that cell. The different characteristics include but are not limited to the absence or removal of a 5' cap structure, presence of persistent introns e.g. introns which have been modified in their splice sites so as to prevent splicing, or the absence of the polyA tail normally found associated with the mRNA ("unpolyadenylated RNA").

The term "target-specific nucleotide sequence" as used herein, refers to a nucleotide sequence (either DNA or RNA nucleotide sequence depending on the context) which can reduce the expression of the target nucleic acid of interest by gene-silencing. Preferably, only the expression of the target nucleic acid or gene, or nucleic acids or genes comprising essentially similar nucleotide sequence is reduced.

Preferably the target-specific nucleotide sequence comprises a nucleotide sequence corresponding to the "sense" nucleotide sequence of the nucleic acid or gene of interest. In other words, a target-specific sense nucleotide sequence may be essentially similar to part of an RNA molecule transcribed or produced from the nucleic acid or gene of interest or to parts of the nucleic acid or gene of interest controlling the production of that transcribed or produced RNA molecule, when read in the same 5' to 3' direction as the transcribed or produced RNA molecule.

Preferably, the target specific nucleotide sequence corresponds to part of a nucleic acid region from which RNA is produced, particularly a region which is transcribed and translated. It is particularly preferred that the target sequence corresponds to one or more consecutive exons, more particularly is located within a single exon of a coding region. However, the target specific nucleotide sequence may also be corresponding to untranslated regions of the RNA molecule produced from the nucleic acid or gene of interest. Moreover, in the light of a recent publication by Mette et al. (1999), it is expected that the target specific nucleotide sequence may also correspond to the regions controlling the production or transcription of RNA from the nucleotide or gene of interest, such as the promoter region.

The length of the sense target-specific nucleotide sequence may vary from about 10 nucleotides (nt) up to a length equaling the length (in nucleotides) of the target nucleic acid. Preferably the total length of the sense nucleotide sequence is at least 10 nt, preferably 15 nt, particularly at least about 50 nt, more particularly at least about 100 nt, especially at least about 150 nt, more especially at least about 200 nt, quite especially at least about 550 nt. It is expected that there is no upper limit to the total length of the sense nucleotide sequence, other than the total length of the target nucleic acid. However for practical reason (such as e.g. stability of the chimeric genes) it is expected that the length of the sense nucleotide sequence should not exceed 5000 nt, particularly should not exceed 2500 nt and could be limited to about 1000 nt.

It will be appreciated that the longer the total length of the sense nucleotide sequence is, the less stringent the requirements for sequence identity between the total sense nucleotide sequence and the corresponding sequence in the target nucleic acid or gene become. Preferably, the total sense nucleotide sequence should have a sequence identity of at least about 75% with the corresponding target sequence, particularly at least about 80%, more particularly at least about 85%, quite particularly about 90%, especially about 95%, more especially about 100%, quite especially be identical to the corresponding part of the target nucleic acid. However, it is preferred that the sense nucleotide sequence always includes a sequence of about 10 consecutive nucleotides, particularly about 20 nt, more particularly about 50 nt, especially about 100 nt, quite especially about 150 nt with 100% sequence identity to the corresponding part of the target nucleic acid. Preferably, for calculating the sequence identity and designing the corresponding sense sequence, the number of gaps should be minimized, particularly for the shorter sense sequences.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA). Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

It is expected however, that the target-specific nucleotide sequence may also comprise a nucleotide sequence corresponding to the "antisense" nucleotide sequence of the nucleic acid or gene of interest. In other words, a target-specific antisense nucleotide sequence may be essentially similar to the complement of part of an RNA molecule transcribed or produced from the nucleic acid or gene of interest or to the complement of parts of the nucleic acid or gene of interest controlling the production of that transcribed or produced RNA molecule, when read in the same 5' to 3' direction as the transcribed or produced RNA molecule.

The requirements for antisense target-specific nucleotide sequences with regard to length, similarity etc. are expected to be essentially similar as for sense target-specific nucleotide sequences as specified herein.

It will be clear to the person skilled in the art that the unpolyadenylated RNA molecule may comprise more than one target-specific nucleotide sequence and particularly that the unpolyadenylated RNA molecule may comprise sense and antisense target-specific nucleotide sequences wherein the sense and antisense nucleotide sequences are essentially complementary to each other and capable of forming an artificial hairpin structure as described in Waterhouse et at., 1998 or in PCT-application PCT/IB99/00606 (incorporated by reference). "Hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA."

Thus, it will be clear to the person skilled in the art that the constructs of examples 4-8 hereinbelow which produce target-specific hairpin RNA may be modified to produce unpolyadenylated target-specific hairpin RNA when transcribed. Provision of unpolyadenylated target-specific hairpin RNA into the nucleus of a cell of a eukaryotic organism would result in an efficient reduction of the expression of the nucleic acid of interest, both in the level of reduction as well as in the number of transgenic lines exhibiting gene-silencing. Providing aberrant, preferably unpolyadenylated hairpin RNA would be sufficient to significantly increase the efficiency of gene-silencing.

As indicated above, introduction of target-specific unpolyadenylated RNA into the nucleus of a plant cell can conveniently be achieved by transcription of a chimeric DNA encoding RNA introduced into the nucleus, preferably stably integrated into the nuclear genome of a plant cell.

In a preferred embodiment of the invention, the target-specific unpolyadenylated RNA may be produced in the nucleus of a plant cell by transcription of a chimeric DNA encoding a first target-specific RNA, which may be further processed by the action of a ribozyme also present, and preferably also encoded by a chimeric gene, in the plant cell to yield a second unpolyadenylated target-specific RNA. It will be clear for the person skilled in the art that the RNA processing need not be subsequently but can occur simultaneously. In a particularly preferred embodiment the ribozyme is a self-splicing ribozyme which is comprised within the generated target specific RNA transcript.

Thus, in a particularly preferred embodiment of the invention, a method is provided for reducing the phenotypic expression of a nucleic acid of interest, which is normally capable of being expressed in a plant cell, the method comprising the step of introducing into the nuclear genome of the plant cell a chimeric DNA to generate a transgenic plant cell, the chimeric DNA comprising the following operably linked parts:
  (a) a plant-expressible promoter region;
  (b) a target-specific DNA region;
  (c) a DNA region encoding a self-splicing ribozyme; and
  (d) a DNA region involved in 3' end formation and polyadenylation
    wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

The method may optionally further comprise the step of regenerating a the transgenic plant cell into a transgenic plant.

As used herein, "a ribozyme" is a catalytic RNA molecule that has the intrinsic ability to break and form covalent bonds in ribonucleic acids at specific sites in the absence of a cofactor other than a divalent cation.

As used herein a "self-splicing ribozyme" or "self-cleaving ribozyme" is a ribozyme capable of autocatalysis at a specific site within that ribozyme. Preferred self-splicing ribozymes are self-splicing ribozymes with a so-called hammerhead structure. However, it is expected that self-cleaving ribozymes with another conformation such as the hairpin self-cleaving structures encountered in the minus strand of replication intermediates of e.g. the nepoviruses can also be used to the same effect.

Particularly preferred self-splicing ribozymes are those involved in the replication of small circular plant pathogenic RNAs, such as but not limited to the self-splicing ribozyme from avocado sunblotch viroid, peach latent mosaic viroid, Chrysanthemum chlorotic mottle viroid, carnation stunt associated viroid, Newt satellite 2 transcript, Neurospora VS RNA, barley yellow dwarf virus satellite RNA, arabis mosaic virus satellite RNA, chicory yellow mottle virus satellite RNA S1, lucerne transient streak virus satellite RNA, tobacco ringspot virus satellite RNA, subterranean clover mottle virus satellite RNA, solanum nodiflorum mottle virus satellite RNA, velvet tobacco mottle virus satellite RNAvSCMoV or Cherry small circular viroid-like RNAcscRNAl. Table 1 lists different variant ribozymes suitable for the invention, as well as a reference to their nucleotide sequence.

The DNA regions encoding self-splicing ribozymes may be cDNA copies of part of the mentioned plant pathogenic RNAs comprising the ribozyme, or may be synthetic DNA. Also comprised are variants such as mutants including substitutions, deletions or insertions of nucleotides within the ribozyme nucleotide sequence in such a way that the autocatalytic capacity of the ribozymes is not substantially altered.

Preferably, the DNA region encoding the self-splicing ribozyme is located immediately upstream of the DNA region encoding the 3' end formation and polyadenylation signal. However, having read the specification, the person skilled in the art will immediately realize that the DNA region encoding the self-splicing ribozyme may be comprised within the chimeric gene encoding the unpolyadenylated RNA at other locations, provided that a sufficiently large second RNA comprising a target-specific nucleotide wherein the polyadenylation site is removed may be generated.

TABLE 1

Different self-cleaving ribozymes

| RNA Species | Reference | | | Accession Nr | (+) strand | (−) strand |
|---|---|---|---|---|---|---|
| Avocado sunblotch viroid | Symons | 1981 | Nucleic Acids Res. 9 6527-6537 | J02020 | hammerhead | hammerhead |
| Avocado sunblotch viroid variant C-10 | Rakowski and Symons | 1989 | Virology 173 352-356 | M31100 | hammerhead | hammerhead |
| Avocado sunblotch viroid variant B-1 | Rakowski and Symons | 1989 | Virology 173 352-356 | M31086 | hammerhead | hammerhead |
| Avocado sunblotch viroid variant A-2 | Rakowski and Symons | 1989 | Virology 173 352-356 | M31085 | hammerhead | hammerhead |
| Avocado sunblotch viroid variant B-2 | Rakowski and Symons | 1989 | Virology 173 352-356 | M31087 | hammerhead | hammerhead |
| Avocado sunblotch viroid variant C-2 | Rakowski and Symons | 1989 | Virology 173 352-356 | M31092 | hammerhead | hammerhead |
| Avocado sunblotch viroid variant B-3 | Rakowski and Symons | 1989 | Virology 173 352-356 | M31088 | hammerhead | hammerhead |
| Avocado sunblotch viroid variant C-3 | Rakowski and Symons | 1989 | Virology 173 352-356 | M31093 | hammerhead | hammerhead |

TABLE 1-continued

Different self-cleaving ribozymes

| RNA Species | Reference | | | Accession Nr | (+) strand | (−) strand |
|---|---|---|---|---|---|---|
| Avocado sunblotch viroid variant B-4 | Rakowski and Symons | 1989 | Virology 173 352-356 | M31089 | hammerhead | hammerhead |
| Avocado sunblotch viroid variant C-4 | Rakowski and Symons | 1989 | Virology 173 352-356 | M31094 | hammerhead | hammerhead |
| Avocado sunblotch viroid variant B-5 | Rakowski and Symons | 1989 | Virology 173 352-356 | M31090 | hammerhead | hammerhead |
| Avocado sunblotch viroid variant C-5 | Rakowski and Symons | 1989 | Virology 173 352-356 | M31095 | hammerhead | hammerhead |
| Avocado sunblotch viroid variant B-6 | Rakowski and Symons | 1989 | Virology 173 352-356 | M31091 | hammerhead | hammerhead |
| Avocado sunblotch viroid variant C-6 | Rakowski and Symons | 1989 | Virology 173 352-356 | M31096 | hammerhead | hammerhead |
| Avocado sunblotch viroid variant C-7 | Rakowski and Symons | 1989 | Virology 173 352-356 | M31097 | hammerhead | hammerhead |
| Avocado sunblotch viroid variant C-8 | Rakowski and Symons | 1989 | Virology 173 352-356 | M31098 | hammerhead | hammerhead |
| Avocado sunblotch viroid variant C-9 | Rakowski and Symons | 1989 | Virology 173 352-356 | M31099 | hammerhead | hammerhead |
| Avocado sunblotch viroid ASBVd-B | Semancik and Szychowski | 1994 | J. Gen Virol. 75 1543-1549 | S74687 | hammerhead | hammerhead |
| Avocado sunblotch viroid ASBVd-V | Semancik and Szychowski | 1994 | J. Gen Virol. 75 1543-1549 | S73861 | hammerhead | hammerhead |
| Peach latent mosaic viroid PLMVd.1 | Hernandez and Flores | 1992 | Proc. Natl. Acad. Sci. 89 3711-3715 | M83545 | hammerhead | hammerhead |
| Peach latent mosaic viroid PLMVd.2 | Hernandez and Flores | 1992 | Proc. Natl. Acad. Sci. 89 3711-3715 | | hammerhead | hammerhead |
| Peach latent mosaic viroid Peach-Italy | Schamloul et al. | 1995 | Acta Hortic. 386 522-530 | | hammerhead | hammerhead |
| Peach latent mosaic viroid Cherry-Canada | Hadini et al. | 1997 | Plant Dis. 81, 154-158 | | hammerhead | hammerhead |
| Peach latent mosaic viroid variant gds2 | Ambros et al. | 1998 | J. Virol. 72 7397-7406 | AJ005294 | hammerhead | hammerhead |
| Peach latent mosaic viroid variant gds21 | Ambros et al. | 1998 | J. Virol. 72 7397-7406 | AJ005295 | hammerhead | hammerhead |
| Peach latent mosaic viroid variant gds15 | Ambros et al. | 1998 | J. Virol. 72 7397-7406 | AJ005296 | hammerhead | hammerhead |
| Peach latent mosaic viroid variant gds23 | Ambros et al. | 1998 | J. Virol. 72 7397-7406 | AJ005297 | hammerhead | hammerhead |
| Peach latent mosaic viroid variant gds18 | Ambros et al. | 1998 | J. Virol. 72 7397-7406 | AJ005298 | hammerhead | hammerhead |
| Peach latent mosaic viroid variant gds1 | Ambros et al. | 1998 | J. Virol. 72 7397-7406 | AJ005299 | hammerhead | hammerhead |
| Peach latent mosaic viroid variant gds3 | Ambros et al. | 1998 | J. Virol. 72 7397-7406 | AJ005300 | hammerhead | hammerhead |
| Peach latent mosaic viroid variant gds19 | Ambros et al. | 1998 | J. Virol. 72 7397-7406 | AJ005301 | hammerhead | hammerhead |
| Peach latent mosaic viroid variant gds13 | Ambros et al. | 1998 | J. Virol. 72 7397-7406 | AJ005302 | hammerhead | hammerhead |
| Peach latent mosaic viroid variant gds6 | Ambros et al. | 1998 | J. Virol. 72 7397-7406 | AJ005303 | hammerhead | hammerhead |
| Peach latent mosaic viroid variant gds16 | Ambros et al. | 1998 | J. Virol. 72 7397-7406 | AJ005304 | hammerhead | hammerhead |
| Peach latent mosaic viroid variant esc8 | Ambros et al. | 1998 | J. Virol. 72 7397-7406 | AJ005305 | hammerhead | hammerhead |
| Peach latent mosaic viroid variant esc16 | Ambros et al. | 1998 | J. Virol. 72 7397-7406 | AJ005306 | hammerhead | hammerhead |
| Peach latent mosaic viroid variant esc5 | Ambros et al. | 1998 | J. Virol. 72 7397-7406 | AJ005307 | hammerhead | hammerhead |
| Peach latent mosaic viroid variant esc12 | Ambros et al. | 1998 | J. Virol. 72 7397-7406 | AJ005308 | hammerhead | hammerhead |
| Peach latent mosaic viroid variant esc 10 | Ambros et al. | 1998 | J. Virol. 72 7397-7406 | AJ005309 | hammerhead | hammerhead |
| Peach latent mosaic viroid variant esc 14 | Ambros et al. | 1998 | J. Virol. 72 7397-7406 | AJ005310 | hammerhead | hammerhead |
| Peach latent mosaic viroid variant ls4b | Ambros et al. | 1998 | J. Virol. 72 7397-7406 | AJ005311 | hammerhead | hammerhead |
| Peach latent mosaic viroid variant ls16b | Ambros et al. | 1998 | J. Virol. 72 7397-7406 | AJ005312 | hammerhead | hammerhead |
| Peach latent mosaic viroid variant ls17b | Ambros et al. | 1998 | J. Virol. 72 7397-7406 | AJ005313 | hammerhead | hammerhead |
| Peach latent mosaic viroid variant ls1 | Ambros et al. | 1998 | J. Virol. 72 7397-7406 | AJ005314 | hammerhead | hammerhead |
| Peach latent mosaic viroid variant ls18b | Ambros et al. | 1998 | J. Virol. 72 7397-7406 | AJ005315 | hammerhead | hammerhead |
| Peach latent mosaic viroid variant ls11 | Ambros et al. | 1998 | J. Virol. 72 7397-7406 | AJ005316 | hammerhead | hammerhead |
| Peach latent mosaic viroid variant ls8 | Ambros et al. | 1998 | J. Virol. 72 7397-7406 | AJ005317 | hammerhead | hammerhead |
| Peach latent mosaic viroid variant ls19b | Ambros et al. | 1998 | J. Virol. 72 7397-7406 | AJ005318 | hammerhead | hammerhead |
| Peach latent mosaic viroid variant ls5b | Ambros et al. | 1998 | J. Virol. 72 7397-7406 | AJ005319 | hammerhead | hammerhead |
| Peach latent mosaic viroid variant ls11b | Ambros et al. | 1998 | J. Virol. 72 7397-7406 | AJ005320 | hammerhead | hammerhead |
| Peach latent mosaic viroid variant ls6b | Ambros et al. | 1998 | J. Virol. 72 7397-7406 | AJ005321 | hammerhead | hammerhead |
| Peach latent mosaic viroid variant ls14b | Ambros et al. | 1998 | J. Virol. 72 7397-7406 | AJ005322 | hammerhead | hammerhead |
| Crysanthemum cholorotic mottle viroid | Navarro and Flores | 1997 | Proc. Natl. Acad. Sci. 94 11262-11267 | Y14700 | hammerhead | hammerhead |
| Barley yellow dwarf virus satellite RNA | Miller et al. | 1991 | Virology 183 711-720 | M63666 | hammerhead | hammerhead |
| Arabis mosaic virus satellite RNA | Kaper et al. | 1988 | Biochem. Biophys. Res. Com. 154 318-325 | M21212 | hammerhead | hairpin |
| Chicory yellow mottle virus satellite RNA S1 | Rubino et al. | 1990 | J. Gen Virol. 71 1897-1903 | D00721 | hammerhead | hairpin |
| Lucerne transient streak virus satellite RNA LTSV-N | Keese et al. | 1983 | FEBS let. 159 185-190 | X01985 | hammerhead | hammerhead |
| Lucerne transient streak virus satellite RNA LTSV-A | Keese et al. | 1983 | FEBS let. 159 185-190 | X01984 | hammerhead | hammerhead |
| Lucerne transient streak virus satellite RNA LTSV-C | Abouhaidar and Pallwal | 1988 | J. Gen. Virology 69 2369-2373 | D00341 | hammerhead | hammerhead |
| Tobacco ringspot virus satellite RNA.1 | Buzayan et al. | 1986 | Virology 151, 186-199 | M14879 | hammerhead | hairpin |
| Tobacco ringspot virus satellite RNA.2 | Buzayan et al. | 1987 | Virology 160, 95-99 | M17439 | hammerhead | hairpin |
| Subterraneanclover mottle virus satellite RNA.1 | Davies et al. | 1990 | Virology 177, 216-224 | M33001 | hammerhead | |
| Subterraneanclover mottle virus satellite RNA.2 | Davies et al. | 1990 | Virology 177, 216-224 | M33000 | hammerhead | |
| *Solanum nodiflorum* mottle virus RNA | Haseloff and Symons | 1982 | Nucleic Acids Res. 10 3681-3691 | J02386 | hammerhead | |
| Velvet tobacco mottle virus circular viroid-like RNA-1 | Haseloff and Symons | 1982 | Nucleic Acids Res. 10 3681-3691 | | hammerhead | |
| Velvet tobacco mottle virus circular viroid-like RNA-2 | Haseloff and Symons | 1982 | Nucleic Acids Res. 10 3681-3691 | J02439 | hammerhead | |

TABLE 1-continued

| Different self-cleaving ribozymes | | | | | | |
|---|---|---|---|---|---|---|
| RNA Species | Reference | | | Accession Nr | (+) strand | (−) strand |
| Cherry small circular viroid-like RNA | Di Serio et al. | 1997 | J. Virol. 71 6603-6610 | Y12833 | mod. hammerhead | mod. |
| Carnation small viroid-like RNA-1 | Hernandez et al. | 1992 | Nucleic Acids Res. 20 6323-6329 | X68034 | hammerhead | hammerhead |
| Carnation small viroid-like RNA-2 | Hernandez et al. | 1992 | Nucleic Acids Res. 20 6323-6329 | | hammerhead | hammerhead |
| *Notophtalmus viridescens* (Newt) satellite 2 transcript | Epstein et al. | 1986 | J. Cell. Biol. 103 1137-1144 | X04478 | hammerhead | |
| *Neurospora* VS RNA | Saville and Collins | 1990 | Cell 61 685-696 | M32974 | VS RNA selfcleavage | |
| Schistosome satellite DNA | Ferbeyre et al. | 1998 | Mol. Cell. Biol. 18 3880-3888 | AF036739 | | |

The use of ribozymes in transgenic organisms to generate RNA molecules with 5' and or 3' termini of interest has been documented in the art. Rubio et al. 1999, describe broad-spectrum protection against Tombusviruses elicited by defective interfering (D1) RNAs in transgenic plants. To produce RNAs with authentic 5' and 3' termini identical to those of native D1 RNA, the D1 RNA sequence transcribed from a DNA cassette was flanked by ribozymes. Transgenic *Nicotiana benthamiana* plants were better protected than non-transgenic plants against infection by tomato bushy stunt virus and related tombusviruses. D1 RNAs interfere drastically with virus accumulation through effective competition with the parental virus for transacting factors required for replication. Egli and Braus, 1994 describe uncoupling of mRNA 3' cleavage and polyadenylation by expression of a hammerhead ribozyme in yeast. Eckner et al. 1991 described that test gene transcripts which could obtain a mature histone 3' end by the RNA cleaving activity of a cis-acting ribozyme, thus circumventing the cellular 3' end processing machinery were found to be transport deficient and accumulated in the nuclear compartment. However, these documents in the art are not related to methods for inhibiting phenotypic expression by homology dependent gene-silencing, particularly by PTGS.

A particularly preferred self-splicing ribozyme is the ribozyme comprised with the Barley yellow dwarf virus (BYDV) satellite RNA, quite particularly the satellite RNA found in BYDV isolates of the RPV serotype.

It has been found that reduction of the phenotypic expression of the nucleic acid of interest using a chimeric gene according to the invention was most efficient using a cDNA copy of the ribozyme comprised within the minus strand of BYDV satellite RNA. Therefore, ribozymes which show an autocatalytic activity similar to the autocatalytic activity of the ribozyme comprised within the minus strand of BYDV satellite RNA are especially suited for the methods of the invention. Autocatalytic activity of ribozymes can be compared with the autocatalytic activity of the (−) strand of BYDV satellite RNA as described by Miller et al. 1991.

The ribozyme motif within the (−) strand of BYDV satellite RNA has been identified as the nucleotide sequence of SEQ ID No 1 from the nucleotide at position 194 to the nucleotide at position 236. The ribozyme motif within the (+) strand of BYDV satellite RNA has been identified as the nucleotide sequence of SEQ ID No 2 from the nucleotide at position 310 to the nucleotide at position 322 followed by the nucleotide sequence of SEQ ID No. 2 from the nucleotide at position 1 to the nucleotide at position 89.

It goes without saying that more than one DNA region encoding a ribozyme may be comprised within the chimeric gene. These ribozymes may be clustered, e.g. they may all be located the region immediately proceeding DNA region encoding the '3 end formation and polyadenylation signal.

However, it is expected that more than one DNA region encoding a ribozyme may be comprised within the chimeric gene in such a way that upon self-cleavage more than one unpolyadenylated RNA molecules each comprising a target-specific nucleotide sequence is generated. Such a chimeric DNA could thus comprise:

a plant expressible promoter
a first target-specific DNA region
a DNA region encoding a first self-splicing ribozyme
a second target-specific DNA region
a DNA region encoding a second self-splicing ribozyme
a DNA region encoding a 3' end formation and polyadenylation signal.

The first and second self-splicing ribozyme may be identical, essentially similar or different. Likewise, the first and second target-specific DNA region encoding the RNA with a target-specific nucleotide sequence may be identical, essentially similar or different.

For practical reasons, it is thought that the number of DNA regions encoding a ribozyme within a single chimeric gene should not exceed five.

In a preferred embodiment, the nucleic acid of interest, whose phenotypic expression is targeted to be reduced, is a gene incorporated in the genome of a eukaryotic cell, particularly a plant cell. It will be appreciated that the means and methods of the invention can be used for the reduction of phenotypic expression of a gene which belongs to the genome of the cell as naturally occurring, (an endogenous gene), as well as for the reduction of phenotypic expression of a gene which does not belong to the genome of the cell as naturally occurring, but has been introduced in that cell (a transgene). The transgene can be introduced stably or transiently, and can be integrated into the nuclear genome of the cell, or be present on a replicating vector, such as a viral vector.

In another preferred embodiment, the nucleic acid of interest, whose phenotypic expression is targeted to be reduced is a viral nucleic acid, particularly a viral RNA molecule, capable of infecting a eukaryotic cell, particularly a plant cell. In this case, the phenotype to be reduced is the replication of the virus, and ultimately, the disease symptoms caused by the infecting virus.

For the purpose of the invention, the term "plant-expressible promoter" means a promoter which is capable of driving transcription in a plant cell. This includes any promoter of plant origin, but also any promoter of non-plant origin which is capable of directing transcription in a plant cell. A whole range of plant expressible promoters, is available to direct the transcription of the chimeric genes of the invention. These include, but, are not limited to strong promoters such as CaMV35S promoters (e.g., Harpster et al., 1988). In the light of the existence of variant forms of the CaMV35S promoter, as known by the skilled artisan, the object of the invention can equally be achieved by employing these alternative CaMV35S promoters and variants. It is also clear that other plant-expressible promoters, particularly constitutive promoters, such as the opine synthase promoters of the *Agrobacterium* Ti- or Ri-plasmids, particularly a nopaline synthase promoter, or subterranean clover virus promoters can be used to obtain similar effects. Also contemplated by the invention are chimeric genes to reduce the phenotypic expression of a nucleic acid in a cell, which are under the control of single subunit bacteriophage RNA polymerase specific promoters, such as a T7 or a T3 specific promoter, provided that the host cells also comprise the corresponding RNA polymerase in an active form.

It is a further object of the invention, to provide methods for reducing the phenotypic expression of a nucleic acid in specific cells, particularly specific plant cells by placing the chimeric genes of the invention under control of tissue-specific or organ-specific promoters. Such tissue-specific or organ-specific promoters are well known in the art and include but are not limited to seed-specific promoters (e.g., WO89/03887), organ-primordia specific promoters (An at al., 1996), stem-specific promoters (Keller at al., 1988), leaf specific promoters (Hudspeth at al., 1989), mesophyl-specific promoters (such as the light-inducible Rubisco promoters), root-specific promoters (Keller et al., 1989), tuber-specific promoters (Keil at al., 1989), vascular tissue specific promoters (Peleman et al., 1989), stamen-selective promoters (WO 89/10396, WO 92/13956), dehiscence zone specific promoters (WO 97/13865) and the like.

In another embodiment of the invention, the expression of a chimeric gene to reduce the phenotypic expression of a target nucleic acid can be controlled at will by the application of an appropriate chemical inducer, by operably linking the transcribed DNA region of the chimeric genes of the invention to a promoter whose expression is induced by a chemical compound, such as the promoter of the gene disclosed in European Patent publication ("EP") 0332104, or the promoter of the gene disclosed in WO 90/08826.

It will be clear to the person skilled in the art that the same effect in reducing the phenotypic expression of a nucleic acid in a plant cell may be achieved using a trans-splicing ribozyme to remove at least the polyadenylation site from the RNA transcript of a chimeric gene comprising a plant expressible promoter, a target-specific DNA region and a DNA region encoding a 3' end termination and polyadenylation signal to generate unpolyadenylated RNA comprising a target-specific nucleotide sequence.

As used herein "a trans-splicing ribozyme" is an RNA molecule capable of catalyzing the breakage or formation of a covalent bond within another RNA molecule at a specific site. The trans-splicing ribozyme should be chosen or designed in such a way that it recognizes a specific site preceding, preferably immediately preceding the polyadenylation signal of the RNA transcript comprising a target-specific nucleotide sequence. Methods to design such trans-splicing ribozyme with endoribonuclease activity are known in the art (see e.g. Haselhoff and Gerlach, 1988, WO 89/05852)

The DNA region encoding a trans-splicing ribozyme may be comprised within the chimeric gene encoding the target-specific RNA. Upon transcription of the chimeric gene an RNA molecule comprising the trans-splicing ribozyme and the target-specific nucleotide sequence may then generated, wherein the trans-splicing ribozyme is capable of cleaving a specific site preceding the polyadenylation site of another similar RNA molecule, to generate unpolyadenylated target-specific RNA molecules.

The trans-splicing ribozyme may also be provided by expression of another chimeric gene encoding an RNA molecule comprising the trans-splicing ribozyme in the same plant cell, according to methods and means available in the art (see e.g. Vaish et al. 1998; Bramlage et al. 1998).

Alternative methods may exist to provide unpolyadenylated target-specific RNA to the nucleus of a plant cell. Such methods include e.g. transcription of a chimeric gene, integrated in the nuclear genome of a plant cell comprising a target-specific DNA region, by an DNA-dependent RNA polymerase different from RNA polymerase II, such that RNA transcripts are generated independent from the normal processing mRNA machinery (including intron-splicing, capping and polyadenylation). This can be achieved e.g. by operably linking the target-specific DNA region to a promoter region, recognized by a single subunit RNA polymerase from a bacteriophage, such as but not limited to the T7 polymerase, and a DNA region comprising a terminator for such a polymerase. In this case, the plant cell needs to be provided with a chimeric gene encoding the corresponding RNA polymerase. Providing unpolyadenylated target-specific RNA to the nucleus of a plant cell can also be achieved e.g. by operably linking the target-specific DNA region to a promoter region, recognized by a eukaryotic RNA polymerase I or Ill, and a DNA region comprising a terminator for such a polymerase. The means and methods for constructing such chimeric genes and plant cells are described in detail in WO 97/49814 (incorporated by reference). Another alternative to provide unpolyadenylated target-specific RNA to the nucleus of a plant cell may include transcription of a chimeric gene comprising a target-specific DNA region operably linked to a plant-expressible promoter and linked to a DNA region comprising a 3' end formation signal but not a polyadenylation signal.

Although not intending to limit the invention to a specific mode of action, it is expected that the trigger of the homology-dependent gene-silencing mechanisms of the cell, particularly the co-suppression mechanism, is the accumulation of target-specific RNA into the nucleus of that cell. Providing unpolyadenylated RNA to the nucleus of the cell may be one mechanism of causing accumulation of target-specific RNA in a nucleus of a cell, but other aberrations such as the absence of a cap-structure or the presence of persistent introns etc. may constitute alternative ways to cause the accumulation of target-specific RNA in the nucleus of a cell.

Moreover, it is expected that other aberrations in the target-specific RNA molecules in addition to the absence of the polyA tail, including the absence of a cap-structure, or the presence of persistent introns or the presence of abnormal secondary structures, particularly the presence of giant hairpin structures, may have a cumulative effect on the inhibition of the normal transit of the RNA from the nucleus to the cytoplasm and hence have a cumulative or synergystic effect on the reduction of the phenotypic expression of a nucleic acid of interest.

The recombinant DNA comprising the chimeric gene to reduce the phenotypic expression of a nucleic acid of interest in a host cell, may be accompanied by a chimeric marker gene, particularly when the stable integration of the transgene in the genome of the host cell is envisioned. The chimeric marker gene can comprise a marker DNA that is operably linked at its 5' end to a promoter, functioning in the host cell of interest, particularly a plant-expressible promoter, preferably a constitutive promoter, such as the CaMV35S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable colour to the transformed plant cell, such as the A1 gene (Meyer et al., 1987), can provide herbicide resistance to the transformed plant cell, such as the bar gene, encoding resistance to phosphinothricin (EP 0,242,246), or can provide antibiotic resistance to the transformed cells, such as the aac(6') gene, encoding resistance to gentamycin (WO94/01560).

A recombinant DNA comprising a chimeric gene to reduce the phenotypic expression of a gene of interest, can be stably incorporated in the nuclear genome of a cell of a plant. Gene transfer can be carried out with a vector that is a disarmed Ti-plasmid, comprising a chimeric gene of the invention, and carried by Agrobacterium. This transformation can be carried out using the procedures described, for example, in EP 0 116 718.

Alternatively, any type of vector can be used to transform the plant cell, applying methods such as direct gene transfer (as described, for example, in EP 0 233 247), pollen-mediated transformation (as described, for example, in EP 0 270 356, WO85/01856 and U.S. Pat. No. 4,684,611), plant RNA virus-mediated transformation (as described, for example, in EP 0 067 553 and U.S. Pat. No. 4,407,956), liposome-mediated transformation (as described, for example, in U.S. Pat. No. 4,536,475), and the like.

Other methods, such as microprojectile bombardment as described for corn by Fromm at al. (1990) and Gordon-Kamm at al. (1990), are suitable as well.

Cells of monocotyledonous plants, such as the major cereals, can also be transformed using wounded and/or enzyme-degraded compact embryogenic tissue capable of forming compact embryogenic callus, or wounded and/or degraded immature embryos as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the chimeric gene for reduction of the phenotypic expression of a nucleic acid of interest of the invention in other varieties of the same or related plant species; or in hybrid plants. Seeds obtained from the transformed plants contain the chimeric genes of the invention as a stable genomic insert.

The means and methods of the invention can also be used for the reduction, of gene expression by co-suppression in eukaryotic cells and organisms.

In one embodiment the invention provides a method for reducing the phenotypic expression of a nucleic acid of interest, which is normally capable of being expressed in a eukaryotic cell, comprising the step of providing unpolyadenylated RNA comprising a target specific sense nucleotide sequence of at least 10 consecutive nucleotides with at least about 70% sequence identity to about 100% sequence identity to the nucleotide sequence of the nucleic acid of interest, to the nucleus of the eukaryotic cell.

In another embodiment, a method is provided for reducing the phenotypic expression of a nucleic acid of interest, which is normally capable of being expressed in a eukaryotic cell, comprising the step of introducing into the nuclear genome of the eukaryotic cell a chimeric DNA to generate a transgenic plant cell, DNA comprising the following operably linked parts:

(e) a promoter region functional in the eukaryotic cell;
(f) a target-specific DNA region comprising nucleotide sequence of at least 10 consecutive nucleotides with at least about 70% sequence identity to about 100% sequence identity to the nucleotide sequence of the nucleic acid of interest;
(g) a DNA region encoding a self-splicing ribozyme; and
(h) a DNA region involved in 3' end formation and polyadenylation wherein the chimeric DNA when transcribed produces a first RNA molecule comprising a target specific nucleotide sequence and a self-splicing ribozyme, which when cleaved by autocatalysis produces a second RNA molecule comprising a target specific nucleotide sequence wherein the 3' end of the first RNA molecule comprising the polyadenylation site has been removed.

Different preferred embodiments and definitions described in connection with the reduction of gene expression by homology dependent gene silencing in plant cells and plants also apply mutatis mutandis to the means and methods described for reduction of gene expression by co-suppression in eukaryotic cells and organisms. As used herein "eukaryotic cells" comprise plant cells, animal cells and human cells and cells from yeasts and fungi as well as cultures of such cells.

It is a further object of the invention to provide eukaryotic cells, preferably plant cells and organisms (preferably plants) comprising the chimeric genes for the reduction of the phenotypic expression of a target nucleic acid as described in the invention.

The methods and means of the invention can thus be used to reduce phenotypic expression of a nucleic acid in a eukaryotic cell or organism, particularly a plant cell or plant, for obtaining shatter resistance (WO 97/13865), for obtaining modified flower colour patterns (EP 522 880, U.S. Pat. No. 5,231,020), for obtaining nematode resistant plants (WO 92/21757, WO 93/10251, WO 94/17194), for delaying fruit ripening (WO 91/16440, WO 91/05865, WO 91/16426, WO 92/17596, WO 93/07275, WO 92/04456, U.S. Pat. No. 5,545,366), for obtaining male sterility (WO 94/29465, WO 89/10396, WO 92/18625), for reducing the presence of unwanted (secondary) metabolites in organisms, such as glucosinofates (WO 97/16559) or chlorophyll content (EP 779 364) in plants, for modifying the profile of metabolites synthesized in a eukaryotic cell or organisms by metabolic engineering e.g. by reducing the expression of particular genes involved in carbohydrate metabolism (WO 92/11375, WO 92/11376, U.S. Pat. No. 5,365,016, WO 95/07355) or lipid biosynthesis (WO 94/18337, U.S. Pat. No. 5,530,192) for delaying senescence (WO 95/07993), for altering lignification in plants (WO 93/05159, WO 93/05160), for altering the fibre quality in cotton (U.S. Pat. No. 5,597,718), for increasing bruising resistance in potatoes by reducing polyphenoloxidase (WO 94/03607), etc. The methods of the invention will lead to better results and/or higher efficiencies when compared to the methods using conventional sense or antisense nucleotide sequences and it is believed that other sequence-specific mechanisms regulating the phenotypic expression of target nucleic acids might be involved and/or triggered by the presence of the double-stranded RNA molecules described in this specification.

A particular application for reduction of the phenotypic expression of a transgene in a plant cell, inter alia, by antisense or sense methods, has been described for the restoration of male fertility, the latter being obtained by introduction of a transgene comprising a male sterility DNA (WO 94/09143, WO 91/02069). The nucleic acid of interest is specifically the male sterility DNA. Again, the processes and products described in this invention can be applied to these methods in order to arrive at a more efficient restoration of male fertility.

It will be appreciated that the methods and means described in the specification can also be applied in High Throughput Screening (HTS) methods, for the identification or confirmation of phenotypes associated with the expression of a nucleic acid sequence with hitherto unidentified function in a eukaryotic cell, particularly in a plant cell.

Such a method comprises the steps of:
1. selecting a target sequence within the nucleic acid sequence of interest with unidentified or non-confirmed function/phenotype when expressed. Preferably, if the nucleic acid has putative open reading frames, the target sequence should comprise at least part of one of these open reading frames. The length of the target nucleotide sequence may vary from about 10 nucleotides up to a length equaling the length (in nucleotides) of the nucleic acid of interest with unidentified function.
2. Introducing a chimeric DNA into the nucleus of a suitable host cell, comprising the nucleic acid of interest, wherein the chimeric DNA comprises a promoter region suitable for expression in the host cell, a DNA region encoding the target-specific nucleotide sequence, and a DNA region encoding a self-splicing ribozyme located immediately upstream of a DNA region involved in 3' end formation and polyadenylation.
3. observing the phenotype by a suitable method. Depending on the phenotype expected, it may be sufficient to observe or measure the phenotype in a single cell, but it may also be required to culture the cells to obtain an (organized) multicellular level, or even to regenerate a transgenic organism, particularly a transgenic plant.

It is also clear that the methods and means of the invention are suited for the reduction of the phenotypic expression of a nucleic acid in all plant cells of all plants, whether they are monocotyledonous or dicotyledonous plants, particularly crop plants such as but not limited to corn, rice, wheat, barley, sugarcane, cotton, oilseed rape, soybean, vegetables (including chicory, brassica vegetables, lettuce; tomato), tobacco, potato, sugarbeet but also plants used in horticulture, floriculture or forestry. The means and methods of the invention will be particularly suited for plants which have complex genomes, such as polyploid plants.

It is expected that the chimeric RNA molecules produced by transcription of the chimeric genes described herein, can spread systemically throughout a plant, and thus it is possible to reduce the phenotypic expression of a nucleic acid in cells of a non-transgenic scion of a plant grafted onto a transgenic stock comprising the chimeric genes of the invention (or vice versa) a method which may be important in horticulture, viticulture or in fruit production.

The following non-limiting Examples describe the construction of chimeric genes for the reduction of the phenotypic expression of a nucleic acid of interest in a eukaryotic cell and the use of such genes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:

SEQ ID No 1: cDNA copy of the (-) strand of BYDV RPV satellite, RNA
SEQ ID No 2: cDNA copy of the (+) strand of BYDV RPV satellite RNA
SEQ ID No 3: oligonucleotide for PCR amplification (SatPR1)
SEQ ID No 4: oligonucleotide for PCR amplification (SatPR2)
SEQ ID No 5: oligonucleotide for PCR amplification (SatPR3)
SEQ ID No 6: oligonucleotide for PCR amplification (SatPR4)

The following examples are presented in order to more fully illustrate the preferred embodiments of the invention and should not be construed, however, as limiting the broad scope of the invention.

EXAMPLES

Example 1

Experimental Procedures 1.1 Chimeric DNA Constructs
Ribozyme-Containing Gus Gene Constructs and a Control Construct The ribozyme sequences used are the plus strand or negative strand self-cleavage sequences of the satellite RNA of the barley yellow dwarf virus (BYDV)•RPV serotype, which was isolated in CSIRO Plant Industry (SEQ ID 1 and 2; Miller et al., 1991).

The two ribozyme-containing GUS constructs (pMBW259 and pMBW267) and one control GUS construct (pMBW265) are schematically drawn in FIG. 1. pMBW259 contains two plus strand cleavage sites, while pMBW267 contains the negative strand cleavage site.

To make these constructs, a β-glucuronidase (GUS) gene sequence was modified to contain a NcoI site around the translational start ATG and cloned into pART7 (Gleave, 1992) at the XhoI/EcoRI sites, forming pMBW258. The full-length BYDV-RPV satellite sequence was amplified by PCR using primers SatPR1 (SEQ ID No. 3) and SatPR4 (SEQ ID No. 6), digested with BamH1 and cloned into pMBW258 at the BamH1 site, and the resulting 35S-GUS-Sat-ocs cassette was excised and cloned into pART27 (Gleave, 1992), forming pMBW265. The same full-length satellite sequence was inserted into the BamH1 site of pMBW258 but in the antisense orientation, and the resulting 35S-GUS-asSat-ocs was cloned into pART27 to give rise to pMBW267.

To make pMBW259, the 3' and 5' halts of the satellite RNA sequences were amplified by PCR using primer pairs SatPR3 (SEQ ID No. 5) and SatPR4 (SEQ ID No. 6), and using SatPR1 (SEQ ID No. 3). and SatPR2 (SEQ ID No 4), respectively. Fusion of the full-length sequence with the 3' half and the 5' half sequences were made through ligation between the EcoRV and HpaI ends of the three PCR fragments. This fusion mimics the natural multimeric forms of the satellite RNA, and therefore maintains the plus strand cleavae property of the native forms. The fusion sequence was cloned into pGEM-3Z (Promega) at the SacI/PstI sites, excised with HindIII/EcoRI, blunted, and inserted into pART7 at the SmaI site, into which the GUS sequence described above was then cloned at the XhoI/EcoRI sites. The resulting 3SS-GUS-Sat-ocs was inserted into pART27 at the NotI site, forming pMBW259.

The Super-Transforming Gus Construct

The BamHI fragment was excised from pIG121 Hm (Hiei et al., 1994) and cloned into pART7. The GUS-nos sequence was then excised by AccI, blunted, and inserted into pBluescript at the HincII site. The 1.3 kb region of a cucurbit phloem protein PP2 gene was excised with NotI/HindIII from a lambda clone CPPI.3 and cloned into the above Bluescript plasmid. The resulting PP2-GUS-nos was excised with NotI/KpnI and inserted into pWBVec2 (Wang at al., 1998), giving rise to pBPPGH (FIG.

1.2 Tobacco Transformation

Nicotiana tobaccum cv. W38 was transformed and regenerated into whole plants essentially as described by Ellis et al. 1987. For constructs pMBW259, pMBW265 and pMBW267, 50 mg/L kanamycin was included in the media for selection of transformed tissue. For construct pBPPGH, 25 mg/L hygromycin B was used.

1.3 GUS Assay

GUS gene expression was assayed histochemically or fluorometrically according to Jefferson et al. 1987.

Example 2

GUS Expression in Transgenic Tobacco Transformed with a Single Type of the Gus Constructs Transgenic plants containing pMBW259 and pMBW267 showed very low levels of GUS expression, as judged by lack of, or faint blue, GUS staining. Plants transformed with pMBW265 showed more GUS expression than with pMBW259 and pMBW267, but the level was much lower than plants transformed with pBPPGH. The best pMBW265 lines expressed 13.3% of the GUS activity by an average pBPPGH line.

Example 3

GUS Expression in Super-Transformed Lines Containing pBPPGH and One of the Three Other Constructs of Example 1

In order to promote silencing of a normal GUS gene by the presence of the ribozyme sequence near the 3' end of the GUS gene transcript, plants containing pMBW259, pMBW265 or pMBW267 and pBPPGH were constructed by re-transformation. Histochemical GUS assays of the super-transformants showed that the pMBW267 background gave substantially higher proportions of transformants than the pMBW259 or the pMBW265 background that showed low levels of GUS expression as indicated by the lack of strong and uniform blue staining. Super-transformants containing pBPPGH and pMBW265 showed the best GUS expression.

Table 2 shows the result of fluorometric GUS (MUG) assay of the supertransformants. The lines (E and F) containing pBPPGH and pMBW267 showed uniformly low GUS expression compared with the other lines. The best GUS expression came from the C lines which contain pBPPGH and pMBW265.

Among the three constructs tested, pMBW265 does not contain the full-length functional ribozyme sequences of the BYDV satellite RNA in a continuous stretch, and is therefore expected to produce mainly poly(A)+RNA. pMBW259 contains two copies of the plus strand ribozyme sequence, and should give rise to RNA that have poly(A) tails removed by ribozyme cleavage. pMBW267 contain the negative strand ribozyme. The negative strand ribozyme was previously shown to be much (at least 10-fold) more efficient than the plus strand ribozyme (Miller et al., 1991), and therefore it is expected that pMBW267 produces poly(A)-RNA more efficiently. Our experiment showed that the super-transformed lines having the pMBW267 background expressed uniformly low levels of GUS activity in comparison with the lines having the pMBW259 or the pMBW265 background. The highest GUS expressing lines were from the pMBW265 background, which does not produce polyA-RNA.

TABLE 2

MUG assay of super-transformed tobacco lines*.

| Super-transformed lines | MUG Readings |
|---|---|
| A1 | 10.1 |
| A2 | 15.8 |
| A3 | 30.6 |
| A4 | 47.3 |
| A5 | 0.29 |
| A6 | 10.3 |
| A7 | 5.8 |
| A8 | 13.15 |
| A9 | 7.34 |
| A10 | 9.76 |
| A11 | 17.74 |
| A12 | 34.8 |
| A13 | 4.33 |
| A14 | 3.41 |
| A15 | 11.2 |
| A16 | 2.04 |
| A17 | 13.29 |
| A18 | 14.6 |
| A19 | 0.14 |
| A20 | 17.2 |
| A21 | 9.22 |
| A22 | 17.3 |
| B1 | 9.57 |
| B2 | 44.7 |
| B3 | 17.7 |
| B4 | 1.25 |
| B5 | 13.5 |
| B6 | 11.4 |
| B7 | 6.28 |
| B8 | 24.8 |
| B9 | 16.3 |
| B10 | 9.72 |
| B11 | 3.71 |
| B12 | 0.08 |
| B13 | 20.6 |
| B14 | 11.9 |
| B15 | 3.11 |
| B16 | 8.25 |
| B17 | 4.12 |
| B18 | 6.04 |
| C1 | 8.84 |
| C2 | 16.9 |
| C3 | 17.9 |
| C4 | 22.8 |
| C5 | 11.7 |
| C6 | 14.5 |
| C7 | 44.0 |
| C8 | 19.0 |
| C9 | 29.8 |
| C10 | 32.1 |
| C11 | 37.1 |
| C12 | 2.51 |
| C13 | 14.5 |
| C14 | 25.8 |
| C15 | 7.20 |
| C16 | 30.2 |
| C17 | 9.70 |
| C18 | 13.4 |

TABLE 2-continued

MUG assay of super-transformed tobacco lines*.

| Super-transformed lines | MUG Readings |
|---|---|
| C19 | 19.3 |
| C20 | 17.0 |
| D1 | 6.01 |
| D2 | 12.9 |
| D3 | 0.19 |
| D4 | 7.88 |
| D5 | 1.24 |
| D6 | 0.44 |
| D7 | 14.1 |
| D8 | 0.91 |
| D9 | 5.49 |
| D10 | 1.30 |
| D11 | 15.1 |
| D12 | 6.63 |
| D13 | 12.2 |
| D14 | 15.8 |
| D15 | 1.32 |
| D16 | 2.29 |
| D17 | 3.59 |
| D18 | 22.1 |
| D19 | 13.0 |
| D20 | 4.37 |
| E1 | 4.32 |
| E2 | 3.15 |
| E3 | 3.56 |
| E4 | 3.31 |
| E5 | 3.68 |
| E6 | 5.02 |
| E7 | 2.63 |
| E8 | 10.27 |
| E9 | 10.81 |
| E10 | 13.1 |
| E11 | 5.10 |
| E12 | 2.86 |
| E13 | 4.00 |
| E14 | 16.8 |
| E15 | 4.02 |
| E16 | 1.29 |
| E17 | 1.78 |
| E18 | 3.57 |
| E19 | 0.43 |
| E20 | 11.8 |
| F1 | 5.73 |
| F2 | 5.10 |
| F3 | 4.16 |
| F4 | 4.69 |
| F5 | 0 |
| F6 | 1.93 |
| F7 | 3.21 |
| F8 | 2.77 |
| F9 | 1.86 |
| F10 | 3.27 |
| F11 | 2.85 |
| F12 | 3.25 |
| F13 | 2.17 |
| F14 | 2.84 |
| F15 | 3.11 |
| F16 | 2.06 |
| F17 | 2.90 |
| F18 | 3.75 |
| F19 | 4.16 |
| F20 | 2.49 |

*A and B, from super-transformation of two independent pMBW259 lines with pBPPGH; C and D, from super-transformation of two independent pMBW265 lines with pBPPGH; E and F, from super-transformation of two independent pMBW267 lines with pBPPGH.

Example 4

Experimental Procedures

Gene Construction

Figure 2A:
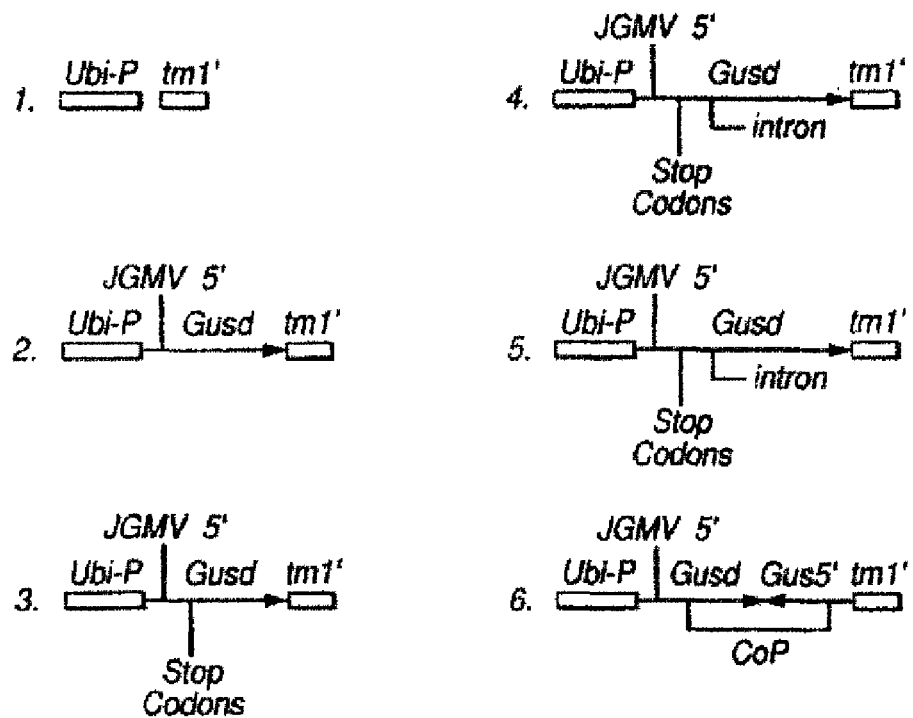
FIG. 2 represents schematically the different sense and antisense constructs, as well as the so-called CoP (complementary pair) constructs used for obtaining virus resistance (FIG. 2B) or for reducing the phenotypic expression of a transgenic Gus gene (FIG. 2A).
Figure 2B:
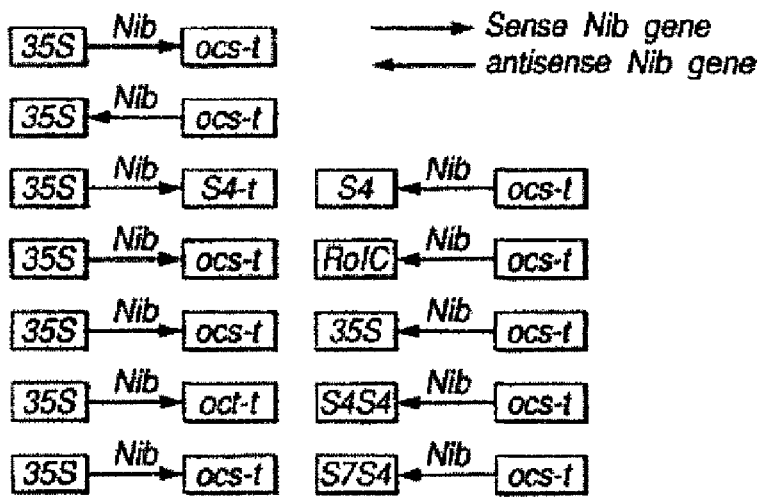

Standard gene cloning methods (Sambrook et al. 1989) were used to make the chimeric genes. A schematic representation of the constructs used is shown in FIGS. 2A and 2B.

The components for these constructs were:

Cauliflower mosaic virus 35S promoter from the Cabb-JI isolate (35S) (Harpster et al., 1988)

Octopine synthase terminator (ocs-t) (MacDonald et al., 1991)

Subterranean clover virus promoter No 4 (S4) (WO 9606932)

Subterranean clover virus terminator No 4 (sot) (WO 9606932)

Subterranean clover virus double enhancer promoter No 4 (S4S4)

Subterranean clover virus promoter No 4 with S7 enhancer (S7S4)

Maize ubiquitin promoter (Ubi) (Christensen and Quail, 1996)

Agrobacterium tumour morphology 1 gene terminator (tml') (Zheng et al., 1991)

the Nia gene of an Australian strain of Potato virus Y (Nia)

a dysfunctional β-glucuronidase open reading frame encoding DNA (Gusd)

a modified 5' untranslated region (5'UTR) from Johnson-grass mosaic virus (JGMV5')

This contains insertion of a NcoI site at the ATG start codon followed by three stop codons in frame, and a PstI site (for insertion of the intron as in constructs 4 and 5 of FIG. 2A). In vector constructs 2 and 6 of FIG. 2A, the Gusd open reading frame is inserted in at the NcoI site, removing the stop codons; in all other constructs of FIG. 2A it is inserted downstream of the PstI site.

a castor bean catalase intron (Ohta at al., 1990) as modified by Wang et al. (1997) ("intron").

The chimeric genes were constructed by operably assembling the different parts as schematically indicated in FIG. 2A or FIG. 2B and inserting the obtained chimeric genes in the T-DNA vectors pART27 and pART7 vectors (Gleave, 1992) between the left T-DNA border and the chimeric plant expressible neo gene.

The DNA encoding a dysfunctional β-glucuronidase open reading frame (GUSd) was obtained by deleting from a gus coding region the sequence between the two EcoRV restriction sites. For the construction of the chimeric gene encoding the RNA molecule comprising both sense and antisense nucleotide sequence to a) β-glucuronidase gene, a sequence was added to the Gusd gene to be allow base pairing the 5'end over 558 bases. This sequence was cloned between the maize ubiquitin promoter and the tml' terminator and inserted in a T-DNA vector.

T-DNA vectors were constructed which comprised a first and a second chimeric virus resistance gene, wherein the first chimeric gene consisted of:

1. a CaMV 35S promoter sequence, coupled to
2. in sense orientation, the nucleotide sequence from PVY encoding either
    Vpg protein (see e.g., Genbank Accession Nr ZZ9526 from nucleotide 1013 to nucleotide 1583), or
    part of the CI protein (see e.g., Genbank Accession Nr M95491 from nucleotide 3688 to nucleotide 4215) or
    Protease (Pro) (see e.g., EMBL Accession Nr D00441 from nucleotide 5714 to nucleotide 7009), followed by
3. the S4 terminator from subterranean clover mosaic virus, as described above.

The second chimeric gene consists of
1. a S4 promoter as described above, coupled to
2. in anti-sense orientation, the nucleotide sequence from PVY encoding either
   Vpg protein, or
   CI protein or
   Protease, followed by
3. the octopine synthase terminator as described above.

The sense and antisense sequences within one T-DNA vector were derived from the same PVY coding region.

Figure 3A:
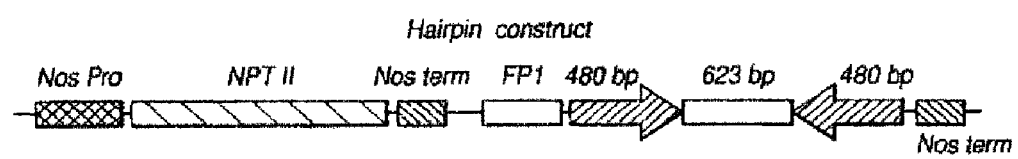
FIG. 3A represents schematically the so-called panhandle construct or CoP constructs used for reducing the phenotypic expression of a Δ12 desaturase gene in *Arabidopsis* (Nos Pro: nopaline synthase gene promoter; nptII neomycin phosphotransferase coding region; Nos term: nopaline syntase gene terminator; FP1: truncated seed specific napin promoter; 480 bp: 5' end of the Fad2 gene of *Arabidopsis thaliana* in sense orientation; 623 bp: spacer; 480 bp: 5' end of the Fad2 gene of *Arabidopsis thaliana* in antisense orientation.

Also, T-DNA vectors were constructed for use in altering the fatty acid composition in oil (see FIG. 3), comprising
1. a FPI promoter (truncated seed specific napin promoter, containing sequences between −309 and +1, as described in Stalberg et al; linked to
2. a nucleotide sequence comprising the 480 bp located 5' in the ORF encoding the Δ12 desaturase from *Arabidopsis thaliana* (Fad2) in sense orientation and in antisense orientation, linked by a 623 bp spacer sequence; followed by
3. the terminator from the nopaline synthase gene.

In addition, T-DNA vectors were constructed to evaluate the influence of a presence of an intron sequence in the chimeric genes encoding complemenatary pair ("CoP") constructs. To this end, constructs were made comprising:
1. a CamV35S promoter, followed by
2. the protease encoding ORE from PVY (see above) in sense orientation;
3. the sequence of the *Flaveria trinervia* pyruvate orthophospate dikinase intron 2)
4. the protease encoding ORF from PVY in antisense orientation; and
5. the octopine synthase gene terminator.

Plant Transformation

Nicotiana tabacum (W38) tissue was transformed and regenerated into whole plants essentially as described by Landsman et al. (1988). Rice (*Oryza sativa*) was transformed essentially as described by Wang et al. (1997).

Rice Supertransformation

Mature embryos from a rice plant expressing GUS and hygromycin phosphotransferase (HPT) activity were excised from mature seed and placed on callus inducing media for 7 weeks. Calli were recovered from these cultures, incubated with Agrobacteria containing various binary vector constructs for 2 days, then placed on callusing media containing hygromycin, bialaphos and Timentin™. During the next four weeks hygromycin and bialaphos resistant calli developed. These callus lines were maintained on hygromycin and bialaphos containing media for a further 2 months before being assayed for GUS activity.

GUS Assay

Rice calli were tested for GUS activity using the histochemical stain X-glucuronide or the fluorogenic substrate 4-methyl-umbeliferone glucuronide (MUG) essentially as described by Jefferson et al. (1987).

Comparison of Chimeric Genes Comprising Only Antisense, Only Sense, or Both Sense and Antisense (Complimentary Pair (CoP)) Sequence for Reduction in Phenotypic Expression of an Integrated β-Glucuronidase Gene.

Transgenic rice tissue expressing β-glucuronidase (GUS) from a single transgene (and hygromycin resistance from a hph gene) (lines V10-28 and V10-67) was supertransformed using vectors that contained the bar gene conferring phosphinothricin resistance and various sense, antisense and CoP constructs (see FIG. 2A) derived from a crippled GUS (GUSd) gene. The supertransformed tissue was maintained on hygromycin and bialaphos selection media for 3 weeks then analyzed for GUS activity. A crippled GUS gene was used so that expression from this gene would not be superimposed on the endogenous GUS activity.

The figures in Table 2 represent the rate of MU production measured by absorption at 455 nm, with excitation at 365 nm of 1.5 μg of total protein in a reaction volume of 200 μl. The rate was measured over 30 min at 37° C. The reading for non-transgenic rice calli was 0.162. The figures in bracket which follow the description of the introduced construct refer to FIG. 2A.

The results (Table 2) showed that supertransformation with the binary vector containing the bar gene without the GUSd gene had no silencing effect on the endogenous GUS activity. Supertransformation with GUSd in a sense or antisense orientation, with or without an intron or an early stop codon, showed some degree of reduction (in about 25% of the analyzed calli) of the endogenous GUS activity (see last two rows in Table 2 representing the percentage of analyzed calli with a MUG assay reading of less than 2.000). However, supertransformation with a CoP construct gave in about 75% to 100% of the analyzed calli, reduction of the endogenous GUS activity. This CoP construct was designed so that the 3' end of the mRNA produced could form a duplex with the 5' end of the transcript to give a "panhandle" structure.

These data show that a complimentary pair can be made using one self-annealing transcript, that this design is much more effective than a conventional sense or antisense construct, and that the approach can be used to reduce the phenotypic expression of genes present in a plant cell.

TABLE 2

MUG assay of Supertransformed Rice Calli

|  | Vector cassette (1) | Sense (2) | Sense + Stop (3) | Sense + stop + intron (4) | Antisense + stop + intron (5) | Inverted repeat CoP (6) |
|---|---|---|---|---|---|---|
| V10-28 | 121.0 | 97.45 | 38.43 | 38.88 | 0.290 | 0.565 |
|  | 45.58 | 6.637 | 64.16 | 115.5 | 0.572 | 0.316 |
|  | 99.28 | 71.60 | 149.2 | 133.0 | 37.2 | 0.351 |
|  | 26.17 | 0.224 | 0.955 | 98.46 | 53.94 | 0.210 |
|  | 92.21 | 0.321 | 68.32 | 0.502 | 105.5 | 0.701 |
|  | 108.8 | 5.290 | 105.6 | 39.35 | 56.73 | 0.733 |
|  | 6.432 | 0.9460 | 136.6 | 1.545 | 60.36 | 2.103 |
|  | 90.80 | 32.44 | 140.4 | 10.36 | 71.12 | 119.8 |
|  | 98.24 | 128.8 | 62.38 | 111.6 | 13.17 | 0.717 |

TABLE 2-continued

MUG assay of Supertransformed Rice Calli

| Vector cassette (1) | Sense (2) | Sense + Stop (3) | Sense + stop + intron (4) | Antisense + stop + intron (5) | Inverted repeat CoP (6) |
|---|---|---|---|---|---|
|  | 93.76 | 31.28 | 17.79 | 14.42 | 0.424 | 0.398 |
|  |  | 5.023 |  | 88.06 | 26.98 | 0.315 |
|  |  | 40.27 |  | 52.28 | 115.5 | 0.270 |
|  |  | 36.40 |  | 30.26 | 149.7 | 16.78 |
|  |  | 53.24 |  | 107.5 | 66.75 | 67.28 |
|  |  | 29.97 |  | 26.75 | 145.8 | 0.217 |
|  |  | 89.06 |  | 105.1 | 0.534 | 0.208 |
|  |  | 0.256 |  | 135.1 | 9.4 |  |
|  |  | 68.23 |  | 95.04 | 35.33 |  |
|  |  | 5.481 |  | 71.5 |  |  |
| V10-67 | 318.8 | 93.43 | 0.199 | 31.82 | 1.395 | 0.472 |
|  | 109.5 | 73.19 | 0.197 | 58.08 | 152.4 | 0.256 |
|  | 30.35 | 128.1 | 0.157 | 56.32 | 67.42 | 0.296 |
|  | 40.04 | 1.506 | 128 | 44.62 | 12.11 | 0.452 |
|  | 228 | 140.6 | 130.3 | 0.454 | 0.668 | 0.422 |
|  | 23.05 | 1.275 | 196.2 | 17.32 | 23.34 | 0.196 |
|  | 241.2 | 0.272 | 12.43 | 73.2 | 76.10 | 0.294 |
|  | 118.5 | 0.209 | 140.0 | 20.32 | 130.1 | 0.172 |
|  | 11.27 | 42.05 | 90.13 | 107.4 | 0.841 | 0.436 |
|  | 110.6 | 117.5 | 157.4 | 0.453 | 66.12 | 0.398 |
|  | 19.29 | 118.9 | 0.518 | 87.81 | 136.9 | 0.242 |
|  | 121.0 | 21.44 | 0.231 | 0.299 | 67.92 |  |
|  | 115.1 | 155.0 | 116.1 | 0.206 | 50.32 |  |
|  | 77.1 | 190.9 | 43.18 | 12.47 | 170.3 |  |
|  | 106.1 | 0.773 | 31.06 | 0.213 | 108.9 |  |
|  | 73.12 | 0.146 |  | 11.15 | 1.241 |  |
|  | 29.97 |  |  | 19.22 | 4.092 |  |
|  | 50.11 |  |  |  | 169.6 |  |
|  | 80.34 |  |  |  | 76.88 |  |
|  | 117.8 |  |  |  | 22.08 |  |
|  | 159.1 |  |  |  | 91.6 |  |
|  | 67.52 |  |  |  | 7.855 |  |
|  | 92.32 |  |  |  | 69.76 |  |
|  | 27.97 |  |  |  | 0.822 |  |
| V10-28 | 0% | 21% | 10% | 10.5% | 22% | 75% |
| V10-67 | 0% | 37.5% | 33% | 29.5% | 21% | 100% |

Example 5

Intron Enhanced Silencing

The T-DNA vectors comprising the chimeric genes encoding the CoP constructs wherein an intron (*Flaveria trinervia* pyruvate orthophosphate dikinase intron 2) has been inserted in either the sense orientation or the antisense orientation, between the sense and antisense sequences corresponding to the protease encoding ORE from PVY (as described above and in PCT-application PCT/IB99/00606) were used to obtain transformed tobacco plants, which were subsequently challenged with PVY. The results are summarized in the following table:

TABLE 3

| Construct | Number of immune plants/Number of independent transgenic plants |
|---|---|
| 35S-Pro(sense)-intron(sense)-Pro(antisense)-Ocs-t | 22/24 |
| 35S-Pro(sense)-intron(antisense)-Pro(antisense)Ocs-t | 21/24 |

Example 6

Modifying Oil Profile Using CoP Constructs in *Arabidopsis*

T-DNA vectors for modifying the fatty acid composition in oil, extracted from crushed seeds as described above and in PCT-application PCT/IB99/00606 were used to introduce the chimeric gene encoding the CoP construct for reducing the expression (see FIG. 3A) the Δ12 desaturase gene (Fad2) in *Arabidopsis thaliana*.

Figure 3B:
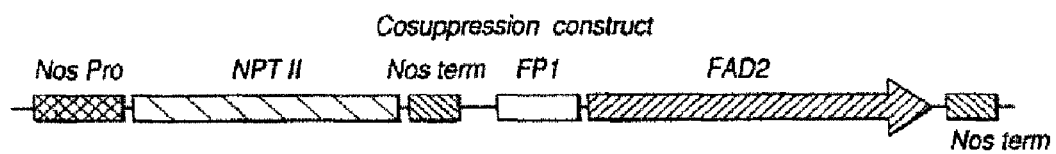
FIG. 3B represents schematically a common cosuppression construct for reducing the phenotypic expression of a Δ12 desaturase gene in Arabidopsis thaliana.

For comparison of the efficiency, transgenic *Arabidopsis* plants were generated wherein the Fad2 gene expression was reduced by a plain cosuppression construct, comprising the FP1 seed-specific promoter coupled to the complete ORF from the Δ12 desaturase gene (Fad2) in Arabidopsis thaliana and the nopaline synthase promoter (see FIG. 3B).

As control plants, transgenic Arabidopsis transformed by unrelated T-DNA constructs were used.

Seeds were harvested, crushed and extracted and the percentage of the major fatty acids in the oil was determined by methods available in the art. The results, which are the mean of two readings, are summarized in Table 4.

TABLE 4

| Sample Name | Myristic | Palmitic | Palmitoleic | Stearic | Oleic | Linoleic | Linolenic | 20:0 | 20:1 | 22:0 | 22:1 | 24:0 | C18:1/ (C18:2 + C18:3) |
|---|---|---|---|---|---|---|---|---|---|---|---|---|---|
| Hairpin 1.1 | 0.00 | 6.06 | 0.52 | 3.21 | 56.65 | 7.50 | 6.82 | 1.46 | 16.02 | 0.00 | 1.76 | 0.00 | 3.95 |
| Hairpin 1.2 | 0.12 | 6.86 | 0.39 | 3.40 | 51.28 | 10.00 | 8.73 | 1.64 | 15.60 | 0.00 | 1.97 | 0.00 | 2.74 |
| Hairpin 1.3 | 0.11 | 8.47 | 0.50 | 3.49 | 21.64 | 28.99 | 18.51 | 2.02 | 14.19 | 0.00 | 2.09 | 0.00 | 0.46 |
| Hairpin 1.4 | 0.00 | 6.14 | 0.50 | 3.37 | 51.70 | 9.77 | 8.02 | 1.73 | 16.04 | 0.00 | 2.05 | 0.67 | 2.91 |
| Hairpin 2.1 | 0.06 | 5.19 | 0.43 | 3.33 | 54.84 | 5.52 | 7.76 | 1.77 | 18.50 | 0.34 | 1.83 | 0.45 | 4.13 |
| Hairpin 2.2 | 0.04 | 7.67 | 0.46 | 3.75 | 19.60 | 28.29 | 18.64 | 2.55 | 15.96 | 0.19 | 2.28 | 0.56 | 0.42 |
| Hairpin 3.1 | 0.00 | 7.99 | 0.53 | 3.62 | 19.52 | 28.41 | 19.24 | 2.32 | 15.14 | 0.00 | 2.23 | 0.99 | 0.41 |
| Hairpin 3.2 | 0.09 | 7.00 | 0.54 | 3.69 | 49.02 | 11.03 | 9.64 | 1.71 | 14.94 | 0.00 | 1.72 | 0.62 | 2.37 |
| Hairpin 3.3 | 0.00 | 5.68 | 0.49 | 3.98 | 46.19 | 12.82 | 9.71 | 2.10 | 16.70 | 0.00 | 1.94 | 0.39 | 2.05 |
| Hairpin 3.4 | 0.17 | 7.19 | 0.77 | 3.69 | 45.90 | 11.86 | 10.65 | 1.84 | 15.39 | 0.00 | 1.90 | 0.65 | 2.04 |
| Hairpin 3.5 | 0.00 | 6.45 | 0.48 | 3.26 | 51.76 | 8.13 | 10.04 | 1.51 | 16.08 | 0.00 | 1.92 | 0.36 | 2.85 |
| Hairpin 3.6 | 0.08 | 7.51 | 0.23 | 3.59 | 19.97 | 29.13 | 20.12 | 2.15 | 14.54 | 0.29 | 2.02 | 0.36 | 0.41 |
| Hairpin 3.7 | 0.14 | 7.20 | 0.78 | 2.90 | 26.37 | 24.81 | 17.18 | 1.92 | 15.50 | 0.36 | 2.30 | 0.53 | 0.63 |
| Hairpin 3.8 | 0.11 | 6.34 | 0.46 | 3.23 | 38.58 | 15.25 | 13.54 | 1.89 | 16.91 | 0.00 | 2.36 | 1.34 | 1.34 |
| Hairpin 3.9 | 0.00 | 6.47 | 0.49 | 3.32 | 47.59 | 11.44 | 9.63 | 1.68 | 15.96 | 0.00 | 1.88 | 1.55 | 2.26 |
| Hairpin 3.10 | 0.00 | 6.77 | 0.56 | 3.48 | 53.30 | 7.57 | 9.34 | 1.55 | 15.65 | 0.00 | 1.79 | 0.00 | 3.15 |
| Hairpin 3.11 | 0.00 | 7.05 | 0.59 | 3.61 | 53.62 | 8.87 | 8.36 | 1.55 | 14.35 | 0.00 | 1.99 | 0.00 | 3.11 |
| Hairpin 3.12 | 0.05 | 8.32 | 0.36 | 3.85 | 18.48 | 29.24 | 19.94 | 2.48 | 14.75 | 0.00 | 2.28 | 0.26 | 0.38 |
| Hairpin 4.1 | 0.09 | 6.97 | 0.59 | 3.61 | 53.64 | 8.40 | 8.44 | 1.60 | 15.00 | 0.00 | 1.66 | 0.00 | 3.19 |
| Hairpin 4.2 | 0.07 | 6.81 | 0.22 | 3.27 | 55.06 | 9.16 | 8.71 | 1.26 | 13.63 | 0.19 | 1.33 | 0.30 | 3.08 |
| Hairpin 4.3 | 0.04 | 6.81 | 0.50 | 3.47 | 46.21 | 10.67 | 11.52 | 1.81 | 16.50 | 0.00 | 1.88 | 0.58 | 2.08 |
| Hairpin 5.1 | 0.00 | 8.30 | 0.23 | 3.71 | 17.72 | 28.92 | 20.63 | 2.38 | 14.77 | 0.00 | 2.41 | 0.92 | 0.36 |
| Hairpin 5.2 | 0.19 | 7.15 | 1.55 | 3.56 | 44.58 | 11.44 | 11.59 | 1.77 | 15.67 | 0.00 | 1.84 | 0.65 | 1.94 |
| Hairpin 5.3 | 0.10 | 6.49 | 0.40 | 3.72 | 54.19 | 7.01 | 7.89 | 1.74 | 15.91 | 0.00 | 1.92 | 0.62 | 3.64 |
| Hairpin 5.5 | 0.12 | 6.58 | 0.51 | 3.84 | 54.48 | 6.16 | 7.23 | 1.77 | 16.50 | 0.42 | 1.90 | 0.48 | 4.07 |
| Hairpin 5.6 | 0.00 | 6.67 | 0.50 | 3.66 | 46.32 | 11.56 | 10.48 | 1.83 | 15.99 | 0.06 | 2.15 | 0.84 | 2.10 |
| Hairpin 5.7 | 0.00 | 5.50 | 0.51 | 3.58 | 57.33 | 4.75 | 5.91 | 1.75 | 18.03 | 0.00 | 1.88 | 0.76 | 5.38 |
| Hairpin 5.8 | 0.16 | 6.55 | 1.53 | 3.54 | 48.52 | 9.91 | 8.97 | 1.78 | 16.39 | 0.00 | 1.84 | 0.81 | 2.57 |
| Hairpin 6.1 | 0.10 | 6.35 | 0.57 | 3.48 | 59.00 | 4.77 | 6.26 | 1.48 | 15.95 | 0.00 | 1.80 | 0.25 | 5.35 |
| Hairpin 6.2 | 0.10 | 7.98 | 0.37 | 4.06 | 20.96 | 29.01 | 18.69 | 2.38 | 13.63 | 0.20 | 2.03 | 0.60 | 0.44 |
| Hairpin 6.5 | 0.08 | 6.21 | 0.63 | 3.61 | 60.05 | 5.07 | 5.27 | 1.55 | 15.20 | 0.00 | 1.69 | 0.66 | 5.81 |
| Columbia pBin 19 control | 0.08 | 8.81 | 0.47 | 3.51 | 17.07 | 30.31 | 20.94 | 1.78 | 14.56 | 0.00 | 2.17 | 0.28 | 0.33 |
| Cosuppresion 1.1 | 0.08 | 8.16 | 0.62 | 3.71 | 26.16 | 23.77 | 18.15 | 2.06 | 14.65 | 0.17 | 1.89 | 0.57 | 0.62 |
| Cosuppresion 1.2 | 0.00 | 8.49 | 0.53 | 3.65 | 17.90 | 29.93 | 20.36 | 2.34 | 14.25 | 0.00 | 2.33 | 0.23 | 0.36 |
| Cosuppresion 1.3 | 0.07 | 6.65 | 0.40 | 3.42 | 38.34 | 15.25 | 14.16 | 1.91 | 17.19 | 0.31 | 1.94 | 0.35 | 1.30 |
| Cosuppresion 1.4 | 0.00 | 8.22 | 0.57 | 3.82 | 18.27 | 28.82 | 19.63 | 2.56 | 14.83 | 0.00 | 2.46 | 0.83 | 0.38 |
| Cosuppresion 1.5 | 0.00 | 7.51 | 0.52 | 3.84 | 34.59 | 17.90 | 14.64 | 2.18 | 16.27 | 0.00 | 2.02 | 0.54 | 1.06 |
| Cosuppresion 1.6 | 0.07 | 7.44 | 0.47 | 3.16 | 23.97 | 27.32 | 17.29 | 2.03 | 15.52 | 0.18 | 2.22 | 0.33 | 0.54 |
| Cosuppresion 2.1 | 0.07 | 7.46 | 0.43 | 3.00 | 23.91 | 27.21 | 17.79 | 1.84 | 15.27 | 0.30 | 2.14 | 0.58 | 0.53 |
| Cosuppresion 2.2 | 0.00 | 8.19 | 0.55 | 4.22 | 18.59 | 28.31 | 18.80 | 2.77 | 15.51 | 0.00 | 2.46 | 0.58 | 0.39 |
| Cosuppresion 2.3 | 0.00 | 8.71 | 0.47 | 3.48 | 19.21 | 30.06 | 19.49 | 2.03 | 13.78 | 0.00 | 2.15 | 0.63 | 0.39 |
| Cosuppresion 3.1 | 0.06 | 7.57 | 0.50 | 3.83 | 32.24 | 20.00 | 15.66 | 2.06 | 15.65 | 0.34 | 1.85 | 0.23 | 0.90 |
| Cosuppresion 4.1 | 0.00 | 7.29 | 0.43 | 3.55 | 30.26 | 21.17 | 17.06 | 2.01 | 16.08 | 0.00 | 1.92 | 0.25 | 0.79 |
| Cosuppresion 4.2 | 0.08 | 8.02 | 0.53 | 3.62 | 33.04 | 20.04 | 15.68 | 1.80 | 14.72 | 0.00 | 1.88 | 0.58 | 0.92 |
| Cosuppresion 4.3 | 0.07 | 8.35 | 0.54 | 3.85 | 30.02 | 21.72 | 16.78 | 2.01 | 14.25 | 0.00 | 1.92 | 0.49 | 0.78 |
| Cosuppresion 4.4 | 0.06 | 6.98 | 0.53 | 3.62 | 43.38 | 13.24 | 12.77 | 1.74 | 15.37 | 0.30 | 1.67 | 0.33 | 1.67 |
| Cosuppresion 4.5 | 0.13 | 7.84 | 0.52 | 3.76 | 33.76 | 18.18 | 16.21 | 1.89 | 14.96 | 0.35 | 1.85 | 0.57 | 0.98 |
| Cosuppresion 4.6 | 0.11 | 8.18 | 0.32 | 3.58 | 19.72 | 29.19 | 20.26 | 2.04 | 13.92 | 0.29 | 1.84 | 0.55 | 0.40 |
| Cosuppresion 4.7 | 0.11 | 7.88 | 0.39 | 3.75 | 27.40 | 22.85 | 17.44 | 2.08 | 15.29 | 0.00 | 2.04 | 0.76 | 0.68 |
| Cosuppresion 4.8 | 0.13 | 7.56 | 0.41 | 3.46 | 32.27 | 20.50 | 15.45 | 1.90 | 15.47 | 0.00 | 2.02 | 0.83 | 0.90 |
| Cosuppresion 4.9 | 0.09 | 7.46 | 0.29 | 3.75 | 36.11 | 16.96 | 15.74 | 1.92 | 15.38 | 0.31 | 1.74 | 0.25 | 1.10 |
| Cosuppresion 5.1 | 0.10 | 7.68 | 0.34 | 3.88 | 36.00 | 16.77 | 15.38 | 1.90 | 15.44 | 0.32 | 1.82 | 0.36 | 1.12 |
| Cosuppresion 5.2 | 0.08 | 7.56 | 0.25 | 3.58 | 26.10 | 25.11 | 17.79 | 1.96 | 15.03 | 0.30 | 1.72 | 0.54 | 0.61 |
| Cosuppresion 5.3 | 0.08 | 7.38 | 0.20 | 3.56 | 42.24 | 13.33 | 13.32 | 1.76 | 15.19 | 0.16 | 1.61 | 1.18 | 1.59 |
| Cosuppresion 6.1 | 0.08 | 8.04 | 0.50 | 3.68 | 31.37 | 20.29 | 17.17 | 1.84 | 14.31 | 0.00 | 1.76 | 0.95 | 0.84 |
| Cosuppresion 6.2 | 0.00 | 8.50 | 0.51 | 3.91 | 18.59 | 29.33 | 19.66 | 2.46 | 14.75 | 0.00 | 2.28 | 0.00 | 0.38 |
| Control c24 pGNAP-p450 | 0.07 | 8.30 | 0.10 | 4.78 | 19.68 | 25.91 | 20.56 | 2.97 | 15.29 | 0.31 | 1.79 | 0.24 | 0.42 |

Analysis of the results indicates that transgenic plants harboring a CoP construct (indicated as "hairpin x.x" in the table) have a higher frequency of plants with oil wherein the increase in oleic acid and concomitant decrease in linolenic and linoleic acid is significant than in transgenic plants harboring cosuppression constructs. Moreover the absolute levels of increase, respectively decrease are higher respectively lower than in transgenic plants harboring cosuppression constructs.

Example 7

Modifying Oil Profile Using CoP Constructs in *Brassica*

The T-DNA vector harboring the chimeric gene encoding the CoP construct described in Example 6 is introduced in *Brassica* oilseed rape. Seeds harvested from the transgenic *Brassica* sp. are crashed and oil extracted and the composition of the fatty acids in the oil is analyzed.

Oil from transgenic *Brassica* sp. harboring the CoP construct have significantly increased oleic acid content and decreased linoleic and linolenic acid content. A T-DNA vector harboring a chimeric gene encoding a CoP construct similar to the one described in Example 6, but wherein the sequence of the sense and antisense region corresponding to the Δ12 desaturase encoding ORF is based on a homologous ORF from *Brassica* spp. is constructed and introduced in *Brassica* 20 oilseed rape.

The sequence of *Brassica* spp ORFs homologous to ill desaturase encoding ORF from Arabidopsis are available from Genbank database under Accession nrs AF042841 and AF124360.

Seeds harvested from the transgenic *Brassica* sp. are crashed and oil extracted and the composition of the fatty acids in the oil is analyzed. Oil from transgenic *Brassica* sp. harbouring the CoP construct have significantly increased oleic acid content and decreased linoleic and linolenic acid content.

Example 8

Suppression of an Endogenous Rust Resistance Gene in Flax

A CoP construct for suppression of the endogenous rust resistance gene was made consisting of 1. a CaMV35S promoter; operably linked to
2. part of an endogenous rust resistance gene (n) from flax (about 1500 bp long) in the sense orientation; ligated to
3. a similar part of the endogenous rust resistance gene from flax (about 1450 bp long) in antisense orientation so that a perfect inverted repeat without spacer sequence is generated wherein each repeat is about 1450 bp long; followed by
4. a nos terminator.

Plain antisense constructs were made using a similar fragment as described sub 3 above inserted between a CaMV35S promoter and a nos terminator.

Flax plants containing the n gene (which gives resistance to a strain of flax rust) were transformed by these CoP and antisense constructs. If suppression occurs, the plants become susceptible to the rust strain. If the construct has no effect, the transformed plants remain resistant to the rust strain.

Results

| | |
|---|---|
| 20 ngc-b sense/antisense | 3 suppressed out of 7 |
| ngc-b antisense | 0 suppressed out of 12 |

REFERENCES

An et al., 1996 The Plant Cell 8: 15-30
Bramlage et al. 1998 TIBTECH I 6, 434-438
Covey et al., 1997 Nature 385:781-782
Eckner et al. 1991 EMBO J. 10: 3513-3522
Egli and Braus, 1994 J. Biol. Chem. 1994 269: 27378-27383
Ellis et al. 1982 EMBO Journal, 6: 11-16
From et al., 1990 Biotechnology 8: 833
Cleave, 1992 Plant Mol. Biol. 20: 1203-1207
Gordon-Kamm et al., 1990 The Plant Cell 2: 603
Hamilton et al. 1998 The Plant Journal 15(6): 737-746
Harpster et al., 1988, Mol. Gen. Genet. 212, 182-1 90
Haselhoff and Gerlach, 1988 Nature 334 585-591
Hiei et al., 1994 Plant Journal 6: 271-282
Hudspeth et al., 1989 Plant Mol Biol 12: 579-589
Jefferson et al., 1987 EMBO J. 6, 3901-3907
Keil et al., 1989 EMBO J. 8: 1323-1330
Keller et al., 1988 EMBO J. 7: 3625-3633
Keller et al., 1989 Genes Bevel. 3: 1639-1646
Lee et al. 1997 Plant Journal 12: 1127-1137
Mette et al., 1999 EMBO J 18: 241-248
Metzlaff at al., 1997 Cell 88, 845-854
Miller et al., 1991 Virology 183: 711-720, 1991
Peleman et al., 1989 Gene 84: 359-369
Rubio et al., 1999 J. Virology 73: 5070-5078
Vaish et al., 1998 Nucleic Acids Res. 26: 5237-5242
van Eldik et al., 1998 Nucleic Acids Res. 26: 5176-5181
van Houdt et al., 1997 Plant Journal 12: 379-392
Wang et al., 1998 Acta Horticulturae 461:1-407
Wassenegger and Pélissier, 1998 Plant Mol. Biol. 37 349-362
Waterhouse et al., 1998 Proc. Natl. Acad. Sci USA 95: 13959-13964
Wilbur and Lipmann, 1983 Proc. Nat. Acad. Sci. USA. 80: 726

What is claimed is:

1. A chimeric DNA comprising a promoter operably linked to a target specific DNA region which encodes an unpolyadenylated hairpin RNA, wherein the unpolyadenylated hairpin RNA comprises a target specific sense nucleotide sequence and a target specific antisense nucleotide sequence, wherein the target specific antisense nucleotide sequence consists of about 20 consecutive nucleotides in a sequence identical to the sequence of the complement of a part of an RNA molecule transcribed or produced from a nucleic acid of interest in an animal cell, wherein the target specific sense nucleotide sequence consists of about 20 consecutive nucleotides in a sequence identical to the sequence of the part of the RNA molecule transcribed or produced from the nucleic acid of interest, and wherein the target specific sense nucleotide sequence and the target specific antisense nucleotide sequence are complementary to each other so as to form the unpolyadenylated hairpin RNA.

2. The chimeric DNA of claim 1, wherein said target specific sense nucleotide sequence corresponds to a translated region of the nucleic acid of interest.

3. The chimeric DNA of claim 1, wherein the target specific sense nucleotide sequence corresponds to an untranslated region of the RNA produced from the nucleic acid of interest.

4. The chimeric DNA of claim 1, wherein the promoter is recognized by a eukaryotic RNA polymerase I or III and the DNA further comprises a terminator for the polymerase I or III.

5. The chimeric DNA of claim 1, wherein the nucleic acid of interest is a gene incorporated in the genome of the animal cell.

6. The chimeric DNA of claim 1, wherein the nucleic acid of interest is an endogenous gene of the animal cell.

7. The chimeric DNA of claim 1, wherein the nucleic acid of interest is a viral nucleic acid.

8. The chimeric DNA of claim 1, wherein the unpolyadenylated RNA lacks a 5' cap structure.

9. The chimeric DNA of claim 1, wherein the animal cell is a human cell.

10. The chimeric DNA of claim 1, wherein the promoter is a constitutive promoter.

11. The chimeric DNA of claim 1, wherein the promoter is an inducible promoter.

12. The chimeric DNA of claim 1, wherein the promoter is a tissue-specific promoter.

13. The chimeric DNA of claim 1, wherein the promoter is recognized by a single subunit RNA polymerase from a bacteriophage.

14. The chimeric DNA of claim 1, wherein the nucleic acid of interest is a transgene that has been introduced into the animal cell.

15. The chimeric DNA of claim 1, wherein the unpolyadenylated hairpin RNA comprises a sequence from an intron.

16. The chimeric DNA of claim 1, wherein the promoter is recognized by a eukaryotic RNA polymerase III and the DNA further comprises a terminator for the polymerase III.

17. An animal cell in culture comprising a chimeric DNA which comprises a promoter operably linked to a target specific DNA region which encodes an unpolyadenylated hairpin RNA, wherein the unpolyadenylated hairpin RNA comprises a target specific sense nucleotide sequence and a target specific antisense nucleotide sequence, wherein the target specific antisense nucleotide sequence consists of about 20 consecutive nucleotides in a sequence identical to the sequence of the complement of a part of an RNA molecule transcribed or produced from a nucleic acid of interest in the animal cell, wherein the target specific sense nucleotide sequence consists of about 20 consecutive nucleotides in a sequence identical to the sequence of the part of the RNA molecule transcribed or produced from the nucleic acid of interest, and wherein the target specific sense nucleotide sequence and the target specific antisense nucleotide sequence are complementary to each other so as to form the unpolyadenylated hairpin RNA.

18. The animal cell in culture of claim 17, wherein the unpolyadenylated RNA is expressed in the cell.

19. The animal cell in culture of claim 17, which is a human cell in culture.

* * * * *